(12) United States Patent
Pennington et al.

(10) Patent No.: US 11,760,747 B2
(45) Date of Patent: Sep. 19, 2023

(54) SUBSTITUTED PIPERIDINO COMPOUNDS AND RELATED METHODS OF TREATMENT

(71) Applicant: Alkermes, Inc., Waltham, MA (US)

(72) Inventors: Lewis D. Pennington, Arlington, MA (US); Younggi Choi, Stow, MA (US); Hoan Huynh, Waltham, MA (US); Brian M. Aquila, Marlborough, MA (US); Ingo Andreas Mugge, Waltham, MA (US); Yuan Hu, Waltham, MA (US); James R. Woods, Waltham, MA (US); Brian Kenneth Raymer, Holliston, MA (US); Jörg Martin Bentzien, White Plains, NY (US); Jonathan Ward Lehmann, Burlington, MA (US); Srinivasa Karra, Pembroke, MA (US); Roman A. Valiulin, Cambridge, MA (US); Daljit Matharu, Lexington, MA (US)

(73) Assignee: Alkermes, Inc., Waltham, MA (US)

( * ) Notice: Subject to any disclaimer, the term of this patent is extended or adjusted under 35 U.S.C. 154(b) by 0 days.

(21) Appl. No.: 17/556,295

(22) Filed: Dec. 20, 2021

(65) Prior Publication Data
US 2022/0194926 A1 Jun. 23, 2022

Related U.S. Application Data

(60) Provisional application No. 63/128,511, filed on Dec. 21, 2020.

(51) Int. Cl.
| | |
|---|---|
| *C07D 401/14* | (2006.01) |
| *A61P 25/26* | (2006.01) |
| *C07D 211/98* | (2006.01) |
| *C07D 401/04* | (2006.01) |
| *C07D 471/04* | (2006.01) |
| *C07D 487/04* | (2006.01) |

(52) U.S. Cl.
CPC ............ *C07D 401/14* (2013.01); *A61P 25/26* (2018.01); *C07D 211/98* (2013.01); *C07D 401/04* (2013.01); *C07D 471/04* (2013.01); *C07D 487/04* (2013.01)

(58) Field of Classification Search
CPC .. C07D 401/04; C07D 401/14; C07D 211/98; A61P 25/26
See application file for complete search history.

(56) References Cited

U.S. PATENT DOCUMENTS

| | | | |
|---|---|---|---|
| 8,258,163 B2 | 9/2012 | Yanagisawa et al. | |
| 9,527,807 B2 | 12/2016 | Fukumoto et al. | |
| 9,611,262 B2 | 4/2017 | Shireman et al. | |
| 9,815,787 B2 | 11/2017 | Nagase et al. | |
| 10,017,481 B2 | 7/2018 | Obrecht et al. | |
| 10,287,305 B2 | 5/2019 | Fujimoto et al. | |
| 10,351,522 B2 | 7/2019 | Nagase et al. | |
| 10,428,023 B2 | 10/2019 | Kajita et al. | |
| 10,508,083 B2 | 12/2019 | Fujimoto et al. | |
| 10,584,097 B2 | 3/2020 | Kajita et al. | |
| 10,898,737 B2 | 1/2021 | Fujimoto et al. | |
| 11,479,552 B2 | 10/2022 | Yoshida et al. | |
| 2017/0226137 A1 | 8/2017 | Fujimoto et al. | |
| 2018/0179151 A1 | 6/2018 | Nagase et al. | |
| 2019/0031611 A1 | 1/2019 | Fujimoto et al. | |
| 2019/0040010 A1 | 2/2019 | Kajita et al. | |
| 2020/0017444 A1 | 1/2020 | Kajita et al. | |
| 2020/0115399 A1 | 4/2020 | Fujimoto et al. | |
| 2020/0207715 A1 | 7/2020 | Kajita et al. | |
| 2020/0207734 A1 | 7/2020 | Kajita et al. | |
| 2020/0247747 A1 | 8/2020 | Hattori et al. | |
| 2020/0255403 A1 | 8/2020 | Bogen et al. | |
| 2020/0385345 A1 | 12/2020 | Daini et al. | |
| 2020/0385346 A1 | 12/2020 | Fujimoto et al. | |
| 2020/0392149 A1 | 12/2020 | Mikami et al. | |
| 2021/0198240 A1 | 7/2021 | Oda et al. | |
| 2021/0269420 A1 | 9/2021 | Fujimoto et al. | |
| 2022/0017517 A1 | 1/2022 | Yoshida et al. | |
| 2022/0081441 A1 | 3/2022 | Ideue et al. | |

FOREIGN PATENT DOCUMENTS

| | | | | |
|---|---|---|---|---|
| EP | 2836485 B1 | 1/2018 | | |
| EP | 3895707 A1 | 10/2021 | | |
| EP | 3896060 A1 | 10/2021 | | |
| JP | 2022064180 A | 4/2022 | | |
| WO | WO-2012137982 A2 * | 10/2012 | ............. | A61P 25/14 |
| WO | 2013139697 A1 | 9/2013 | | |
| WO | 2016133160 A1 | 8/2016 | | |
| WO | 2017135306 A1 | 8/2017 | | |

(Continued)

OTHER PUBLICATIONS

Cox, C. D. et al., "Conformational analysis of N,N-disubstituted-1,4-diazepane orexin receptor antagonists and implications for receptor binding", Bioorganic & Medicinal Chemistry Letters, 19, DOI:10. 1016/J.BMCL.2009. 04.026, 2009, 2997-3001.

Irukayama-Tomobe, Y. et al., "Nonpeptide orexin type-2 receptor agonist ameliorates narcolepsy-cataplexy symptoms in mouse models", PNAS, vol. 114, No. 22, May 30, 2017, 5731-5736.

McGaughey, G. et al., "Shaping suvorexant: application of experimental and theoretical methods for driving synthetic designs", J. Comput. Aided Mol. Des., 28, 2014, 5-12.

(Continued)

*Primary Examiner* — Jeffrey S Lundgren
*Assistant Examiner* — Eric Tran
(74) *Attorney, Agent, or Firm* — Joseph Zucchero; Carolyn Elmore; Elmore Patent Law Group, P.C.

(57) ABSTRACT

The present invention provides compounds useful for the treatment of narcolepsy or cataplexy in a subject in need thereof. Related pharmaceutical compositions and methods are also provided herein.

121 Claims, No Drawings

(56) References Cited

FOREIGN PATENT DOCUMENTS

| WO | 2019027058 | A1 | 2/2019 |
|----|------------|----|--------|
| WO | 2019063605 | A1 | 4/2019 |
| WO | 2019191327 | A1 | 10/2019 |
| WO | 2020158958 | A1 | 8/2020 |
| WO | 2020167701 | A1 | 8/2020 |
| WO | 2021026047 | A1 | 2/2021 |
| WO | 2021048821 | A1 | 3/2021 |
| WO | 2021106975 | A1 | 6/2021 |
| WO | 2021142083 | A1 | 7/2021 |
| WO | 2022014680 | A1 | 1/2022 |
| WO | 2022040058 | A1 | 2/2022 |
| WO | 2022040070 | A1 | 2/2022 |
| WO | 2022051583 | A1 | 3/2022 |
| WO | 2022051596 | A1 | 3/2022 |
| WO | 2022094012 | A1 | 5/2022 |
| WO | 2022109117 | A1 | 5/2022 |
| WO | 2022119888 | A1 | 6/2022 |
| WO | 2022132696 | A1 | 6/2022 |
| WO | 2022187231 | A1 | 9/2022 |
| WO | 2022207935 | A1 | 10/2022 |
| WO | 2022233872 | A1 | 11/2022 |
| WO | 2022250108 | A1 | 12/2022 |
| WO | 2022269049 | A1 | 12/2022 |

OTHER PUBLICATIONS

Nagahara, T. et al., "Design and Synthesis of Non-Peptide, Selective Orexin Receptor 2 Agonists", J. Med. Chem., 58, 2015, 7931-7937.

Sabnis, R. W., "Novel 5-Alkyl Pyrrolidine Orexin Receptor Agonists for Treating Sleep Disorders", ACS Med. Chem. Lett., vol. 11, 11 (online at https://dx.doi.org/10.1021/acsmedchemlett.0c00501), Sep. 29, 2020, 2085-2086.

Turku, A. et al., "Orexin receptor agonist Yan 7874 is a weak agonist of orexin/hypocretin receptors and shows orexin receptor-independent cytotoxicity", PLOS One, 12(6): e0178526 (online at doi:10.1371/journal.pone.0178526), Jun. 2, 2017, 1-15.

Yukitake, H. et al., "TAK-925, an orexin 2 receptor-selective agonist, shows robust wakepromoting effects in mice", Pharmacology, Biochemistry and Behavior, 187, 2019, 172794.

* cited by examiner

SUBSTITUTED PIPERIDINO COMPOUNDS AND RELATED METHODS OF TREATMENT

RELATED APPLICATION

This application claims the benefit of U.S. Provisional patent application Ser. No. 63/128,511, filed on Dec. 21, 2020. The entire contents of the above-identified application are herein incorporated by reference.

TECHNICAL FIELD

The present invention relates to substituted piperidino compounds, particularly, substituted piperidino compounds having agonist activity.

BACKGROUND OF THE INVENTION

Orexin is a neuropeptide synthesized and released by a subpopulation of neurons within the lateral hypothalamus and its surrounding regions. It consists of two subtypes: orexin A and orexin B. Orexin A and orexin B bind to orexin receptors. Orexin receptors are G protein-coupled receptors expressed preferentially in the brain. There are two subtypes (type 1 and type 2) of orexin receptors (Cell, Vol. 92, 573-585, 1998). Activation of orexin receptors is known to be important for a variety of central nervous system functions, such as maintenance of wakefulness, energy homeostasis, reward processing and motivation (Saper et al., TRENDS in Neuroscience 2001; Yamanaka et al., Neuron 2003; Sakurai, Nature Reviews Neuroscience 2014).

Narcolepsy is a neurological disease that results in excessive daytime sleepiness, sudden bouts of muscular paralysis (cataplexy), and disrupted sleep patterns (Mahoney et al., Nature Reviews Neuroscience, 2019). It is known that narcolepsy is caused by the degeneration of orexin neurons. Narcoleptic symptoms can be modeled in transgenic mice engineered to degenerate orexin neurons, and their symptoms can be reversed by intraventricular administration of orexin peptides (Proc. Natl. Acad. Sci. USA, Vol. 101, 4649-4654, 2004). Studies of orexin-2 receptor knockout mice have suggested that the orexin-2 receptor plays a preferential role in maintaining wakefulness (Cell, Vol. 98, 437-451, 1999, Neuron, Vol. 38, 715-730, 2003). As such, orexin-2 receptor agonists can be therapeutic agents for narcolepsy or other disorders exhibiting excessive daytime sleepiness, such as Parkinson's disease (CNS Drugs, Vol. 27, 83-90, 2013; Brain, Vol. 130, 2007, 1586-1595).

A compound having agonist activity at the orexin-2 receptor is hypothesized to be useful as a novel therapeutic agent for narcolepsy, idiopathic hypersomnia, hypersomnia, sleep apnea syndrome, disturbance of consciousness such as coma and the like, narcolepsy syndrome, hypersomnolence syndrome characterized by hypersomnia (e.g., in Parkinson's disease, Guillain-Barre syndrome or Kleine Levin syndrome), Alzheimer's disease, obesity, insulin resistance syndrome, cardiac failure, diseases related to bone loss, or sepsis and the like. (Cell Metabolism, Vol. 9, 64-76, 2009; Neuroscience, Vol. 121, 855-863, 2003; Respiration, Vol. 71, 575-579, 2004; Peptides, Vol. 23, 1683-1688, 2002; WO 2015/073707; Journal of the American College of Cardiology, Vol. 66, 2015, pages 2522-2533; WO 2015/048091; WO 2015/147240).

Some compounds having orexin-2 receptor agonist activity have been reported (U.S. Pat. No. 8,258,163; WO 2015/088000; WO 2014/198880; Journal of Medicinal Chemistry, Vol. 58, pages 7931-7937; US 20190040010; US 20190031611; US 20170226137). However, it is considered that these compounds are not satisfactory, for example, in terms of activity, pharmacokinetics, permeability into the brain/central nervous system or safety, and the development of an improved compound having orexin-2 receptor agonist activity is desired.

SUMMARY OF THE INVENTION

The present invention aims to provide substituted piperidino compounds having orexin-2 receptor agonist activity.

Accordingly, in an initial aspect, the present invention provides a compound represented by Formula I-A or a pharmaceutically acceptable salt thereof:

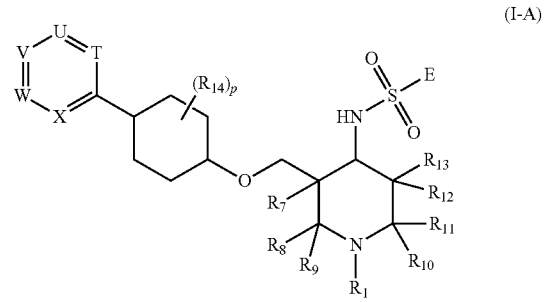

(I-A)

or a pharmaceutically acceptable salt thereof;
wherein:
T is $CR_6$ or N;
U is $CR_5$ or N;
V is $CR_4$ or N;
W is $CR_3$ or N;
X is $CR_2$ or N;
and provided that

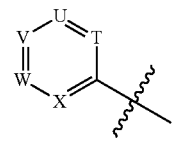

includes no more than 3 nitrogen atoms in the ring;
E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, and $C_1$-$C_3$ alkylene-(4- to 10-membered heterocyclyl) wherein the $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl;
$R_a$ and $R_b$ are each, independently, H or unsubstituted $C_1$-$C_3$ alkyl;
$R_1$ is $(CR_cR_d)_n$—$(C_6$-$C_{10}$ aryl) or $(CR_cR_d)_n$-(5- to 10-membered heteroaryl) wherein the aryl or heteroaryl is unsubstituted or substituted with one or more halogen, hydroxyl, unsubstituted $C_1$-$C_3$ alkyl, or $C_1$-$C_3$ alkyl substituted with one or more halogen or deuterium;

$R_c$ and $R_d$ are each, independently, H, unsubstituted $C_1$-$C_3$ alkyl, or $C_1$-$C_3$ alkyl substituted with one or more halogen or deuterium;

n is 0 or 1;

each of $R_2$, $R_3$, $R_4$, $R_5$, and $R_6$, when present, is, independently, selected from the group consisting of H, halogen, deuterium, hydroxyl, cyano, unsubstituted $C_1$-$C_3$alkyl, and $C_1$-$C_3$alkyl substituted with one or more halogen or deuterium;

each of $R_7$, $R_8$, $R_9$, $R_{10}$, $R_{11}$, $R_{12}$, and $R_{13}$ is, independently, H, halogen, unsubstituted $C_1$-$C_3$ alkyl, or $C_1$-$C_3$ alkyl substituted with one or more halogen or deuterium;

or, alternatively, $R_8$ and $R_{11}$, together form an unsubstituted $C_1$-$C_3$ alkylene or a $C_1$-$C_3$ alkylene substituted with one or more halogen;

or, alternatively, $R_9$ and $R_{10}$, together form an unsubstituted $C_1$-$C_3$ alkylene or a $C_1$-$C_3$ alkylene substituted with one or more halogen;

p is 0, 1, 2, 3, or 4; and each $R_{14}$ is, independently, selected from the group consisting of deuterium, halogen, hydroxyl, and cyano.

In one embodiment, provided herein are compounds of Formula I-A having the structure of Formula I or a pharmaceutically acceptable salt thereof:

(I)

or a pharmaceutically acceptable salt thereof;

wherein:

T is $CR_6$ or N;
U is $CR_5$ or N;
V is $CR_4$ or N;
W is $CR_3$ or N;
X is $CR_2$ or N;

and provided that includes no more than 3 nitrogen atoms in the ring;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, and $C_1$-$C_3$ alkylene-(4- to 10-membered heterocyclyl) wherein the $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl;

$R_a$ and $R_b$ are each, independently, H or unsubstituted $C_1$-$C_3$ alkyl;

$R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted or substituted with one or more halogen, hydroxyl, unsubstituted $C_1$-$C_3$ alkyl, or $C_1$-$C_3$ alkyl substituted with one or more halogen or deuterium;

$R_c$ and $R_d$ are each, independently, H, unsubstituted $C_1$-$C_3$ alkyl, or $C_1$-$C_3$ alkyl substituted with one or more halogen or deuterium;

n is 0 or 1;

each of $R_2$, $R_3$, $R_4$, $R_5$, and $R_6$, when present, is, independently, selected from the group consisting of H, halogen, deuterium, hydroxyl, cyano, unsubstituted $C_1$-$C_3$ alkyl, and $C_1$-$C_3$ alkyl substituted with one or more halogen or deuterium;

each of $R_7$, $R_8$, $R_9$, $R_{10}$, $R_{11}$, $R_{12}$, and $R_{13}$ is, independently, H, halogen, unsubstituted $C_1$-$C_3$ alkyl, or $C_1$-$C_3$ alkyl substituted with one or more halogen or deuterium;

or, alternatively, $R_8$ and $R_{11}$, together form an unsubstituted $C_1$-$C_3$ alkylene or a $C_1$-$C_3$ alkylene substituted with one or more halogen;

or, alternatively, $R_9$ and $R_{10}$, together form an unsubstituted $C_1$-$C_3$ alkylene or a $C_1$-$C_3$ alkylene substituted with one or more halogen;

p is 0, 1, 2, 3, or 4; and each $R_{14}$ is, independently, selected from the group consisting of deuterium, halogen, hydroxyl, and cyano.

Also provided herein is a pharmaceutical composition comprising a compound of Formula I-A or I, or a pharmaceutically acceptable salt thereof, and a pharmaceutically acceptable carrier.

In another aspect, provided herein is a method of treating narcolepsy in a subject in need thereof comprising administering to the subject a compound of Formula I-A or I, or a pharmaceutically acceptable salt thereof.

In another aspect, provided herein is a method of treating cataplexy in a subject in need thereof comprising administering to the subject a compound of Formula I-A or I, or a pharmaceutically acceptable salt thereof.

DETAILED DESCRIPTION OF THE INVENTION

Provided herein are compounds, e.g., the compounds of Formula I-A or I, or pharmaceutically acceptable salts thereof, that are useful in the treatment of narcolepsy or cataplexy in a subject.

In a non-limiting aspect, these compounds may modulate the orexin-2 receptor. In a particular embodiment, the compounds provided herein are considered orexin-2 agonists. As such, in one aspect, the compounds provided herein are useful in treatment of narcolepsy in a subject by acting as an agonist of the orexin-2 receptor.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e., to at least one) of the grammatical object of the article. By way of example, "an element" means one element or more than one element. Furthermore, use of the term "including" as well as other forms, such as "include," "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used to herein, the term "$EC_{50}$" refers to the concentration of a compound required to achieve an effect that is 50% of the maximal observed effect of a compound.

The term "agonist," as used herein, refers to a compound that, when contacted with a target of interest (e.g., the orexin-2 receptor), causes an increase in the magnitude of a certain activity or function of the target compared to the magnitude of the activity or function observed in the absence of the agonist.

The term "treat," "treated," "treating," or "treatment" includes the diminishment or alleviation of at least one symptom associated or caused by the state, disorder or disease being treated. In certain embodiments, the treatment comprises bringing into contact with the orexin-2 receptor an effective amount of a compound of the invention for conditions related to narcolepsy or cataplexy.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject, or individual is human.

As used herein, the terms "effective amount," "pharmaceutically effective amount," and "therapeutically effective amount" refer to a nontoxic but sufficient amount of an agent to provide the desired biological result. That result may be reduction or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salt" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The phrase "pharmaceutically acceptable salt" is not limited to a mono, or 1:1, salt. For example, "pharmaceutically acceptable salt" also includes bis-salts, such as a bis-hydrochloride salt. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations.

As used herein, "pharmaceutically acceptable carrier" also includes any and all coatings, antibacterial and antifungal agents, and absorption delaying agents, and the like that are compatible with the activity of the compound useful within the invention and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ alkyl means an alkyl having one to six carbon atoms) and includes straight and branched chains. Examples include methyl, ethyl, propyl, isopropyl, butyl, isobutyl, tert-butyl, pentyl, neopentyl, and hexyl. Other examples of $C_1$-$C_6$-alkyl include ethyl, methyl, isopropyl, isobutyl, n-pentyl, and n-hexyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "alkylene" refers to divalent aliphatic hydrocarbyl groups, for example, having from 1 to 4 carbon atoms that are either straight-chained or branched. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), and the like.

As used herein, the term "alkenyl" denotes a monovalent group derived from a hydrocarbon moiety containing at least two carbon atoms and at least one carbon-carbon double bond. The double bond may or may not be the point of attachment to another group. Alkenyl groups (e.g., $C_2$-$C_8$-alkenyl) include, but are not limited to, for example, ethenyl, propenyl, prop-1-en-2-yl, butenyl, 1-methyl-2-buten-1-yl, heptenyl, octenyl and the like.

As used herein, the term "alkynyl" denotes a monovalent group derived from a hydrocarbon moiety containing at least two carbon atoms and at least one carbon-carbon triple bond. The triple bond may or may not be the point of attachment to another group. Alkynyl groups (e.g., $C_2$-$C_8$-alkynyl) include, but are not limited to, for example, ethynyl, propynyl, prop-1-yn-2-yl, butynyl, 1-methyl-2-butyn-1-yl, heptynyl, octynyl and the like.

As used herein, the term "alkoxy," refers to the group —O-alkyl, wherein alkyl is as defined herein. Alkoxy includes, by way of example, methoxy, ethoxy, n-propoxy, isopropoxy, n-butoxy, sec-butoxy, t-butoxy and the like.

As used herein, the term "cycloalkyl" means a non-aromatic carbocyclic system that is partially or fully saturated having 1, 2 or 3 rings wherein such rings may be fused. The term "fused" means that a second ring is present (i.e., attached or formed) by having two adjacent atoms in common (i.e., shared) with the first ring. Cycloalkyl also includes bicyclic structures that may be bridged or spirocyclic in nature with each individual ring within the bicycle varying from 3-8 atoms. The term "cycloalkyl" includes, but is not limited to, cyclopropyl, cyclobutyl, cyclopentyl, cyclohexyl, bicyclo[3.1.0]hexyl, spiro[3.3]heptanyl, and bicyclo[1.1.1]pentyl.

As used herein, the term "heterocyclyl" means a non-aromatic carbocyclic system containing 1, 2, 3 or 4 heteroatoms selected independently from N, O, and S and having 1, 2 or 3 rings wherein such rings may be fused, wherein fused is defined above. Heterocyclyl also includes bicyclic structures that may be bridged or spirocyclic in nature with each individual ring within the bicycle varying from 3-8 atoms, and containing 0, 1, or 2 N, O, or S atoms. The term "heterocyclyl" includes cyclic esters (i.e., lactones) and cyclic amides (i.e., lactams) and also specifically includes, but is not limited to, epoxidyl, oxetanyl, tetrahydrofuranyl, tetrahydropyranyl (i.e., oxanyl), pyranyl, dioxanyl, aziridinyl, azetidinyl, pyrrolidinyl, 2,5-dihydro-1H-pyrrolyl, oxazolidinyl, thiazolidinyl, piperidinyl, morpholinyl, piperazinyl, thiomorpholinyl, 1,3-oxazinanyl, 1,3-thiazinanyl, and the like.

As used herein, the term "bridged bicyclic heterocyclyl" refers to non-aromatic heterocyclic ring systems in which two rings share more than two atoms. The bridged bicyclic ring system can be, for example, [3.2.1] bicyclic ring systems such as azabicyclo[3.2.1]octane or [3.1.1] bicyclic ring systems such as azabicyclo[3.1.1]heptane.

It is to be understood that if an aryl, heteroaryl, cycloalkyl, or heterocyclyl moiety may be bonded or otherwise attached to a designated moiety through differing ring atoms (i.e., shown or described without denotation of a specific point of attachment), then all possible points are intended, whether through a carbon atom or, for example, a trivalent nitrogen atom. For example, the term "pyridinyl" means 2-, 3- or 4-pyridinyl, the term "thiophenyl" means 2- or 3-thiophenyl, and so forth.

As used herein, the term "substituted" means that an atom or group of atoms has replaced hydrogen as the substituent attached to another group.

Compounds of the Invention

Accordingly, in an initial aspect, the present invention provides a compound represented by Formula I-A or a pharmaceutically acceptable salt thereof:

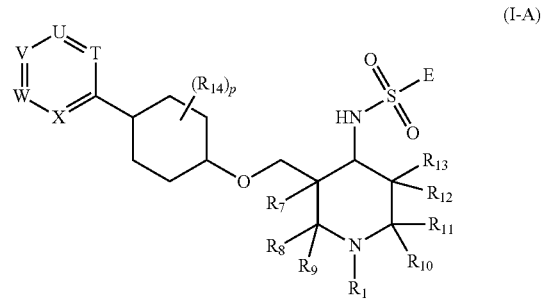

(I-A)

or a pharmaceutically acceptable salt thereof;

wherein:

T is CR$_6$ or N;

U is CR$_5$ or N;

V is CR$_4$ or N;

W is CR$_3$ or N;

X is CR$_2$ or N;

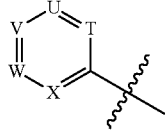

includes no more than 3 nitrogen atoms in the ring;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, and $C_1$-$C_3$ alkylene-(4- to 10-membered heterocyclyl) wherein the $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl;

$R_a$ and $R_b$ are each, independently, H or unsubstituted $C_1$-$C_3$ alkyl;

$R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted or substituted with one or more halogen, hydroxyl, unsubstituted $C_1$-$C_3$ alkyl, or $C_1$-$C_3$ alkyl substituted with one or more halogen or deuterium;

$R_c$ and $R_d$ are each, independently, H, unsubstituted $C_1$-$C_3$ alkyl, or $C_1$-$C_3$ alkyl substituted with one or more halogen or deuterium;

n is 0 or 1;

each of $R_2$, $R_3$, $R_4$, $R_5$, and $R_6$, when present, is, independently, selected from the group consisting of H, halogen, deuterium, hydroxyl, cyano, unsubstituted $C_1$-$C_3$alkyl, and $C_1$-$C_3$alkyl substituted with one or more halogen or deuterium;

each of $R_7$, $R_8$, $R_9$, $R_{10}$, $R_{11}$, $R_{12}$, and $R_{13}$ is, independently, H, halogen, unsubstituted $C_1$-$C_3$ alkyl, or $C_1$-$C_3$ alkyl substituted with one or more halogen or deuterium;

or, alternatively, $R_8$ and $R_{11}$, together form an unsubstituted $C_1$-$C_3$ alkylene or a $C_1$-$C_3$ alkylene substituted with one or more halogen;

or, alternatively, $R_9$ and $R_{10}$, together form an unsubstituted $C_1$-$C_3$ alkylene or a $C_1$-$C_3$ alkylene substituted with one or more halogen;

p is 0, 1, 2, 3, or 4; and each $R_{14}$ is, independently, selected from the group consisting of deuterium, halogen, hydroxyl, and cyano.

In one embodiment, provided herein are compounds of Formula I-A having the structure of Formula I or a pharmaceutically acceptable salt thereof:

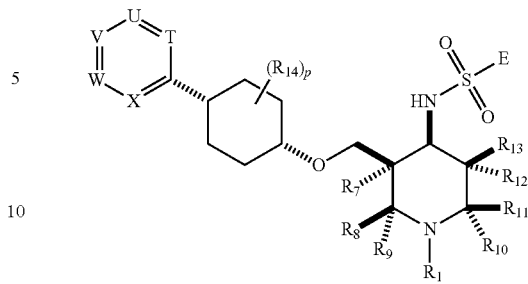

or a pharmaceutically acceptable salt thereof;
wherein:
T is $CR_6$ or N;
U is $CR_5$ or N;
V is $CR_4$ or N;
W is $CR_3$ or N;
X is $CR_2$ or N;
and provided that

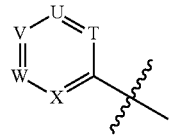

includes no more than 3 nitrogen atoms in the ring;

E is selected from the group consisting of $NR_aR_b$, $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, and $C_1$-$C_3$ alkylene-(4- to 10-membered heterocyclyl) wherein the $C_1$-$C_3$ alkylene-$NR_aR_b$, $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl;

$R_a$ and $R_b$ are each, independently, H or unsubstituted $C_1$-$C_3$ alkyl;

$R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted or substituted with one or more halogen, hydroxyl, unsubstituted $C_1$-$C_3$ alkyl, or $C_1$-$C_3$ alkyl substituted with one or more halogen or deuterium;

$R_c$ and $R_d$ are each, independently, H, unsubstituted $C_1$-$C_3$ alkyl, or $C_1$-$C_3$ alkyl substituted with one or more halogen or deuterium;

n is 0 or 1;

each of $R_2$, $R_3$, $R_4$, $R_5$, and $R_6$, when present, is, independently, selected from the group consisting of H, halogen, deuterium, hydroxyl, cyano, unsubstituted $C_1$-$C_3$alkyl, and $C_1$-$C_3$alkyl substituted with one or more halogen or deuterium;

each of $R_7$, $R_8$, $R_9$, $R_{10}$, $R_{11}$, $R_{12}$, and $R_{13}$ is, independently, H, halogen, unsubstituted $C_1$-$C_3$ alkyl, or $C_1$-$C_3$ alkyl substituted with one or more halogen or deuterium;

or, alternatively, $R_8$ and $R_{11}$, together form an unsubstituted $C_1$-$C_3$ alkylene or a $C_1$-$C_3$ alkylene substituted with one or more halogen;

or, alternatively, $R_9$ and $R_{10}$, together form an unsubstituted $C_1$-$C_3$ alkylene or a $C_1$-$C_3$ alkylene substituted with one or more halogen;

p is 0, 1, 2, 3, or 4; and each $R_{14}$ is, independently, selected from the group consisting of deuterium, halogen, hydroxyl, and cyano.

In one embodiment of Formula (I),

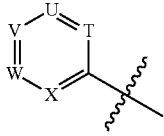

is selected from the group consisting of:

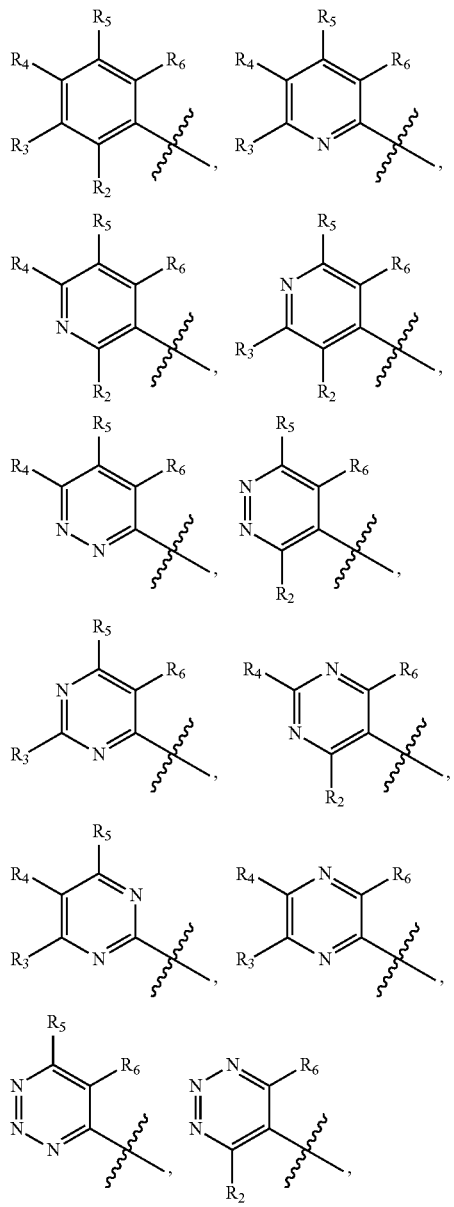

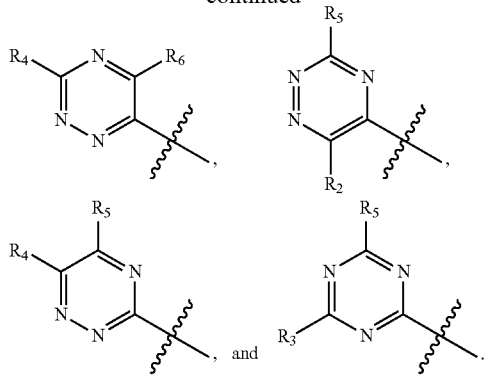

In another embodiment of Formula (I),

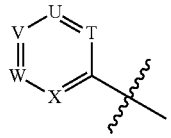

is selected from the group consisting of:

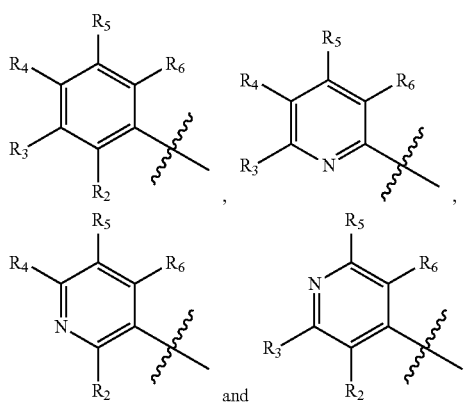

In another embodiment of Formula (I),

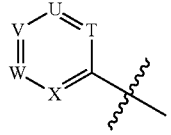

selected from the group consisting of:

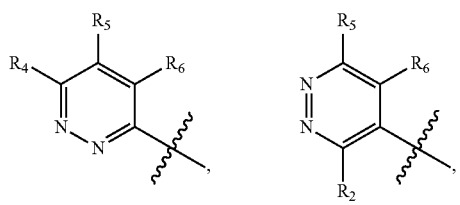

-continued
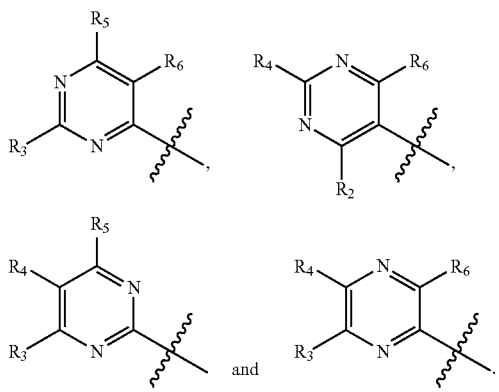
In another embodiment of Formula (I), of:
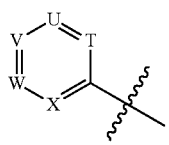
is selected from the group consisting
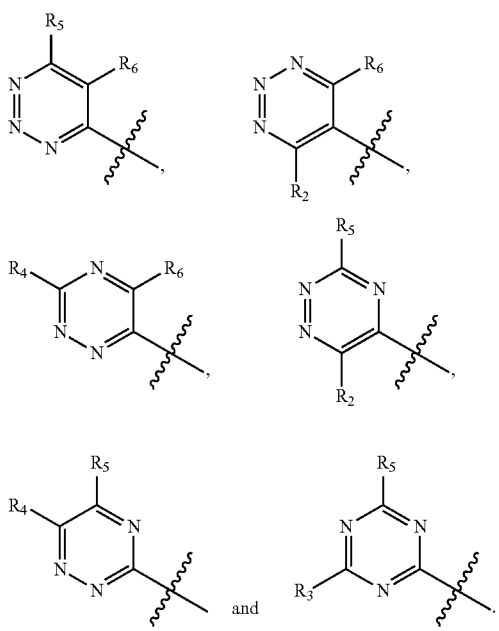
In another embodiment of Formula (I),
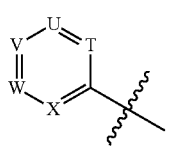
is selected from the group consisting of:
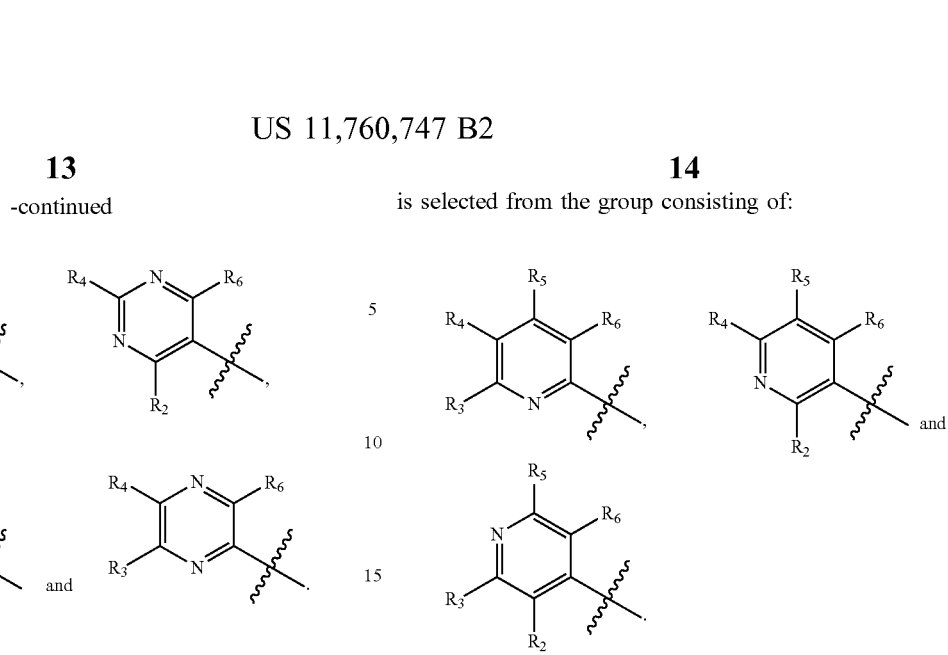
In another embodiment of Formula (I),
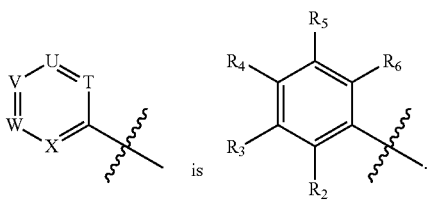
In another embodiment of Formula (I),
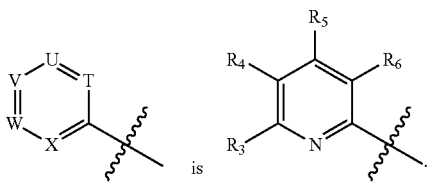
In another embodiment of Formula (I),
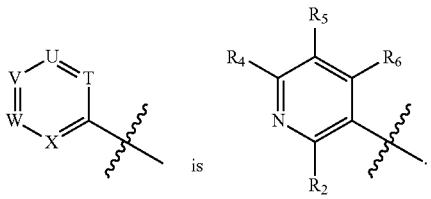
In another embodiment of Formula (I),
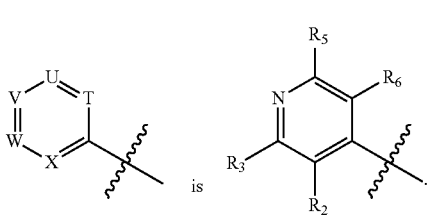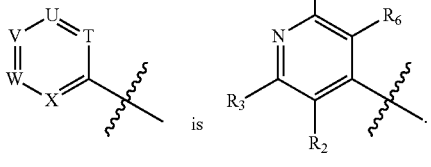

In another embodiment of Formula (I),
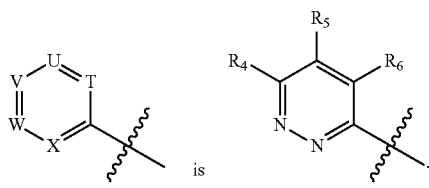 is 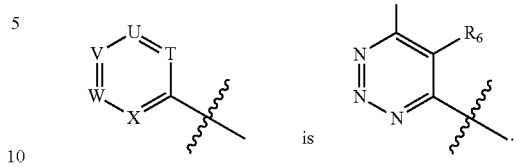
In another embodiment of Formula (I),
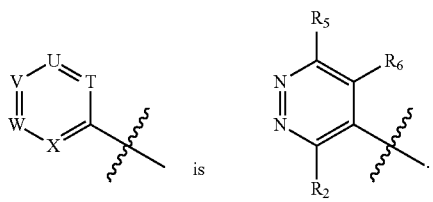 is 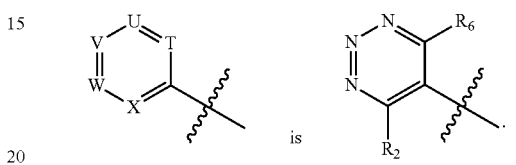
In another embodiment of Formula (I),
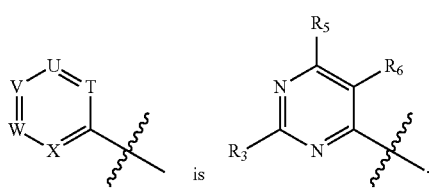 is 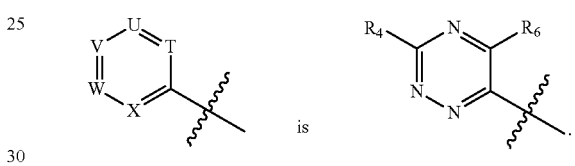
In another embodiment of Formula (I),
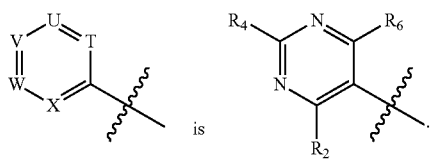 is 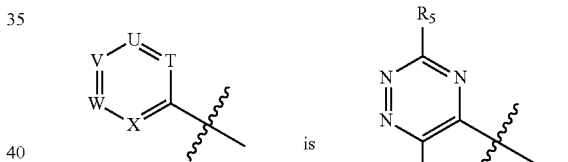
In another embodiment of Formula (I),
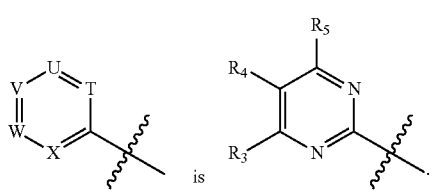 is 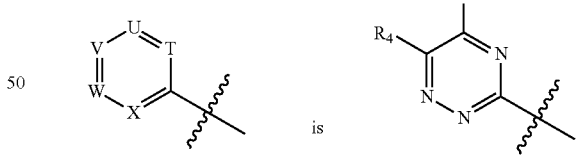
In another embodiment of Formula (I),
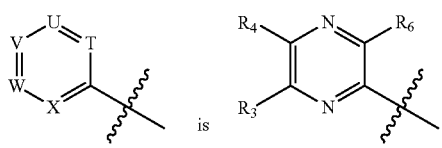 is 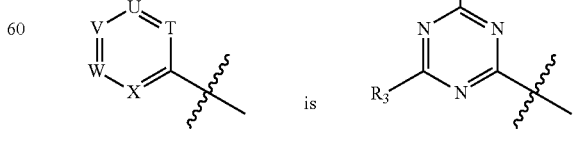
In another embodiment of Formula (I), p is 0. In another embodiment of Formula (I), p is 1. In another embodiment of Formula (I), p is 2. In another embodiment of Formula (I), p is 3. In another embodiment of Formula (I), p is 4. In another embodiment of Formula (I), p is 0, 1 or 2. In another embodiment of Formula (I), p is 0 or 1.

In another embodiment of Formula (I), p is 1 and $R_{14}$ is deuterium. In another embodiment of Formula (I), p is 1 and $R_{14}$ is halogen. In another embodiment of Formula (I), p is 1 and $R_{14}$ is fluorine. In another embodiment of Formula (I), p is 1 and $R_{14}$ is hydroxyl. In another embodiment of Formula (I), p is 1 and $R_{14}$ is cyano. In another embodiment of Formula (I), p is 2 and each $R_{14}$ is hydroxyl. In another embodiment of Formula (I), p is 2 and each $R_{14}$ is halogen. In another embodiment of Formula (I), p is 2 and each $R_{14}$ is fluorine.

In another embodiment of Formula (I), E is $NR_aR_b$. In another embodiment of Formula (I), E is $C_1$-$C_3$ alkylene-$NR_aR_b$. In another embodiment of Formula (I), E is unsubstituted $C_1$-$C_3$ alkyl, unsubstituted $C_2$-$C_4$ alkenyl or unsubstituted $C_2$-$C_4$ alkynyl. In another embodiment of Formula (I), E is $C_1$-$C_3$ alkyl, $C_2$-$C_4$ alkenyl or $C_2$-$C_4$ alkynyl substituted with one or more halogen, hydroxyl, $C_1$-$C_3$ alkyl, or $C_1$-$C_3$ alkoxyl. In another embodiment of Formula (I), E is unsubstituted $C_1$-$C_3$ alkyl. In another embodiment of Formula (I), E is $C_1$-$C_3$ alkyl substituted with one or more halogen, hydroxyl, $C_1$-$C_3$ alkyl, or $C_1$-$C_3$ alkoxyl. In another embodiment of Formula (I), E is unsubstituted $C_3$-$C_8$ cycloalkyl. In another embodiment of Formula (I), E is $C_3$-$C_8$ cycloalkyl substituted with one or more halogen, hydroxyl, $C_1$-$C_3$ alkyl, or $C_1$-$C_3$ alkoxyl. In another embodiment of Formula (I), E is unsubstituted $C_1$-$C_3$ alkylene-($C_3$-$C_8$ cycloalkyl). In another embodiment of Formula (I), E is $C_1$-$C_3$ alkylene-($C_3$-$C_8$ cycloalkyl) substituted with one or more halogen, hydroxyl, $C_1$-$C_3$ alkyl, or $C_1$-$C_3$ alkoxyl. In another embodiment of Formula (I), E is unsubstituted 4- to 10-membered heterocyclyl. In another embodiment of Formula (I), E is 4- to 10-membered heterocyclyl substituted with one or more halogen, hydroxyl, $C_1$-$C_3$ alkyl, or $C_1$-$C_3$ alkoxyl. In another embodiment of Formula (I), E is unsubstituted $C_1$-$C_3$ alkylene-(4- to 10-membered heterocyclyl). In another embodiment of Formula (I), E is $C_1$-$C_3$ alkylene-(4- to 10-membered heterocyclyl) substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl), wherein the $C_1$-$C_3$ alkyl, $C_2$-$C_4$ alkenyl, $C_2$-$C_4$ alkynyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl), wherein the $C_1$-$C_3$ alkyl, $C_3$-$C_8$ cycloalkyl, $C_1$-$C_3$ alkylene-($C_3$-$C_8$ cycloalkyl), 4- to 10-membered heterocyclyl, or $C_1$-$C_3$ alkylene-(4- to 10-membered heterocyclyl) is unsubstituted or substituted with one or more halogen, hydroxyl, $C_1$-$C_3$ alkyl, or $C_1$-$C_3$ alkoxyl.

In another embodiment of Formula (I), E is $C_1$-$C_3$ alkyl, $C_3$-$C_8$ cycloalkyl, or $C_1$-$C_3$ alkylene-($C_3$-$C_8$ cycloalkyl), wherein the $C_1$-$C_3$ alkyl, $C_3$-$C_8$ cycloalkyl, or $C_1$-$C_3$ alkylene-($C_3$-$C_8$ cycloalkyl) is unsubstituted or substituted with one or more halogen, hydroxyl, $C_1$-$C_3$ alkyl, or $C_1$-$C_3$ alkoxyl.

In another embodiment of Formula (I), $R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted. In another embodiment of Formula (I), $R_1$ is $(CR_cR_d)_n$—($C_6$-$C_{10}$ aryl) or $(CR_cR_d)_n$-(5- to 10-membered heteroaryl) wherein the aryl or heteroaryl is substituted with one or more halogen, hydroxyl, unsubstituted $C_1$-$C_3$ alkyl, or $C_1$-$C_3$ alkyl substituted with one or more halogen or deuterium.

In another embodiment of Formula (I), $R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted and further wherein n is 0. In another embodiment of Formula (I), $R_1$ is $(CR_cR_d)_n$—($C_6$-$C_{10}$ aryl) or $(CR_cR_d)_n$-(5- to 10-membered heteroaryl) wherein the aryl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 0.

In another embodiment of Formula (I), $R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted and further wherein n is 1. In another embodiment of Formula (I), $R_1$ is $(CR_cR_d)_n$—($C_6$-$C_{10}$ aryl) or $(CR_cR_d)_n$-(5- to 10-membered heteroaryl) wherein the aryl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 1.

In another embodiment of Formula (I), $R_1$ is $(CR_cR_d)_n$—($C_6$-$C_{10}$ aryl) wherein the aryl is unsubstituted. In another embodiment of Formula (I), $R_1$ is $(CR_cR_d)_n$—($C_6$-$C_{10}$ aryl) wherein the aryl is substituted with one or more halogen, hydroxyl, unsubstituted $C_1$-$C_3$ alkyl, or $C_1$-$C_3$ alkyl substituted with one or more halogen or deuterium.

In another embodiment of Formula (I), $R_1$ is $(CR_cR_d)_n$—($C_6$-$C_{10}$ aryl) wherein the aryl is unsubstituted and further wherein n is 0. In another embodiment of Formula (I), $R_1$ is $(CR_cR_d)_n$—($C_6$-$C_{10}$ aryl) wherein the aryl is substituted with one or more halogen, hydroxyl, unsubstituted $C_1$-$C_3$ alkyl, or $C_1$-$C_3$ alkyl substituted with one or more halogen or deuterium and further wherein n is 0.

In another embodiment of Formula (I), $R_1$ is $(CR_cR_d)_n$—($C_6$-$C_{10}$ aryl) wherein the aryl is unsubstituted and further wherein n is 1. In another embodiment of Formula (I), $R_1$ is $(CR_cR_d)_n$—($C_6$-$C_{10}$ aryl) wherein the aryl is substituted with one or more halogen, hydroxyl, unsubstituted $C_1$-$C_3$ alkyl, or $C_1$-$C_3$ alkyl substituted with one or more halogen or deuterium and further wherein n is 1.

In another embodiment of Formula (I), $R_1$ is $(CR_cR_d)_n$-(5- to 10-membered heteroaryl) wherein the heteroaryl is unsubstituted. In another embodiment of Formula (I), $R_1$ is $(CR_cR_d)_n$-(5- to 10-membered heteroaryl) wherein the heteroaryl is substituted with one or more halogen, hydroxyl, unsubstituted $C_1$-$C_3$ alkyl, or $C_1$-$C_3$ alkyl substituted with one or more halogen or deuterium.

In another embodiment of Formula (I), $R_1$ is $(CR_cR_d)_n$-(5- to 10-membered heteroaryl) wherein the heteroaryl is unsubstituted and further wherein n is 0. In another embodiment of Formula (I), $R_1$ is $(CR_cR_d)_n$-(5- to 10-membered heteroaryl) wherein the heteroaryl is substituted with one or more halogen, hydroxyl, unsubstituted $C_1$-$C_3$ alkyl, or $C_1$-$C_3$ alkyl substituted with one or more halogen or deuterium and further wherein n is 0.

In another embodiment of Formula (I), $R_1$ is $(CR_cR_d)_n$-(5- to 10-membered heteroaryl) wherein the heteroaryl is unsubstituted and further wherein n is 1. In another embodiment of Formula (I), $R_1$ is $(CR_cR_d)_n$-(5- to 10-membered heteroaryl) wherein the heteroaryl is substituted with one or more halogen, hydroxyl, unsubstituted $C_1$-$C_3$ alkyl, or $C_1$-$C_3$ alkyl substituted with one or more halogen or deuterium and further wherein n is 1.

In another embodiment of Formula (I), $R_1$ is $(CR_cR_d)_n$-(phenyl) or $(CR_cR_d)_n$-(5- to 7-membered heteroaryl) wherein the phenyl or heteroaryl is unsubstituted. In another embodiment of Formula (I), $R_1$ is $(CR_cR_d)_n$-(phenyl) or $(CR_cR_d)_n$-(5- to 7-membered heteroaryl) wherein the phenyl or heteroaryl is substituted with one or more halogen, hydroxyl, unsubstituted $C_1$-$C_3$ alkyl, or $C_1$-$C_3$ alkyl substituted with one or more halogen or deuterium.

In another embodiment of Formula (I), $R_1$ is $(CR_cR_d)_n$-(phenyl) or $(CR_cR_d)_n$-(5- to 7-membered heteroaryl) wherein the phenyl or heteroaryl is unsubstituted and further wherein n is 0. In another embodiment of Formula (I), $R_1$ is $(CR_cR_d)_n$-(phenyl) or $(CR_cR_d)_n$-(5- to 7-membered heteroaryl) wherein the phenyl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 0.

In another embodiment of Formula (I), $R_1$ is $(CR_cR_d)_n$-(phenyl) or $(CR_cR_d)_n$-(5- to 7-membered heteroaryl) wherein the phenyl or heteroaryl is unsubstituted and further wherein n is 1. In another embodiment of Formula (I), $R_1$ is $(CR_cR_d)_n$-(phenyl) or $(CR_cR_d)_n$-(5- to 7-membered heteroaryl) wherein the phenyl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 1.

In another embodiment of Formula (I), $R_1$ is $(CR_cR_d)_n$-(phenyl) or $(CR_cR_d)_n$-(6-membered heteroaryl) wherein the phenyl or heteroaryl is unsubstituted. In another embodiment of Formula (I), $R_1$ is $(CR_cR_d)_n$-(phenyl) or $(CR_cR_d)_n$-(6-membered heteroaryl) wherein the phenyl or heteroaryl is substituted with one or more halogen, hydroxyl, unsubstituted $C_1$-$C_3$ alkyl, or $C_1$-$C_3$ alkyl substituted with one or more halogen or deuterium.

In another embodiment of Formula (I), $R_1$ is $(CR_cR_d)_n$-(phenyl) or $(CR_cR_d)_n$-(6-membered heteroaryl) wherein the phenyl or heteroaryl is unsubstituted and further wherein n is 0. In another embodiment of Formula (I), $R_1$ is $(CR_cR_d)_n$-(phenyl) or $(CR_cR_d)_n$-(6-membered heteroaryl) wherein the phenyl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 0.

In another embodiment of Formula (I), $R_1$ is $(CR_cR_d)_n$-(phenyl) or $(CR_cR_d)_n$-(6-membered heteroaryl) wherein the phenyl or heteroaryl is unsubstituted and further wherein n is 1. In another embodiment of Formula (I), $R_1$ is $(CR_cR_d)_n$-(phenyl) or $(CR_cR_d)_n$-(6-membered heteroaryl) wherein the phenyl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 1.

In another embodiment of Formula (I), each of $R_2$, $R_3$, $R_4$, $R_5$, and $R_6$, when present, is, independently, selected from the group consisting of H, halogen, hydroxyl, cyano, unsubstituted $C_1$-$C_3$alkyl, and $C_1$-$C_3$alkyl substituted with one or more halogen.

In another embodiment of Formula (I), each of $R_2$, $R_3$, $R_4$, $R_5$, and $R_6$, when present, is, independently, selected from the group consisting of H, halogen, hydroxyl, and unsubstituted $C_1$-$C_3$alkyl.

In another embodiment of Formula (I), each of $R_2$, $R_3$, $R_4$, $R_5$, and $R_6$, when present, is, independently, selected from the group consisting of H, halogen, and unsubstituted $C_1$-$C_3$alkyl.

In another embodiment of Formula (I), each of $R_2$, $R_3$, $R_4$, $R_5$, and $R_6$, when present, is, independently, selected from H or halogen. In another embodiment of Formula (I), each of $R_2$, $R_3$, $R_4$, $R_5$, and $R_6$, when present, is, independently, selected from H or fluorine. In another embodiment of Formula (I), each of $R_2$, $R_3$, $R_4$, $R_5$, and $R_6$, when present, is, independently, selected from H or chlorine. In another embodiment of Formula (I), each of $R_2$, $R_3$, $R_4$, $R_5$, and $R_6$, when present, is, independently, selected from H or unsubstituted $C_1$ alkyl. In another embodiment of Formula (I), each of $R_2$, $R_3$, $R_4$, $R_5$, and $R_6$, when present, is, independently, selected from H or hydroxyl. In another embodiment of Formula (I), each of $R_2$, $R_3$, $R_4$, $R_5$, and $R_6$, when present, is H.

In another embodiment of Formula (I), each of $R_7$, $R_8$, $R_9$, $R_{10}$, $R_{11}$, $R_{12}$, and $R_{13}$ is, independently, H, halogen, unsubstituted $C_1$-$C_3$ alkyl, or $C_1$-$C_3$ alkyl substituted with one or more halogen or deuterium.

In another embodiment of Formula (I), $R_8$ and $R_{11}$, together, form an unsubstituted $C_1$-$C_3$ alkylene or a $C_1$-$C_3$ alkylene substituted with one or more halogen. In another embodiment of Formula (I), $R_8$ and $R_{11}$, together, form an unsubstituted $C_2$ alkylene or a $C_2$ alkylene substituted with one or more halogen. In another embodiment of Formula (I), $R_8$ and $R_{11}$, together, form an azabicyclo[3.2.1]octanyl bridged bicyclic heterocyclyl.

In another embodiment of Formula (I), $R_9$ and $R_{10}$, together, form an unsubstituted $C_1$-$C_3$ alkylene or a $C_1$-$C_3$ alkylene substituted with one or more halogen. In another embodiment of Formula (I), $R_9$ and $R_{10}$, together, form an unsubstituted $C_2$ alkylene or a $C_2$ alkylene substituted with one or more halogen. In another embodiment of Formula (I), $R_9$ and $R_{10}$, together, form an azabicyclo[3.2.1]octanyl bridged bicyclic heterocyclyl.

In another embodiment of Formula (I), each of $R_7$, $R_8$, $R_9$, $R_{10}$, $R_{11}$, $R_{12}$, and $R_{13}$ is, independently, H, halogen, or unsubstituted $C_1$-$C_3$ alkyl. In another embodiment of Formula (I), each of $R_7$, $R_8$, $R_9$, $R_{10}$, $R_{11}$, $R_{12}$, and $R_{13}$ is, independently, H, fluorine, or unsubstituted $C_1$-$C_3$ alkyl. In another embodiment of Formula (I), each of $R_7$, $R_8$, $R_9$, $R_{10}$, $R_{11}$, $R_{12}$, and $R_{13}$ is, independently, H, halogen, or unsubstituted $C_1$ alkyl. In another embodiment of Formula (I), each of $R_7$, $R_8$, $R_9$, $R_{10}$, $R_{11}$, $R_{12}$, and $R_{13}$ is, independently, H or unsubstituted $C_1$ alkyl. In another embodiment of Formula (I), each of $R_7$, $R_8$, $R_9$, $R_{10}$, $R_{11}$, $R_{12}$, and $R_{13}$ is, independently, H or halogen. In another embodiment of Formula (I), each of $R_7$, $R_8$, $R_9$, $R_{10}$, $R_{11}$, $R_{12}$, and $R_{13}$ is H.

In another embodiment of Formula (I), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H. In another embodiment of Formula (I), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or halogen. In another embodiment of Formula (I), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(5- to 10-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(5- to 10-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(5- to 10-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$-(5- to 10-membered heteroaryl), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(5- to 7-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(5- to 7-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(5- to 7-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$-(5- to 7-membered heteroaryl), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(6-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(6-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(6-membered heteroaryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$-(6-membered heteroaryl), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(6-membered heteroaryl), n is 0, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(6-membered heteroaryl), n is 0, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(6-membered heteroaryl), n is 0, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$-(6-membered heteroaryl), n is 0, each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(6-membered heteroaryl), n is 1, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(6-membered heteroaryl), n is 1, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(6-membered heteroaryl), n is 1, each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$—($C_6$-$C_{10}$ aryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$—($C_6$-$C_{10}$ aryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$—($C_6$-$C_{10}$ aryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$—($C_6$-$C_{10}$ aryl), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$—($C_6$ aryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$—($C_6$ aryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$—($C_6$ aryl), each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$—($C_6$ aryl), each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$—($C_6$ aryl), n is 0, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$—($C_6$ aryl), n is 0, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$—($C_6$ aryl), n is 0, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$—($C_6$ aryl), n is 0, each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$—($C_6$ aryl), n is 1, each of $R_2$, $R_3$, $R_4$, $R_4$, and $R_6$, when present, is H, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$—($C_6$ aryl), n is 1, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$—($C_6$ aryl), n is 1, each of $R_2$, $R_3$, $R_4$, $R_5$, and $R_6$, when present, is H, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$—($C_6$ aryl), n is 1, each of $R_2$, $R_3$, $R_4$, $R_5$, and $R_6$, when present, is H and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(6-membered heteroaryl), n is 0, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(6-membered heteroaryl), n is 0, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(6-membered heteroaryl), n is 0, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$-(6-membered heteroaryl), n is 0, and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$-(6-membered heteroaryl), n is 1, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$-(6-membered heteroaryl), n is 1, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$-(6-membered heteroaryl), n is 1, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$-(6-membered heteroaryl), n is 1, and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$—($C_6$ aryl), n is 0, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$—($C_6$ aryl), n is 0, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$—($C_6$ aryl), n is 0, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$—($C_6$ aryl), n is 0, and each of $R_7$, $R_8$, $R_9$, $R_{10}$, $R_{11}$, $R_{12}$, and $R_{13}$ is H or fluorine.

In another embodiment of Formula (I), $R_1$ is $(CR_cR_d)_n$—($C_6$ aryl), n is 1, and each of $R_7$, $R_8$, $R_9$, $R_{10}$, $R_{11}$, $R_{12}$, and $R_{13}$ is H. In another embodiment of Formula (I), $R_1$ is $(CR_cR_d)_n$—($C_6$ aryl), n is 1, and each of $R_7$, $R_8$, $R_9$, $R_{10}$, $R_{11}$, $R_{12}$, and $R_{13}$ is H or unsubstituted $C_1$-$C_3$ alkyl. In another embodiment of Formula (I), $R_1$ is $(CR_cR_d)_n$—($C_6$ aryl), n is 1, and each of $R_7$, $R_8$, $R_9$, $R_{10}$, $R_{11}$, $R_{12}$, and $R_{13}$ is H or halogen. In another embodiment of Formula (I), $R_1$ is $(CR_cR_d)_n$—($C_6$ aryl), n is 1, and each of $R_7$, $R_8$, $R_9$, $R_{10}$, $R_{11}$, $R_{12}$, and $R_{13}$ is H or fluorine.

Each of the embodiments described herein with respect to compounds of Formula I also applies to compounds of Formula I-A.

Certain embodiments of compounds of Formula I-A or I, or pharmaceutically acceptable salts thereof, are shown below in Table 1. Compounds of Formula I-A or I, or pharmaceutically acceptable salts thereof, and compounds of Table 1, or pharmaceutically acceptable salts thereof, collectively or individually are sometimes referred to herein as "compounds of the invention" or "compounds provided herein"

TABLE 1

| Structure | Compound No. |
|---|---|
| (structure) | 1 |
| (structure) | 2 |
| (structure) | 3 |
| (structure) | 4 |
| (structure) | 5 |

TABLE 1-continued

| Structure | Compound No. |
|---|---|
| (structure) | 6 |
| (structure) | 7 |
| (structure) | 8 |
| (structure) | 9 |
| (structure) | 10 |
| (structure) | 11 |
| (structure) | 12 |
| (structure) | 13 |

TABLE 1-continued

| Structure | Compound No. |
|---|---|
| 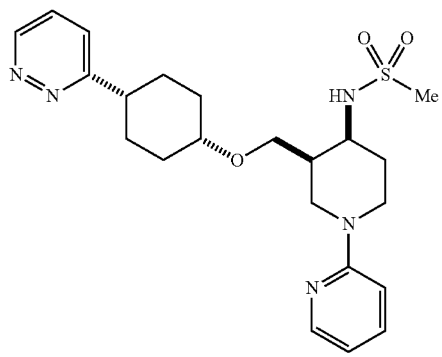 | 14 |
| 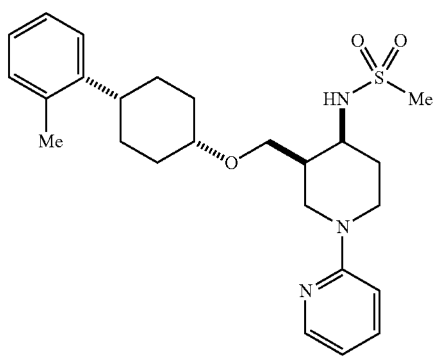 | 15 |
| 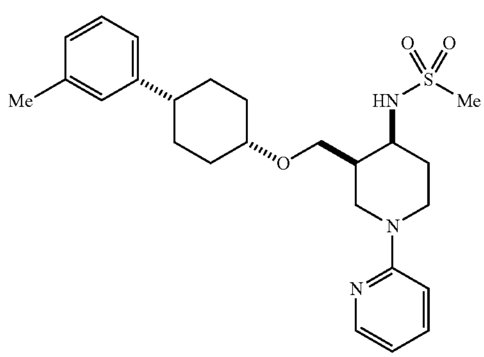 | 16 |
| 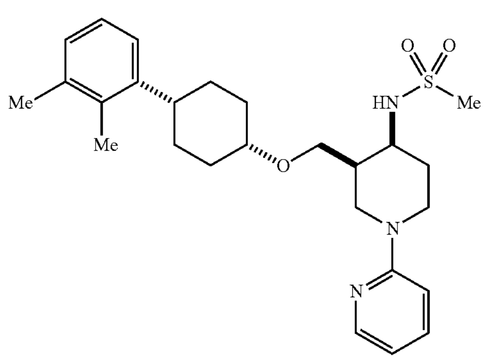 | 17 |
| | 18 |
| | 19 |
| | 20 |
| | 21 |

TABLE 1-continued

| Structure | Compound No. |
|---|---|
| (structure) | 22 |
| (structure) | 23 |
| (structure) | 24 |
| (structure) | 25 |
| (structure) | 26 |
| (structure) | 27 |
| (structure) | 28 |
| (structure) | 29 |

TABLE 1-continued

| Structure | Compound No. |
|---|---|
| (2-hydroxyphenyl-cyclohexyl-oxymethyl-piperidinyl-pyridinyl methanesulfonamide structure) | 30 |
| (3-hydroxyphenyl-cyclohexyl-oxymethyl-piperidinyl-pyridinyl methanesulfonamide structure) | 31 |
| (4-hydroxyphenyl-cyclohexyl-oxymethyl-piperidinyl-pyridinyl methanesulfonamide structure) | 32 |
| (3-trifluoromethylphenyl-cyclohexyl-oxymethyl-piperidinyl-pyridinyl methanesulfonamide structure) | 33 |
| (3-chlorophenyl-cyclohexyl-oxymethyl-piperidinyl-pyridinyl methanesulfonamide structure) | 34 |
| (3-cyanophenyl-cyclohexyl-oxymethyl-piperidinyl-pyridinyl methanesulfonamide structure) | 35 |
| (phenyl-cyclohexyl-oxymethyl-piperidinyl-benzyl methanesulfonamide structure) | 36 |
| (phenyl-cyclohexyl-oxymethyl-piperidinyl-(1-phenylethyl) methanesulfonamide structure) | 37 |

TABLE 1-continued

| Structure | Compound No. |
|---|---|
| (structure) | 38 |
| (structure) | 39 |
| (structure) | 40 |
| (structure) | 41 |
| (structure) | 42 |
| (structure) | 43 |
| (structure) | 44 |
| (structure) | 45 |

TABLE 1-continued

| Structure | Compound No. |
|---|---|
| 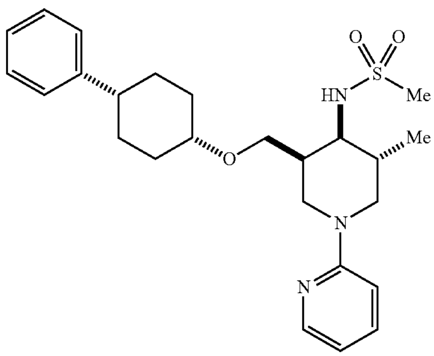 | 46 |
| 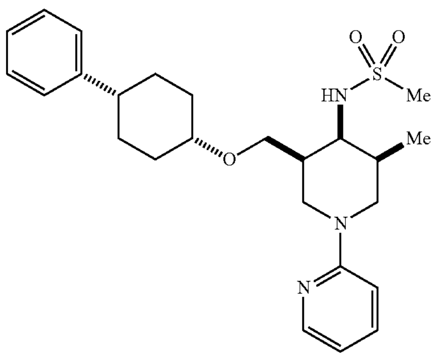 | 47 |
| 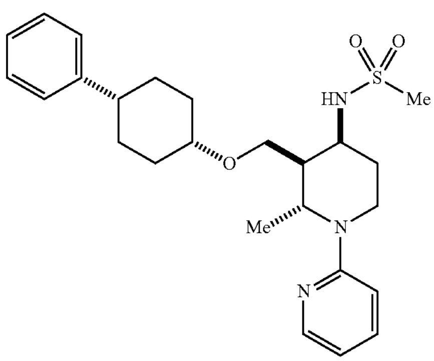 | 48 |
| 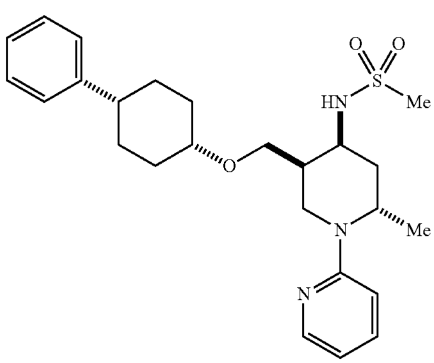 | 49 |
| | 50 |
| | 51 |
| | 52 |
| | 53 |

TABLE 1-continued

| Structure | Compound No. |
|---|---|
| 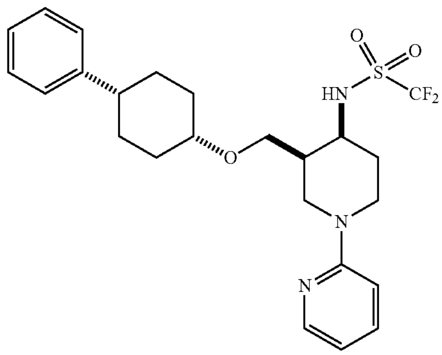 | 54 |
| 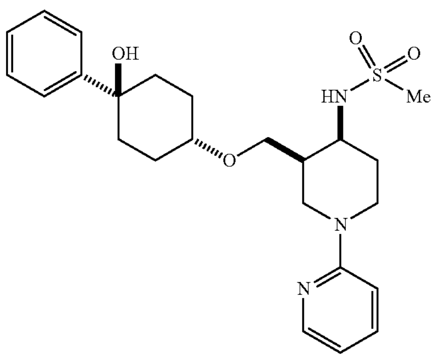 | 55 |
| 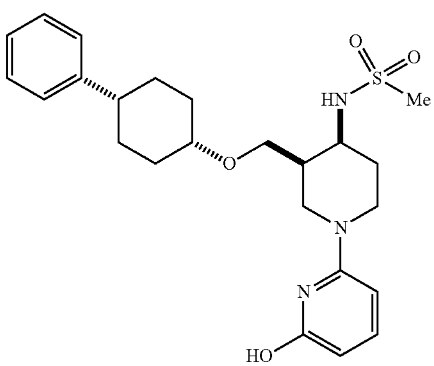 | 56 |
| 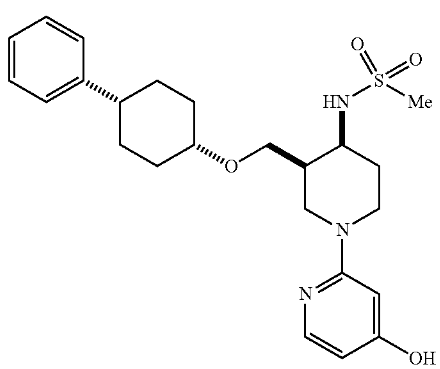 | 57 |
| | 58 |
| | 59 |
| | 60 |
| | 61 |

TABLE 1-continued

| Structure | Compound No. |
|---|---|
| (structure) | 62 |
| (structure) | 63 |
| (structure) | 64 |
| (structure) | 65 |
| (structure) | 66 |
| (structure) | 67 |
| (structure) | 68 |
| (structure) | 69 |

TABLE 1-continued

| Structure | Compound No. |
|---|---|
| [Structure of compound 70: a cyclohexyl group with phenyl substituent connected via O-CH2 to a piperidine ring (with N-phenyl) bearing an NH-SO2-Me group] | 70 |

The disclosed compounds possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of two or more isomers is utilized as the disclosed compound described herein. In another embodiment, a pure isomer is utilized as the disclosed compound described herein. In another embodiment, compounds described herein contain one or more chiral centers. These compounds are prepared by any means, including stereoselective synthesis, enantioselective synthesis or separation of a mixture of enantiomers or diastereomers. Resolution of compounds and isomers thereof is achieved by any means including, by way of non-limiting example, chemical processes, enzymatic processes, fractional crystallization, distillation, and chromatography.

In one embodiment, the disclosed compounds may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$ $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug or substrate tissue distribution studies. In another embodiment, substitution with heavier isotopes such as deuterium affords greater metabolic stability (for example, increased in vivo half-life or reduced dosage requirements). In another embodiment, the compounds described herein include a $^2H$ (i.e., deuterium) isotope.

In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

The specific compounds described herein, and other compounds encompassed by one or more of the Formulas described herein having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated by reference for such disclosure). General methods for the preparation of compounds as described herein are modified by the use of appropriate reagents and conditions, for the introduction of the various moieties found in the Formulas as provided herein.

Compounds described herein are synthesized using any suitable procedures starting from compounds that are available from commercial sources or are prepared using procedures described herein.

Methods of Treatment

The compounds of the invention can be used in a method of treating a disease or condition in a subject, said method comprising administering to the subject a compound of the invention, or a pharmaceutical composition comprising a compound of the invention. In one embodiment of the methods described herein, the subject is human. In one aspect, the compounds provided herein are useful in treatment of a disease or condition by acting as an agonist of the orexin-2 receptor.

The compounds of the invention can be used to treat a disease or condition selected from the group consisting of narcolepsy, cataplexy, or hypersomnia in a subject in need thereof.

In one embodiment, the compounds of the invention can be used to treat narcolepsy in a subject. In one embodiment, the compounds of the invention can be used to treat cataplexy in a subject. In one embodiment, the compounds of the invention can be used to treat hypersomnia in a subject.

Orexin-2 receptors are important in a wide range of biological functions. This suggests that orexin-2 receptors play a role in diverse disease processes in humans or other species. The compound of the present invention is useful for treating, preventing, or ameliorating the risk of one or more of the following symptoms or diseases of various neurological and psychiatric diseases associated with alterations in sleep/wake function. That is, narcolepsy, narcolepsy with cataplexy, idiopathic hypersomnia, hypersomnia, sleep apnea syndrome, narcolepsy syndrome, hypersomnolence syndrome characterized by hypersomnia (e.g., in subjects with Kleine Levin syndrome, major depression with hypersomnia, Lewy body dementia, Parkinson's disease, progressive supranuclear paralysis, Prader-Willi syndrome, Mobius syndrome, hypoventilation syndrome, Niemann-Pick disease type C, brain contusion, cerebral infarction, brain tumor, muscular dystrophy, multiple sclerosis, multiple systems atrophy, acute disseminated encephalomyelitis, Guillain-Barre syndrome, Rasmussen's encephalitis, Wernicke's encephalitis, limbic encephalitis, or Hashimoto's encephalopathy), coma, loss of consciousness, obesity (e.g., malignant mastocytosis, exogenous obesity, hyperinsulinar obesity, hyperplasmic obesity, hypop hyseal adiposity, hypoplasmic obesity, hypothyroid obesity, hypothalamic obesity, symptomatic obesity, infantile obesity, upper body obesity, alimentary obesity, hypogonadal obesity, systemic mastocytosis, simple obesity, or central obesity), insulin resistance syndrome, Alzheimer's disease, disturbance of consciousness such as coma and the like, side effects and complications due to anesthesia, sleep disturbance, excessive daytime sleepiness, sleep problem, insomnia, intermittent sleep, nocturnal myoclonus, REM sleep interruption, jet lag, jet lag syndrome, sleep disorder of alternating worker, sleep disorder, night terror, depression, major depression, sleepwalking disease, enuresis, sleep disorder, Alzheimer's dusk, sundowning, diseases associated with circadian rhythm, fibromyalgia, condition arising from decline in the quality of sleep, overeating, obsessive compulsive eating disorder, obesity-related disease, hypertension, diabetes, elevated plasma insulin concentration and insulin resistance, hyperlipidemia, hyperlipemia, endometrial cancer, breast cancer, prostate cancer, colorectal cancer, cancer, osteoarthritis, obstructive sleep apnea, cholelithiasis, gallstones, cardiac disease, abnormal heartbeat, arrhythmia, myocardial infarction, congestive cardiac failure, cardiac failure, coronary heart disease, cardiovascular disorder, polycysticovarian disease, craniopharingioma, Prader-Willi syndrome, Froelich's syndrome, growth hormone deficient, normal mutant short stature, Turner's syndrome, children suffering from acute lymphoblastic leukemia, syndrome X, reproductive hormone abnormality, declining fertility, infertility, male gonadal function decline, sexual and reproductive dysfunction such as female male hirsutism, fetal defects associated with pregnant women obesity, gastrointestinal motility disorders such as obesity-related gastroesophageal reflux, obesity hypoventilation syndrome (Pickwick syndrome), respiratory diseases such as dyspnea, inflammation such as systemic inflammation of the vascular system, arteriosclerosis, hypercholesterolemia, hyperuricemia, lower back pain, gall bladder disease, gout, kidney cancer, risk of secondary outcomes of obesity, such as lowering the risk of left ventricular hypertrophy, migraine pain, headache, neuropathic pain, Parkinson's disease, psychosis, autoimmune encephalitis, cancer related fatigue (such as excessive daytime sleepiness or fatigue associated with cancer and/or chemotherapy), cancer related nausea and vomiting, corticobasal degeneration, Huntington's disease, neuromyelitis optica, nociception, progressive supranuclear palsy, schizophrenia, systemic lupus erythematosus, traumatic brain injury, facial flushing, night sweats, diseases of the genital/urinary system, diseases related to sexual function or fertility, dysthymic disorder, bipolar disorder, bipolar I disorder, bipolar II disorder, cyclothymic disorder, acute stress disorder, agoraphobia, generalized anxiety disorder, obsessive disorder, panic attack, panic disorder, post-traumatic stress disorder (PTSD), separation anxiety disorder, social phobia, anxiety disorder, acute neurological and psychiatric disorders such as cardiac bypass surgery and post-transplant cerebral deficit, stroke, ischemic stroke, cerebral ischemia, spinal cord trauma, head trauma, perinatal hypoxia, cardiac arrest, hypoglycemic nerve injury, Huntington's chorea, amyotrophic lateral sclerosis, eye damage, retinopathy, cognitive impairment, muscle spasm, tremor, epilepsy, disorders associated with muscle spasticity, delirium, amnestic disorder, age-related cognitive decline, schizoaffective disorder, delusional disorder, drug addiction, dyskinesia, chronic fatigue syndrome, fatigue, medication-induced Parkinsonism syndrome, Jill-do La Tourette's syndrome, chorea, myoclonus, tic, restless legs syndrome, dystonia, dyskinesia, attention deficit hyperactivity disorder (ADHD), behavior disorder, urinary incontinence, withdrawal symptoms, trigeminal neuralgia, hearing loss, tinnitus, nerve damage, retinopathy, macular degeneration, vomiting, cerebral edema, pain, bone pain, arthralgia, toothache, cataplexy, and traumatic brain injury (TBI).

Particularly, the compound of the present invention is useful as a therapeutic or prophylactic drug for narcolepsy, idiopathic hypersomnia, hypersomnia, sleep apnea syndrome, narcolepsy syndrome, hypersomnolence syndrome characterized by hypersomnia (e.g., in Parkinson's disease, Guillain-Barre syndrome or Kleine Levin syndrome), Alzheimer's disease, obesity, insulin resistance syndrome, cardiac failure, diseases related to bone loss, sepsis, disturbance of consciousness such as coma and the like, side effects and complications due to anesthesia, and the like, or anesthetic antagonist.

In one embodiment, the compound of the present invention has orexin-2 receptor agonist activity and is useful as a prophylactic or therapeutic agent for narcolepsy.

In another embodiment, the compound of the present invention is useful as a prophylactic or therapeutic agent for narcolepsy type-1. In another embodiment, the compound of the present invention is useful as a prophylactic or therapeutic agent for narcolepsy type-2. In another embodiment, the compound of the present invention is useful as a prophylactic or therapeutic agent for narcolepsy and excessive daytime sleepiness. In another embodiment, the compound of the present invention is useful as a prophylactic or therapeutic agent for narcolepsy, cataplexy, and excessive daytime sleepiness. In another embodiment, the compound of the present invention is useful as a prophylactic or therapeutic agent for narcolepsy and cataplexy. In another embodiment, the compound of the present invention is useful as a prophylactic or therapeutic agent for excessive daytime sleepiness. In another embodiment, the compound of the present invention is useful as a prophylactic or therapeutic agent for idiopathic hypersomnia. In another embodiment, the compound of the present invention is useful as a prophylactic or therapeutic agent for obstructive sleep apnea.

In another embodiment, the compound of the present invention has orexin-2 receptor agonist activity and is useful as a prophylactic or therapeutic agent for hypersomnia in Parkinson's disease.

In another embodiment, the compound of the present invention has orexin-2 receptor agonist activity and is useful as a prophylactic or therapeutic agent for hypersomnia. In another embodiment, the compound of the present invention has orexin-2 receptor agonist activity and is useful as a prophylactic or therapeutic agent for excessive daytime sleepiness associated with Parkinson's disease.

In another embodiment, the compound of the present invention has orexin-2 receptor agonist activity, and is useful as a prophylactic or therapeutic agent for excessive daytime sleepiness or fatigue associated with cancer and/or chemotherapy.

In another embodiment, the present invention provides a method of treating narcolepsy in a subject in need thereof comprising administering to the subject a compound of Formula I-A or I, or a pharmaceutically acceptable salt thereof.

In another embodiment, the present invention provides a method of treating narcolepsy type-1 in a subject in need thereof comprising administering to the subject a compound of Formula I-A or I, or a pharmaceutically acceptable salt thereof.

In another embodiment, the present invention provides a method of treating narcolepsy type-2 in a subject in need thereof comprising administering to the subject a compound of Formula I-A or I, or a pharmaceutically acceptable salt thereof.

In another embodiment, the present invention provides a method of treating narcolepsy and excessive daytime sleepiness in a subject in need thereof comprising administering to the subject a compound of Formula I-A or I, or a pharmaceutically acceptable salt thereof.

In another embodiment, the present invention provides a method of treating narcolepsy, cataplexy, and excessive daytime sleepiness in a subject in need thereof comprising administering to the subject a compound of Formula I-A or I, or a pharmaceutically acceptable salt thereof.

In another embodiment, the present invention provides a method of treating narcolepsy and cataplexy in a subject in need thereof comprising administering to the subject a compound of Formula I-A or I, or a pharmaceutically acceptable salt thereof.

In another embodiment, the present invention provides a method of treating excessive daytime sleepiness in a subject in need thereof comprising administering to the subject a compound of Formula I-A or I, or a pharmaceutically acceptable salt thereof.

In another embodiment, the present invention provides a method of treating idiopathic hypersomnia in a subject in need thereof comprising administering to the subject a compound of Formula I-A or I, or a pharmaceutically acceptable salt thereof.

In another embodiment, the present invention provides a method of treating excessive daytime sleepiness and idiopathic hypersomnia in a subject in need thereof comprising administering to the subject a compound of Formula I-A or I, or a pharmaceutically acceptable salt thereof.

In another embodiment, the present invention provides a method of treating obstructive sleep apnea in a subject in need thereof comprising administering to the subject a compound of Formula I-A or I, or a pharmaceutically acceptable salt thereof.

In another embodiment, the present invention provides a method of treating excessive daytime sleepiness and obstructive sleep apnea in a subject in need thereof comprising administering to the subject a compound of Formula I-A or I, or a pharmaceutically acceptable salt thereof.

In any of the methods as described herein, the subject is administered a compound of Formula I-A. In any of the methods as described herein, the subject is administered a compound of Formula I.

Each of the embodiments described herein with respect to the use of compounds of Formula I also applies to compounds of Formula I-A.

In any of the compositions or methods as described herein, the compound of Formula I-A or I, or a pharmaceutically acceptable salt thereof, is present and/or administered in a therapeutically effective amount.

Administration/Dosage/Formulations

In another aspect, provided herein is a pharmaceutical composition comprising at least one compound of the invention, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could begin administration of the pharmaceutical composition to dose the disclosed compound at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of the disclosed compound calculated to produce the desired therapeutic effect in association with the required pharmaceutical vehicle. The dosage unit forms of the invention are dictated by and directly dependent on (a) the unique characteristics of the disclosed compound and the particular therapeutic effect to be achieved, and (b) the limitations inherent in the art of compounding/formulating such a disclosed compound for the treatment of narcolepsy or cataplexy in a patient.

In one embodiment, the compounds of the invention are formulated using one or more pharmaceutically acceptable excipients or carriers. In one embodiment, the pharmaceutical compositions of the invention comprise a therapeutically effective amount of a disclosed compound and a pharmaceutically acceptable carrier.

In some embodiments, the dose of a disclosed compound is from about 1 mg to about 1,000 mg. In some embodiments, a dose of a disclosed compound used in compositions described herein is less than about 1,000 mg, or less than about 800 mg, or less than about 600 mg, or less than about 500 mg, or less than about 300 mg, or less than about 200 mg, or less than about 100 mg, or less than about 50 mg, or less than about 20 mg, or less than about 10 mg. For example, a dose is about 10 mg, 20 mg, 25 mg, 30 mg, 40 mg, 50 mg, 60 mg, 70 mg, 80 mg, 90 mg, 100 mg, 120 mg, 140 mg, 160 mg, 180 mg, 200 mg, 220 mg, 240, 260 mg, 280 mg, 300 mg, 350 mg, 400 mg, 450 mg, 500 mg, 550 mg, or about 600 mg.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration. In one embodiment, the preferred route of administration is oral.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the disclosed compounds may be formulated for injection or infusion, for example, intravenous, intramuscular or subcutaneous injection or infusion, or for administration in a bolus dose or continuous infusion. Suspensions, solutions or emulsions in an oily or aqueous vehicle, optionally containing other formulatory agents such as suspending, stabilizing or dispersing agents may be used.

Those skilled in the art will recognize or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is further illustrated by the following examples, which should not be construed as further limiting. The practice of the present invention will employ, unless otherwise indicated, conventional techniques of organic synthesis, cell biology, cell culture, molecular biology, transgenic biology, microbiology and immunology, which are within the skill of the art.

General Procedures

Example 1: Synthesis Procedures

Synthesis procedures for preparation of the compounds of the invention are readily available to the ordinary skilled artisan. Unless otherwise indicated, starting materials were generally obtained from commercial sources.

The following abbreviations are used in the synthetic examples below:

DCM=dichloromethane
MsCl=methanesulfonyl chloride
MeOH=methanol
THF=tetrahydrofuran
EtOH=ethanol
DIPEA=N,N-diisopropylethylamine
ACN or MeCN=acetonitrile
NEt$_3$ or TEA=triethylamine
PE=petroleum ether
EtOAc=ethyl acetate
TFA=trifluoroacetic acid
min=minutes
hr=hours
NaH=sodium hydride
DMSO=dimethyl sulfoxide
TMSCl=trimethylsilyl chloride
Pd/C=palladium on carbon
Ms=methanesulfonyl
Bn=benzyl
Ph=phenyl
LiHMDS=lithium bis(trimethylsilyl)amide
Pd(OH)$_2$/C=Palladium hydroxide on carbon
DMAP=4-(dimethylamino)pyridine
KOAc=potassium acetate
Pd(dppf)Cl$_2$=[1,1'-bis(diphenylphosphino)ferrocene]dichloropalladium(II)
Pd(PPh$_3$)$_4$=tetrakis(triphenylphosphine)palladium(0)

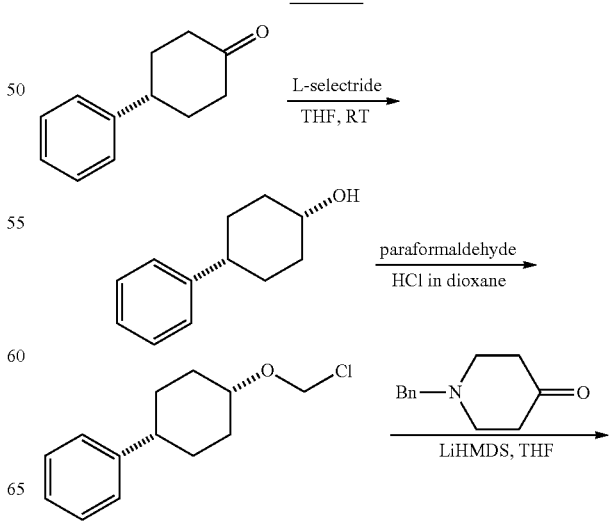

Scheme 1

49
-continued
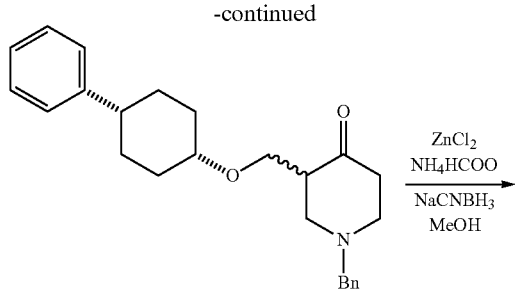
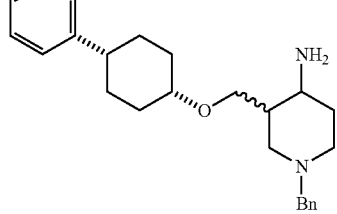
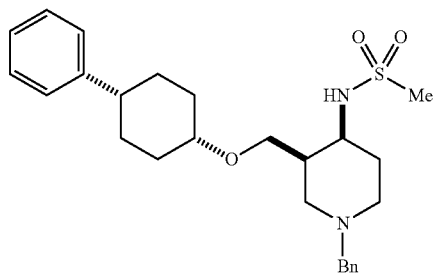
50
-continued
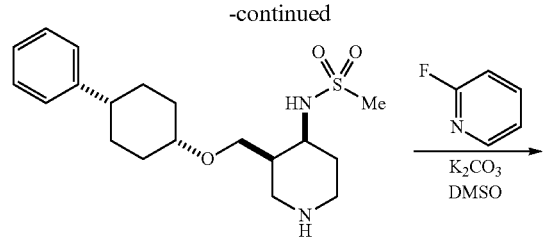
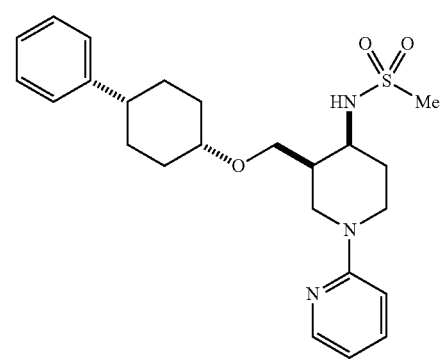
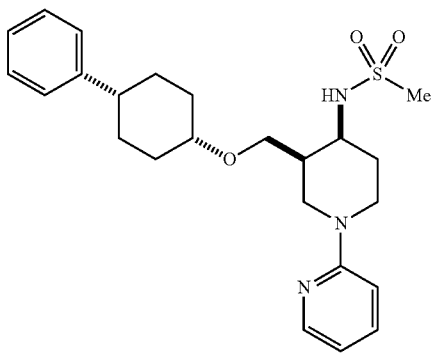

Scheme 2
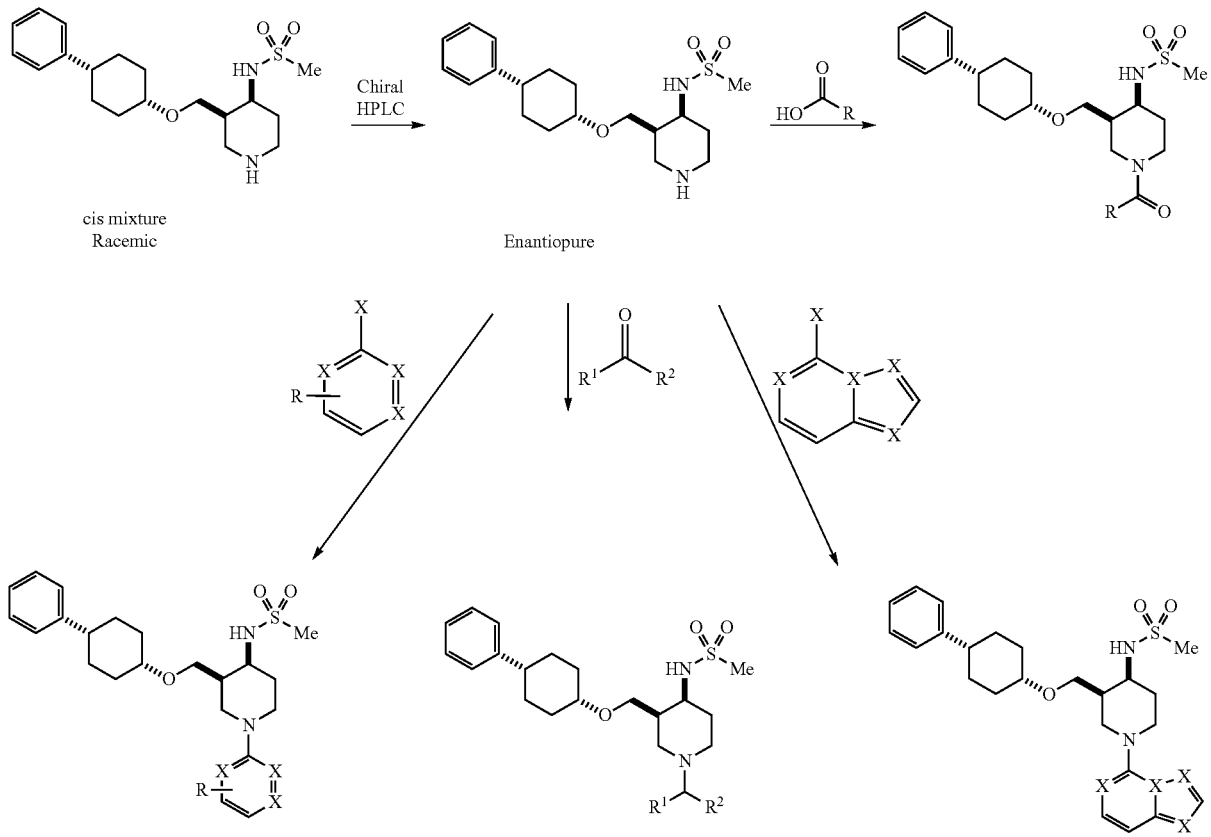
Scheme 3.
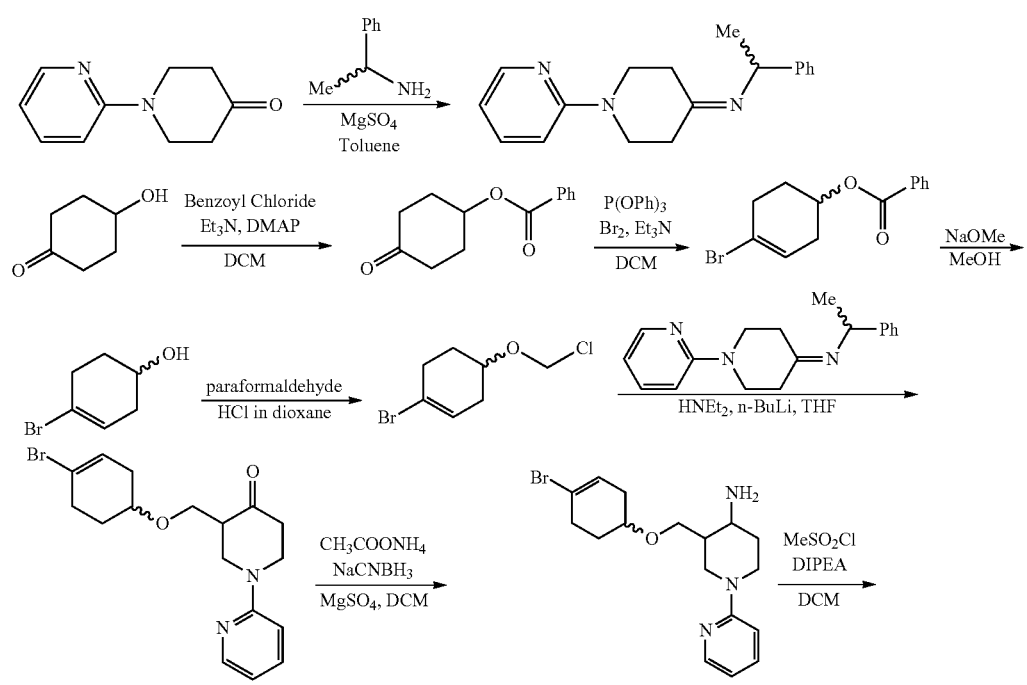

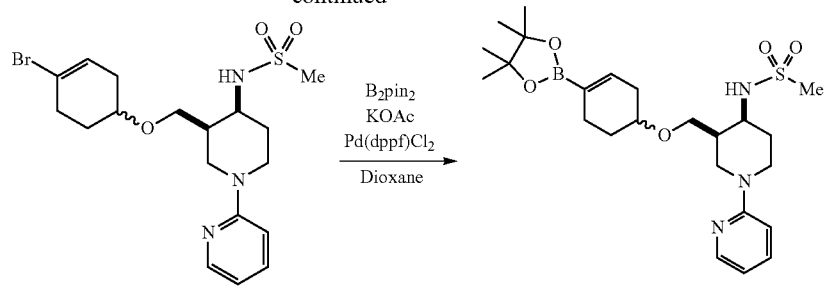
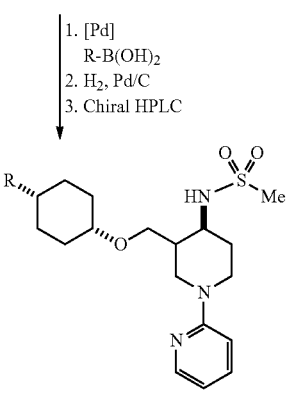 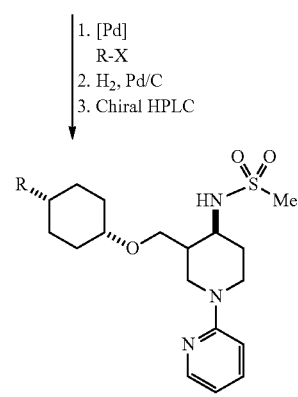
Scheme 4.
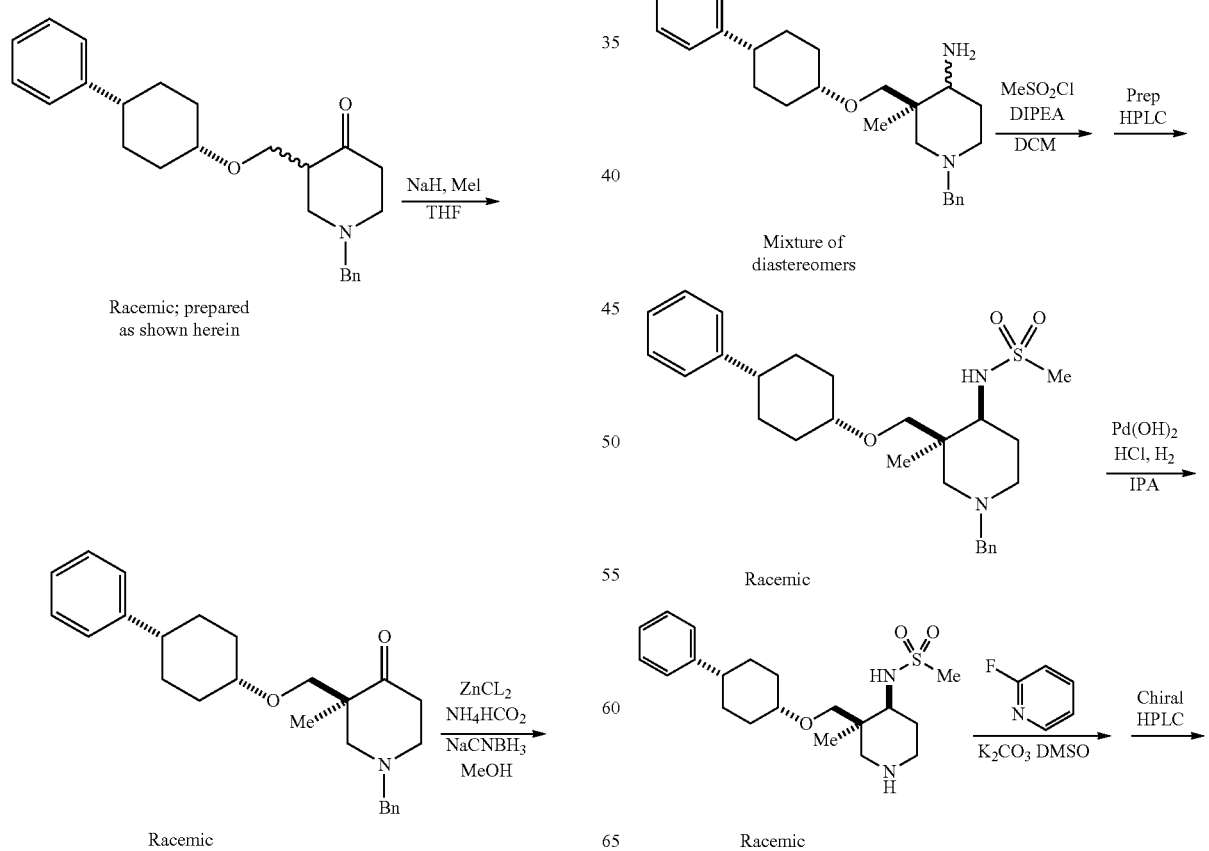

-continued

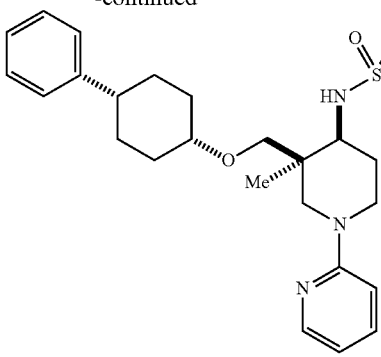

Example 1.1

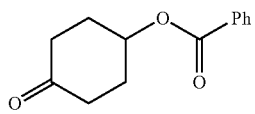

To a stirred solution of 4-hydroxycyclohexan-1-one (2.00 g, 17.5 mmol, 1.00 equiv.) and benzoyl chloride (2.46 g, 17.522 mmol, 1.00 equiv.) in DCM (50.00 mL) was added triethylamine (2.66 g, 26.3 mmol, 1.50 equiv.) and DMAP (214.06 mg, 1.752 mmol, 0.10 equiv.) dropwise at 0 degrees C. The resulting mixture was stirred for two hours at room temperature. To the above mixture was added benzoyl chloride (1.23 g, 8.761 mmol, 0.50 equiv.) dropwise at room temperature. The resulting mixture was stirred for an additional three hours at room temperature. When the reaction was complete by TLC, the crude mixture was diluted with water. The aqueous layer was extracted with DCM (3×50 mL). The combined organic layers were dried over anhydrous MgSO₄. The residue was purified by silica gel chromatography, eluting with PE/EtOAc (4:1) to afford 4-oxocyclohexyl benzoate (3.37 g, 88.12% yield) as a solid.

LCMS: m/z (ES+), [M+H]+=219.65.

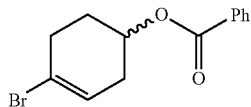

To a stirred solution of P(OPh)₃ (7.82 g, 25.2 mmol, 1.10 equiv.) in DCM (70.00 mL) was added Br₂ (1.41 mL, 8.81 mmol, 1.20 equiv.) dropwise at −60 degrees C. under nitrogen atmosphere. 30 minutes later, to the above mixture was added NEt₃ (4.14 mL, 40.9 mmol, 1.30 equiv.) and 4-oxocyclohexyl benzoate (5.00 g, 22.9 mmol, 1.00 equiv.) at −60 degrees C. The resulting mixture was stirred for 18 hr at room temperature. The reaction was quenched by the addition of saturated aqueous NaSO₃ (aqueous, 20 mL) at 0 degrees C. The resulting mixture was extracted with DCM (3×50 mL). The combined organic layers were washed with brine (2×50 mL), dried over anhydrous Na₂SO₄. After filtration, the filtrate was concentrated under reduced pressure. The residue was purified by silica gel column chromatography, eluted with PE/EtOAc (20:1) to afford 4-bromocyclohex-3-en-1-yl benzoate (5.8 g, 90.05%) as a solid in racemic form. LCMS: m/z (ES+), [M+H]+=282.15.

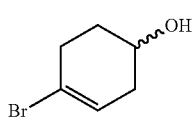

A solution of racemic 4-bromocyclohex-3-en-1-yl benzoate (3.00 g, 10.7 mmol, 1.00 equiv.) and sodium methoxide (634.11 mg, 11.738 mmol, 1.10 equiv.) in MeOH (30 mL) was stirred overnight at room temperature under nitrogen atmosphere. Desired product could be detected by TLC. The reaction was quenched with water (20 mL) at room temperature. The resulting mixture was extracted with DCM (4×50 mL). The combined organic layers were washed with water (3×30 mL), dried over anhydrous Na₂SO₄. After filtration, the filtrate was concentrated under reduced pressure. The residue was purified by silica gel column chromatography, eluted with PE/EtOAc (4:1) to afford 4-bromocyclohex-3-en-1-ol (1.7 grams, 90% yield) as an oil.

¹H-NMR (400 MHz, Chloroform-d) δ 5.94 (d, 1H), 4.08-3.95 (m, 1H), 2.68-2.32 (m, 3H), 2.23-1.74 (m, 3H).

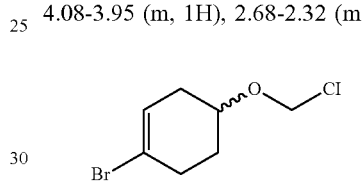

A solution of 4-bromocyclohex-3-en-1-ol (6.50 grams, 36.7 mmol, 1.00 equiv.) and paraformaldehyde (1.65 grams, 55.1 mmol, 1.50 equiv.) in TMSCl (19.5 mL, 180 mmol, 4.16 equiv.) was stirred overnight at room temperature under nitrogen atmosphere. Desired product could be detected by TLC. The resulting mixture was filtered, and the filter cake was washed with THF (3×10 mL). The filtrate was concentrated under reduced pressure, and the resulting crude product was used directly in the next step without purification.

¹H-NMR (400 MHz, Chloroform-d) δ 6.00-5.85 (m, 1H), 5.57 (s, 2H), 4.11 (d, 1H), 2.73-2.35 (m, 3H), 2.31-2.13 (m, 1H), 2.03-1.81 (m, 2H).

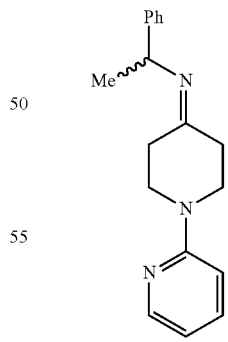

To a stirred mixture of 1-(pyridine-2-yl)piperidin-4-one (5.00 grams, 28.4 mmol, 1.00 equiv.) and MgSO₄ (10.25 grams, 85.12 mmol, 3.00 equiv.) in toluene (75 mL) was added racemic methylbenzylamine (3.44 grams, 28.4 mmol, 1.00 equiv.) dropwise at room temperature under nitrogen atmosphere. The resulting mixture was stirred overnight at room temperature under nitrogen atmosphere. Then, the crude reaction was filtered, and the filter cake was washed with toluene (2×20 mL). The filtrate was concentrated under reduced pressure. The resulting crude product was used directly in the next step without purification. Desired product could be detected by TLC.

¹H-NMR (400 MHz, Chloroform-d) δ 8.26-8.14 (m, 1H), 7.57-7.41 (m, 1H), 7.42-7.15 (m, 6H), 6.74-6.53 (m, 2H), 4.76 (q, 1H), 3.98-3.88 (m, 1H), 3.87-3.63 (m, 3H), 2.75-2.57 (m, 2H), 2.58-2.27 (m, 2H), 1.73 (s, 1H), 1.47 (dd, 3H).

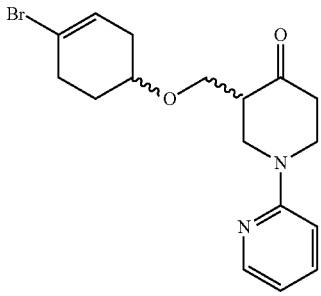 [SMILES: O=C1CCN(c2ccccn2)CC1COC1CC=C(Br)CC1]

To a stirred solution of diethylamine (2.45 grams, 33.5 mmol, 1.20 equiv.) in tetrahydrofuran (30 mL) was added n-butyllithium (13.4 mL, 33.5 mmol, 1.20 equiv.) dropwise at −78 degrees C. under nitrogen atmosphere. The resulting mixture was stirred for 30 minutes at −78 degrees C. under nitrogen atmosphere. To the above mixture was added the imine (1S)-1-phenyl-N-[1-(pyridine-2-yl)piperidine-4-ylidene]ethanamine (7.80 grams, 27.9 mmol, 1.00 equiv.) in THF (20 mL) dropwise over 15 minutes at −78 degrees C. The resulting mixture was stirred for an additional one hour. To the above mixture was added 1-bromo-4-(chloromethoxy)cyclohex-1-ene (7.56 grams, 33.5 mmol, 1.20 equiv.) in THF (20 mL) dropwise over 15 minutes at −78 degrees C. The resulting mixture was stirred for an additional one hour. Then, the reaction was quenched by the addition of sodium phosphate buffer (200 mL, 10% aqueous) and stirred for one hour.

The resulting mixture was extracted with DCM. The combined organic layers were washed with brine and dried over anhydrous MgSO₄. After filtration, the filtrate was concentrated under reduced pressure. The residue was purified by silica gel column chromatography, eluting with PE/EtOAc (4:1) to afford 3-[[(4-bromocyclohex-3-en-1-yl)oxy]methyl]-1-(pyridine-2-yl)piperidine-4-one (3 grams, 29% yield) as an oil.

LCMS: m/z (ES+), [M+H]+=366.27.

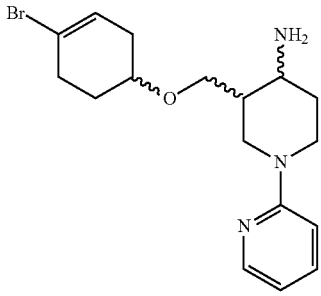 [SMILES: NC1CCN(c2ccccn2)CC1COC1CC=C(Br)CC1]

To a stirred solution of 3-[[(4-bromocyclohex-3-en-1-yl)oxy]methyl]-1-(pyridine-2-yl)piperidin-4-one (5.20 grams, 14.2 mmol, 1.00 equiv.) in methanol (40 mL) was added ZnCl₂ (2.85 mL, 1.99 mmol, 0.14 equiv.) dropwise at room temperature under nitrogen atmosphere. The reaction mixture was irradiated with microwave radiation for 30 minutes at room temperature. To the above mixture was added HCOONH₄ (13.46 grams, 213.5 mmol, 15.00 equiv.) at room temperature. The resulting mixture was stirred for an additional one hour at room temperature. To the above mixture was added ZnCl₂ (2.85 mL, 1.99 mmol, 0.14 equiv.) at 0 degrees C. The resulting mixture was stirred for an additional two days at room temperature. The reaction was then quenched by the addition of water (20 mL) at room temperature. The mixture was then extracted with DCM (3×100 mL), and the combined organics layers were washed with brine (2×50 mL) and dried over anhydrous Na₂SO₄. After filtration, the filtrate was concentrated under reduced pressure. The residue was purified by silica gel chromatography, eluting with DCM/MeOH (6:1) to afford 3-[[(4-bromocyclohex-3-en-1-yl)oxy]methyl]-1-(pyridine-2-yl)piperidine-4-amine (3.7 grams, 71% yield) as an oil.

LCMS: m/z (ES+), [M+H]+=367.30.

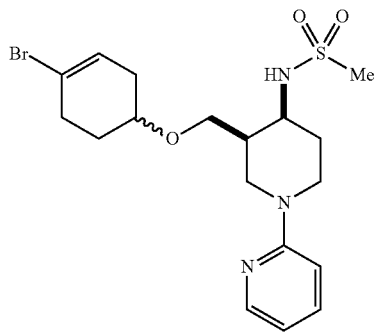

To a stirred solution of 3-[[(4-bromocyclohex-3-en-1-yl)oxy]methyl]-1-(pyridin-2-yl)piperidin-4-amine (1.90 grams, 5.187 mmol, 1.00 equiv.) and diisopropylethylamine (2.01 grams, 15.6 mmol, 3.00 equiv.) in DCM (30 mL) was added methanesulfonyl chloride (0.89 grams, 7.78 mmol, 1.50 equiv.) dropwise at room temperature under nitrogen atmosphere. The resulting mixture was stirred for 30 minutes at room temperature under nitrogen atmosphere. The crude residue was purified by silica gel column chromatography, eluting with PE/EtOAc (1:1) to afford N-[3-([[(1R)-4-bromocyclohex-3-en-1-yl]oxy]methyl)-1-(pyridin-2-yl)piperidin-4-yl]methanesulfonamide (1.3 grams, 65% yield) as an oil. This product was then purified by Prep-HPLC with the following conditions (Column: DAICEL DCpak® (Daicel Corporation, Osaka, Japan) P4VP, 20 mm*250 mm, 5um; Mobile Phase A: CO₂, Mobile Phase B: ACN/MeOH=4:1 (0.1% 2M NH₃-MeOH); Flow rate: 50 mL/min; Gradient: 25% B; 254 nm) to afford N-[3-([[(1R)-4-bromocyclohex-3-en-1-yl]oxy]methyl)-1-(pyridin-2-yl)piperidin-4-yl]methanesulfonamide (375 mg, 18.8% yield) as an oil.

LCMS: m/z (ES+), [M+H]+=445.39.

¹H-NMR (400 MHz, Chloroform-d) δ 8.23-8.08 (m, 1H), 7.50 (dd, 1H), 6.80-6.54 (m, 2H), 5.92 (dt, 1H), 5.11 (dd, 1H), 4.46-4.17 (m, 2H), 3.79-3.61 (m, 3H), 3.61-3.43 (m, 2H), 3.02 (d, 3H), 2.93 (t, 1H), 2.74 (dt, 1H), 2.61-2.47 (m, 2H), 2.47-2.32 (m, 1H), 2.27 (d, 1H), 2.16 (dt, 1H), 2.04-1.91 (m, 1H), 1.84 (d, 2H), 1.68-1.54 (m, 1H).

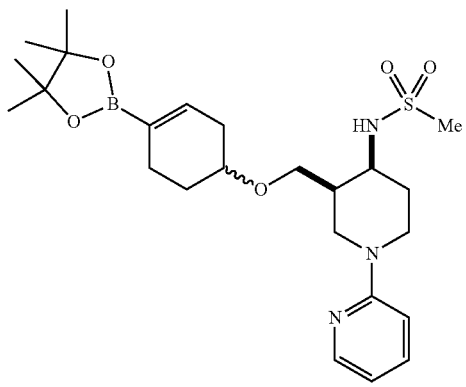 [SMILES: CC1(C)OB(C2=CCC(OC[C@@H]3CN(c4ccccn4)CC[C@@H]3NS(C)(=O)=O)CC2)OC1(C)C]

To a stirred solution of N-(3-[[(4-bromocyclohex-3-en-1-yl)oxy]methyl]-1-(pyridin-2-yl)piperidin-4-yl)methanesulfonamide (1.00 grams, 2.25 mmol, 1.00 equiv.) and bis(pinacolato)diboron (857.15 mg, 3.375 mmol, 1.50 equiv.) in dioxane was added KOAc (0.66 grams, 6.751 mmol, 3.00 equiv.) at room temperature under air atmosphere. To the above mixture was added Pd(dppf)Cl$_2$ (0.16 grams, 0.225 mmol, 0.10 equiv.) at room temperature. The resulting mixture was stirred for 4 hr at 100 degrees C. under nitrogen atmosphere. The resulting crude product was extracted with EtOAc (3×50 mL). The combined organic layers were washed with brine (20 mL) and dried over anhydrous Na$_2$SO$_4$. After filtration, the filtrate was concentrated under reduced pressure. The residue was purified by silica gel column chromatography, eluting with PE/EtOAc (1:1) to afford N-[1-(pyridin-2-yl)-3-([[(1R)-4-(4,4,5,5-tetramethyl-1,3,2-dioxaborolan-2-yl)cyclohex-3-en-1-yl]oxy]methyl)piperidin-4-yl]methanesulfonamide (1.0 grams, 90% yield) as a solid.

LCMS(E07880-030): m/z (ES+), [M+H]+=492.45.

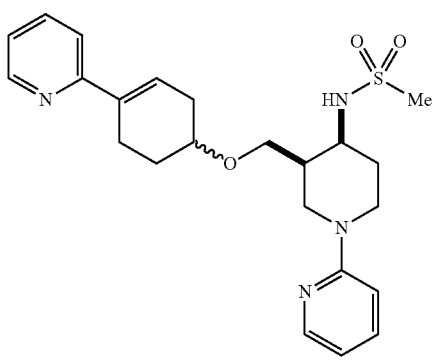 [SMILES: CS(=O)(=O)N[C@H]1CCN(c2ccccn2)C[C@H]1COC1CC=C(c2ccccn2)CC1]

To a stirred solution of N-(3-[[(4-bromocyclohex-3-en-1-yl)oxy]methyl]-1-(pyridin-2-yl)piperidin-4-yl)methanesulfonamide (200.0 mg, 0.450 mmol, 1.00 equiv.) and 2-bromopyridine (71.1 mg, 0.450 mmol, 1.00 equiv.) in 1,4-dioxane (5 mL) and water (1 mL) were added Cs$_2$CO$_3$ (366.6 mg, 1.125 mmol, 2.50 equiv.) and Pd(PPh$_3$)$_4$ (52.0 mg, 0.045 mmol, 0.10 equiv.) at room temperature under nitrogen atmosphere. The resulting mixture was stirred overnight at 80 degrees C. under nitrogen atmosphere. The resulting residue was purified by Prep-TLC (EtOAc) to afford N-[1-(pyridin-2-yl)-3-([[4-(pyridin-2-yl)cyclohex-3-en-1-yl]oxy]methyl)piperidin-4-yl]methanesulfonamide (170 mg, 85.4% yield) as an oil.

LCMS: m/z (ES+), [M+H]+=443.58.

(Compound 2)

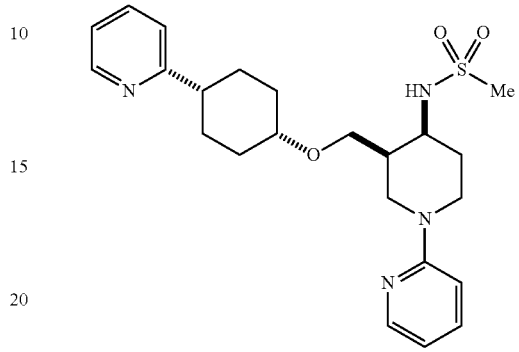

To a room temperature, stirred solution of N-[1-(pyridin-2-yl)-3-([[4-(pyridin-2-yl)cyclohex-3-en-1-yl]oxy]methyl)piperidin-4-yl]methanesulfonamide (150.0 mg, 0.339 mmol, 1.00 equiv.) in MeOH (10 mL) was added Pd/C (72.1 mg, 0.0678 mmol, 2.00 equiv.). The atmosphere was exchanged for hydrogen, and the resulting mixture was stirred for two hours at room temperature under hydrogen atmosphere. The resulting mixture was filtered, and the filter cake was washed with methanol (3×20 mL). The filtrate was concentrated under reduced pressure. The residue was purified by reverse flash chromatography with the following conditions: column, C18 silica gel; mobile phase, MeCN in TFA/water, 0% to 20% gradient over 30 minutes; detector, UV 254 nm. This resulted in the product N-[1-(pyridin-2-yl)-3-([[4-(pyridin-2-yl)cyclohexyl]oxy]methyl)piperidin-4-yl]methanesulfonamide (60 mg, 40% yield) as an oil as a mixture of isomers.

LCMS: m/z (ES+), [M+H]+=445.59.

This mixture of isomers (60 mg) was purified further by CHIRAL-Prep-HPLC with the following conditions (Column: CHIRALPAK® (Daicel Corporation, Osaka, Japan) IE, 2 cm*25 cm, 5 um; Mobile Phase A: Hexanes (with 0.2% diethylamine); Mobile Phase B: IPA; Flow rate: 20 mL/min; Isocratic 40% B over 25 min; Detector: 220/254 nm) to afford N-[(3R,4S)-1-(pyridin-2-yl)-3-([[(1s,4s)-4-(pyridin-2-yl)cyclohexyl]oxy]methyl)piperidin-4-yl]methanesulfonamide (15.8 mg, 26.33%) as a solid.

LCMS(E07273-129): m/z (ES+), [M+H]+=445.59.

$^1$H-NMR (400 MHz, Methanol-d$_4$) δ 8.43 (d, 1H), 8.06 (dd, 1H), 7.78 (d, 1H), 7.52 (d, 1H), 7.35 (dt, 1H), 7.25 (d, 1H), 6.92-6.84 (m, 1H), 6.63 (d, 1H), 3.87 (dq, 2H), 3.75 (dd, 1H), 3.71-3.60 (m, 2H), 3.59-3.52 (m, 2H), 3.47 (dd, 1H), 3.05 (s, 3H), 2.76 (t, 1H), 2.29 (dt, 1H), 2.09 (d, 2H), 2.00-1.80 (m, 4H), 1.75-1.52 (m, 4H).

Example 1.2

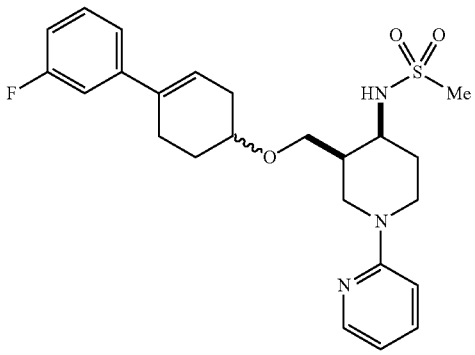

Into a 20 mL sealed tube were added N-(3-[[(4-bromocyclohex-3-en-1-yl)oxy]methyl]-1-(pyridin-2-yl)piperidin-4-yl)methanesulfonamide (200.00 mg, 0.450 mmol, 1.00 equiv.), Na₂CO₃ (143.10 mg, 1.350 mmol, 3.00 equiv.), 3-fluorophenylboronic acid (94.46 mg, 0.675 mmol, 1.50 equiv.), dioxane (4.00 mL), water (1.00 mL) and Pd(dppf)Cl₂ (19.76 mg, 0.027 mmol, 0.06 equiv.) at room temperature. The resulting mixture was stirred for two hours at 80 degrees C. under nitrogen atmosphere. The aqueous layer was extracted with EtOAc (1×10 mL). The resulting mixture was concentrated under reduced pressure, and the crude product was purified by reverse flash chromatography with the following conditions: column, C18 silica gel; mobile phase: ACN water, 10% to 60% gradient over 20 minutes; detector, UV 254 nm. This resulted in N-[3-([[4-(3-fluorophenyl)cyclohex-3-en-1-yl]oxy]methyl)-1-(pyridin-2-yl)piperidin-4-yl]methanesulfonamide (200 mg, 96.7% yield) as a solid.

LCMS: m/z (ES+), [M+H]+=460.

(Compound 6)

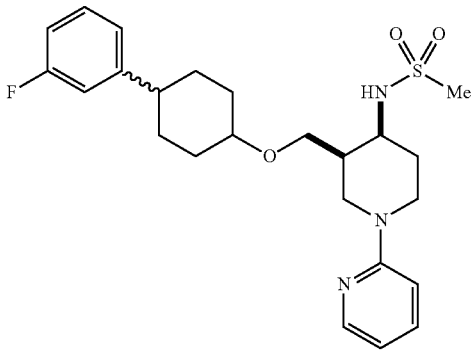

A solution/mixture of N-[3-([[4-(3-fluorophenyl)cyclohex-3-en-1-yl]oxy]methyl)-1-(pyridin-2-yl)piperidin-4-yl]methanesulfonamide (187 mg, 0.407 mmol, 1.00 equiv.) and Pd/C (49.8 mg, 0.468 mmol, 1.15 equiv.) in ethyl acetate (15.0 mL) was stirred for two hours at room temperature under hydrogen atmosphere. Desired product could be detected by LCMS. The resulting mixture was filtered, and the filter cake was washed with EtOAc (3×10 mL). The filtrate was concentrated under reduced pressure. The residue was purified by reverse phase chromatography with the following conditions: column, C18 silica gel; mobile phase, ACN in water; 10% to 60% gradient over 20 minutes; detector, UV 254 nm. This resulted in N-[3-([[4-(3-fluorophenyl)cyclohexyl]oxy]methyl)-1-(pyridin-2-yl)piperidin-4-yl]methanesulfonamide (97 mg, 52% yield) as a solid as a mixture of isomers.

LCMS: m/z (ES+), [M+H]+=462.

This mixture of isomers (97 mg) was purified by Prep-CHIRAL-HPLC with the following conditions: column, CHIRALPAK® IE, 2*25 cm, 5um; mobile phase A: hexanes with 0.2% diethylamine; mobile phase B, ethanol; flow rate, 20 mL/min; isocratic 35% B over 15.5 min; detector, 220/254 nm. This afforded N-[(3R,4S)-1-(pyridin-2-yl)-3-([[(1s,4s)-4-(3-fluorophenyl)cyclohexyl]oxy]methyl)piperidin-4-yl]methanesulfonamide (20.7 mg, 21.34%) as a solid.

LCMS: m/z (ES+), [M+H]+=462.

¹H-NMR (400 MHz, MeOD) δ 1.56 (m, 1H), 1.61 (m, 3H), 1.77 (m, 1H), 1.88 (m, 3H), 2.06 (m, 2H), 2.30 (dt, 1H), 2.58 (m, 1H), 3.05 (s, 3H), 3.46 (dt, 1H), 3.56 (m, 2H), 3.64 (m, 2H), 3.76 (m, 1H), 3.86 (m, 2H), 6.64 (ddd, 1H), 6.88 (m, 2H), 6.97 (dt, 1H), 7.05 (dt, 1H), 7.27 (m, 1H), 7.52 (ddd, 1H), 8.07 (ddd, 1H).

Example 1.3

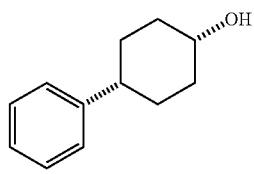

Into a 500 mL 3-necked round-bottom flask were added 4-phenylcyclohexan-1-one (15.00 g, 86.087 mmol, 1.00 equiv.), THF (130.00 mL), and L-selectride (129.08 mL, 679.021 mmol, 7.02 equiv.) at room temperature. The resulting mixture was stirred for 16 hr at room temperature under nitrogen atmosphere. Then, water (0.16 mL, 8.609 mmol, 0.10 equiv.) and EtOH (0.10 mL, 2.171 mmol, 0.02 equiv.) were added. The resulting mixture was stirred for 1 hr at room temperature under nitrogen atmosphere. NaOH (5.99 g, 149.791 mmol, 1.74 equiv.) and H₂O₂ (0.02 mL, 0.590 mmol, 0.01 equiv.) were added, and the resulting mixture was stirred for 1 hr at 0 degrees C. under nitrogen atmosphere. The resulting mixture was washed with water (2×50 mL). The residue was purified by silica gel column chromatography, eluted with PE/EtOAc (9:1) to afford 4-phenylcyclohexan-1-ol (11.4 g, 75.1%) as a solid.

¹H-NMR (400 MHz, Chloroform-d) δ 7.41-7.15 (m, 5H), 4.16 (p, J=3.0 Hz, 1H), 2.57 (tt, J=12.0, 3.2 Hz, 1H), 2.04-1.84 (m, 4H), 1.71 (tdd, J=14.5, 5.3, 2.4 Hz, 4H), 1.46 (d, J=3.0 Hz, 1H).

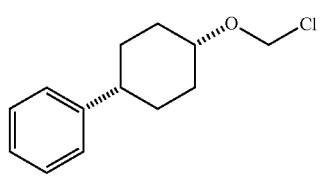

A solution of 4-phenylcyclohexan-1-ol (10.00 g, 56.735 mmol, 1.00 equiv.) in 4N HCl in dioxane (160.00 mL, 640.00 mmol, 11.3 equiv.) was treated with paraformaldehyde (2.56 g, 28.367 mmol, 0.50 equiv.) at room temperature under nitrogen atmosphere. The resulting mixture was stirred for 5 hr at room temperature under nitrogen atmosphere. The resulting mixture was concentrated under reduced pressure. The resulting mixture was used in the next step directly without further purification.

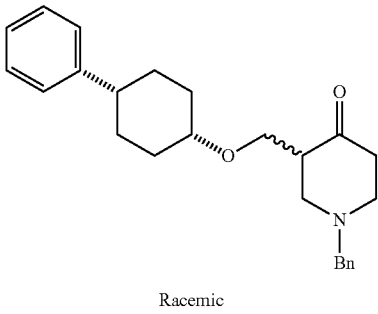

Racemic

To a stirred solution of [4-(chloromethoxy)cyclohexyl]benzene (12.6 g, 56.067 mmol, 1.00 equiv.) in THF (200.00 mL) was added LiHMDS (56.07 mL, 56.070 mmol, 1.00 equiv.) dropwise at −78 degrees C. under nitrogen atmosphere over 15 minutes. The resulting mixture was stirred for 1.5 hr at −78 degrees C. under nitrogen atmosphere. To the above mixture was added [4-(chloromethoxy)cyclohexyl]benzene (12.6 g, 56.067 mmol, 1.00 equiv.) as a solution in THF (50 mL) dropwise over 20 minutes at −78 degrees C. The resulting mixture was stirred for an additional 2 hours at −78 degrees C. The reaction was quenched with saturated aqueous NH$_4$Cl at 0 degrees C. The resulting mixture was extracted with EtOAc (3×100 mL). The combined organic layers were washed with brine (2×130 mL) and dried over anhydrous sodium sulfate. After filtration, the filtrate was concentrated under reduced pressure. The residue was purified by reverse flash chromatography with the following conditions: column, C18 silica gel; mobile phase, MeCN in water, 10% to 100% gradient in 15 minutes; detector, UV 220 nm to afford 1-benzyl-3-[[(4-phenylcyclohexyl)oxy]methyl]piperidin-4-one (6.1 g, 28.80%) as an oil.

LCMS: m/z (ES+), [M+H]+=378.30.

$^1$H-NMR (400 MHz, Chloroform-d) δ 7.42-7.29 (m, 7H), 7.21 (dtd, J=7.0, 3.5, 1.7 Hz, 3H), 3.80 (dd, J=9.6, 4.7 Hz, 1H), 3.77-3.61 (m, 2H), 3.59 (p, J=3.1 Hz, 1H), 3.49 (dd, J=9.6, 8.3 Hz, 1H), 3.33 (ddd, J=11.4, 5.7, 2.4 Hz, 1H), 3.04 (ddd, J=11.7, 5.7, 2.8 Hz, 1H), 2.91 (tt, J=9.7, 5.3 Hz, 1H), 2.68-2.35 (m, 5H), 2.00 (dt, J=13.9, 3.2 Hz, 2H), 1.73 (tdd, J=15.1, 12.4, 3.4 Hz, 2H), 1.61 (d, J=13.4 Hz, 2H), 1.57-1.43 (m, 2H).

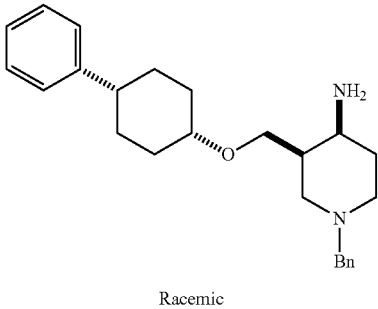

Racemic

To a stirred solution of 1-benzyl-3-[[(4-phenylcyclohexyl)oxy]methyl]piperidin-4-one (2.00 g, 5.298 mmol, 1.00 equiv.) in methanol (12.00 mL) was added ZnCl$_2$ (1.06 mL, 1.060 mmol, 0.2 equiv.) dropwise at room temperature under nitrogen atmosphere. The resulting mixture was stirred for 30 minutes at room temperature under nitrogen atmosphere. To the above mixture was added HCOONH$_4$ (4.00 g, 63.413 mmol, 11.97 equiv.) in portions at room temperature. The resulting mixture was stirred for an additional 1 hour at room temperature. Solid NaBH$_3$CN (665.83 mg, 10.595 mmol, 2.0 equiv.) was added. The reaction was then stirred for 3 hr at ambient temperature and terminated by the addition of water. The quenched reaction was partitioned between 5M NaOH and DCM. The aqueous layer was extracted with DCM, and combined organic layers were dried over sodium sulfate, filtered and concentrated under reduced pressure. The crude product was used in the next step directly without further purification.

LCMS: m/z (ES+), [M+H]+=379.35.

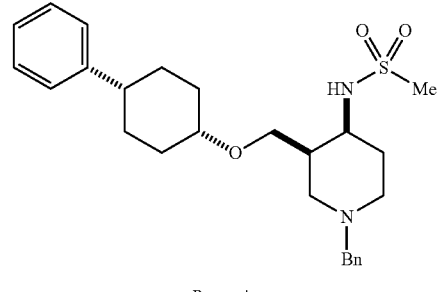

Racemic

To a stirred solution of 1-benzyl-3-[[(4-phenylcyclohexyl)oxy]methyl]piperidin-4-amine (2.00 g, 5.283 mmol, 1.00 equiv.) in DCM (40.00 mL) were added DIPEA (1.02 g, 7.925 mmol, 1.50 equiv.) and methanesulfonyl chloride (726.16 mg, 6.340 mmol, 1.20 equiv.) at 0 degrees C. under nitrogen atmosphere. The resulting mixture was stirred for additional 1 hr at room temperature. The reaction was quenched with methanol at room temperature. The resulting mixture was concentrated under reduced pressure. The crude product (2.0 g) was purified by Prep-HPLC with the following conditions (Column: XBridge® (Waters Technologies Corp., Milford, Massachusetts) Prep OBD C18 Column, 30×150 mm Sum; Mobile Phase A: Water (10 mmol/L NH$_4$HCO$_3$), Mobile Phase B: ACN; Flow rate: 60 mL/min; Gradient: 52 B to 86 B in 8 min; 254/220 nm) to afford (cis)-N-(1-benzyl-3-[[(4-phenylcyclohexyl)oxy]methyl]piperidin-4-yl)methanesulfonamide (420 mg, 17.5%) as a solid.

LCMS: m/z (ES+), [M+H]+=457.35.

$^1$H-NMR: (400 MHz, Chloroform-d) δ 7.37-7.17 (m, 13H), 3.70-3.61 (m, 2H), 3.52 (d, J=11.8 Hz, 2H), 3.42 (d, J=13.5 Hz, 1H), 2.98 (s, 3H), 2.75 (s, 1H), 2.56 (tt, J=10.8, 4.3 Hz, 2H), 2.31 (d, J=26.5 Hz, 3H), 2.13-1.90 (m, 4H), 1.73 (d, J=9.9 Hz, 4H).

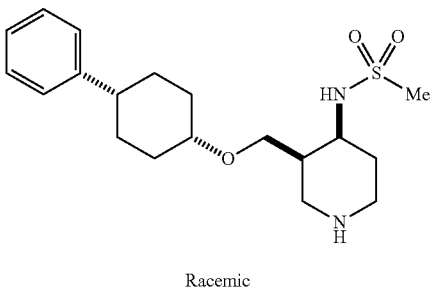

Racemic

To a stirred solution of N-[(cis)-1-benzyl-3-[[(4-phenyl-cyclohexyl)oxy]methyl]piperidin-4-yl]methanesulfonamide (420.00 mg, 0.920 mmol, 1.00 equiv.) and Pd(OH)$_2$/C (258.39 mg, 0.368 mmol, 0.4 equiv.) in isopropanol (30.00 mL) was added 4N HCl (230.00 microL, 0.920 mmol, 1.0 equiv.) dropwise at room temperature under hydrogen atmosphere. The resulting mixture was stirred overnight at room temperature under hydrogen atmosphere. The resulting mixture was filtered, the filter cake was washed with MeOH (3×10 mL). The filtrate was concentrated under reduced pressure. The crude product was used in the next step directly without further purification.

LCMS: m/z (ES+), [M+H]+=367.20.

(Compound 10)

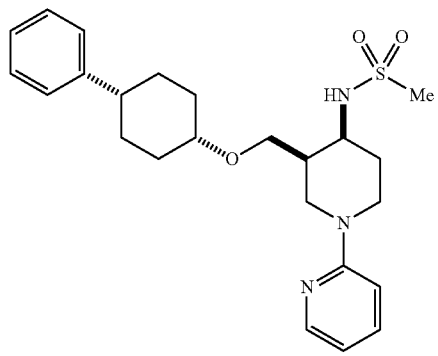

To a stirred solution of N-[(cis)-3-([[(1s,4s)-4-phenylcyclohexyl]oxy]methyl)piperidin-4-yl]methanesulfonamide (350.00 mg, 0.955 mmol, 1.00 equiv.) and K$_2$CO$_3$ (395.93 mg, 2.865 mmol, 3.00 equiv.) in DMSO (20.00 mL) was added 2-fluoropyridine (185.43 mg, 1.910 mmol, 2.00 equiv.) in portions at room temperature under nitrogen atmosphere. The resulting mixture was stirred for an additional 8 hr at 120 degrees C. The residue was purified by reverse flash chromatography with the following conditions: column, C18 silica gel; mobile phase, ACN in water, 60% to 100% gradient in 15 min; detector, UV 254 nm to afford N-[(cis)-1-(pyridin-2-yl)-3-([[(1s,4s)-4-phenylcyclohexyl]oxy]methyl)piperidin-4-yl]methanesulfonamide (280 mg, 66.10%) as a solid. The racemic mixture was separated by chiral prep-HPLC to afford the enantiopure product (95.1 mg) as a solid.

LCMS: m/z (ES+), [M+H]+=444.20.

$^1$H-NMR (400 MHz, Methanol-d4) δ 8.07 (ddd, J=5.0, 2.0, 0.8 Hz, 1H), 7.52 (ddd, J=8.8, 7.1, 2.0 Hz, 1H), 7.29-7.20 (m, 5H), 7.18-7.12 (m, 1H), 6.88 (d, J=8.7 Hz, 1H), 6.64 (ddd, J=7.2, 5.0, 0.8 Hz, 1H), 3.92-3.82 (m, 2H), 3.76 (dd, J=13.3, 6.8 Hz, 1H), 3.66 (dd, J=9.4, 5.8 Hz, 1H), 3.63-3.60 (m, 1H), 3.59-3.52 (m, 2H), 3.46 (dt, J=13.2, 5.8 Hz, 1H), 3.05 (s, 3H), 2.55 (tt, J=12.3, 3.4 Hz, 1H), 2.30 (ddt, J=9.7, 6.9, 3.6 Hz, 1H), 2.11-2.02 (m, 2H), 1.93-1.78 (m, 4H), 1.65-1.54 (m, 4H).

Example 1.4

(Compound 19)

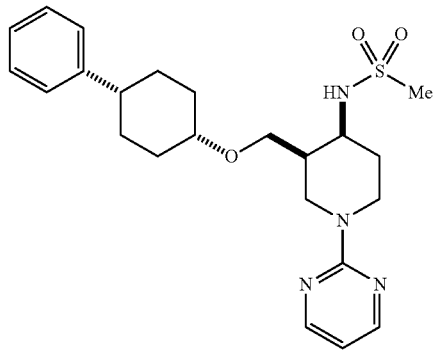

To a stirred mixture of N-((3R,4S)-3-[[(4-phenylcyclohexyl)oxy]methyl]piperidin-4-yl)methanesulfonamide (50.00 mg, 0.136 mmol, 1.00 equiv.) and 2-fluoropyrimidine (20.07 mg, 0.205 mmol, 1.50 equiv.) in DMSO (10 mL) was added K$_2$CO$_3$ (47.13 mg, 0.341 mmol, 2.5 equiv.) at room temperature under air atmosphere. The resulting mixture was stirred for 2 hr at room temperature under nitrogen atmosphere. The resulting mixture was filtered, and the filter cake was washed with MeCN (3×5 mL). The filtrate was concentrated under reduced pressure. The residue was purified by reverse flash chromatography with the following conditions: column, C18 silica gel; mobile phase, MeCN in water, 0 to 0 gradient in 10 min, 0 to 100% gradient in 15 min, 100% to 100% in 15 min; detector, UV 254 nm. This resulted in N-[(3R,4S)-1-(pyrimidin-2-yl)-3-([[(1s,4s)-4-phenylcyclohexyl]oxy]methyl)piperidin-4-yl]methanesulfonamide (53 mg, 85.64%) as a solid.

LCMS: m/z (ES+), [M+H]+=445.

$^1$H-NMR (400 MHz, Methanol-d4) δ 8.30 (d, J=4.8 Hz, 2H), 7.31-7.22 (m, 4H), 7.20-7.12 (m, 1H), 6.56 (t, J=4.8 Hz, 1H), 4.06 (td, J=14.7, 13.8, 6.4 Hz, 2H), 3.92-3.84 (m, 2H), 3.87 (s, 2H), 3.83-3.73 (m, 1H), 3.64 (dd, J=9.6, 6.1 Hz, 2H), 3.54 (dd, J=9.4, 7.3 Hz, 1H), 3.05 (s, 3H), 2.60-2.50 (m, 1H), 2.25 (s, 2H), 1.71-1.49 (m, 6H), 1.31 (s, 1H).

Example 1.5

(Compound 37)

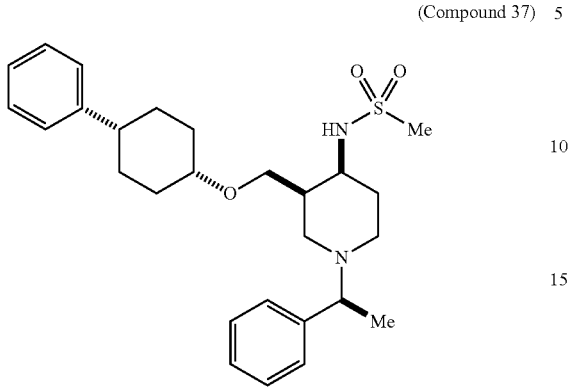

To a solution of N-((3R,4S)-3-((((1s,4S)-4-phenylcyclohexyl)oxy)methyl)piperidin-4-yl)methanesulfonamide (200 mg, 1.00 equiv., 546 micromol) in acetophenone (393 mg, 6.00 equiv., 3.27 mmol) were added titanium(IV) isopropoxide (620 mg, 662 microL, 2.18 mmol, 4.00 equiv.). The reaction mixture was stirred at 25 degrees C. for 30 minutes. To the above reaction mixture was added EtOH (2 mL) and sodium cyanoborohydride (343 mg, 5.46 mmol, 10.0 equiv.). The reaction mixture was stirred for one hour at 25 degrees C. under a nitrogen atmosphere. The resulting mixture was diluted with water (50 mL) and extracted with EtOAc (3*50 mL). The combined organic layers were washed with brine (3×50 mL), dried over anhydrous $Na_2SO_4$ and concentrated under reduced pressure. The crude was purified by reverse flash chromatography with the following conditions (C18 column; mobile phase A: 0.08% $NH_4HCO_3$ (aq), mobile phase B: ACN, 1% to 100% gradient in 30 min; detector, UV 254 nm) to afford N-((3R,4S)-3-((((1s,4S)-4-phenylcyclohexyl)oxy)methyl)-1-((S)-1-phenylethyl)piperidin-4-yl)methanesulfonamide (180 mg, 382 micromol, 70.1%) as an oil. The racemic mixture was separated by chiral prep-HPLC to afford the enantiopure product (88.3 mg, 0.188 mmol, 34.4% overall yield) as a solid.

LCMS: m/z (ES+), [M+H]+=471.25.

$^1$H-NMR (400 MHz, Methanol-d4) δ 7.37-7.27 (m, 4H), 7.26 (d, 2H), 7.25-7.18 (m, 2H), 7.22-7.11 (m, 2H), 3.64 (d, 2H), 3.56-3.41 (m, 1H), 2.98 (s, 3H), 2.53 (ddd, 1H), 2.16 (d, 1H), 1.99 (d, 2H), 1.85 (q, 2H), 1.81-1.64 (m, 2H), 1.57 (s, 5H), 1.40 (d, 3H).

Example 1.6

(Compound 39)

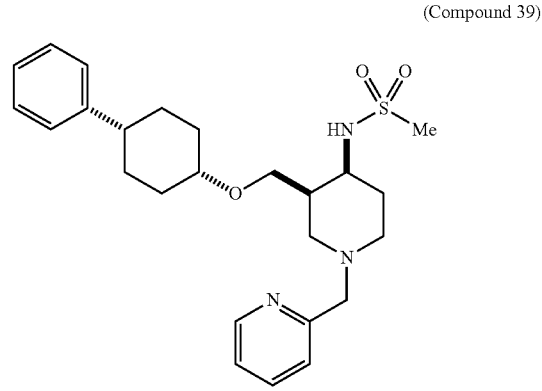

To a solution of N-((3R,4S)-3-((((1s,4S)-4-phenylcyclohexyl)oxy)methyl)piperidin-4-yl)methanesulfonamide (100 mg, 273 micromol, 1.00 equiv.) and picolinaldehyde (117 mg, 1.09 mmol, 4.00 equiv.) in methanol (5 mL) were added diisopropylethylamine (106 mg, 143 microL, 819 micromol, 3.00 equiv.) and sodium triacetoxyborohydride (578 mg, 2.73 mmol, 10.0 equiv.). The reaction mixture was stirred for 2 hr at 25 degrees C. under a nitrogen atmosphere. The crude was purified by reverse flash chromatography with the following conditions (C18 column; mobile phase A: water, mobile phase B: ACN, 1% to 100% gradient in 30 min; detector, UV 254 nm) to afford N-((3R,4S)-3-((((1s,4S)-4-phenylcyclohexyl)oxy)methyl)-1-(pyridin-2-ylmethyl)piperidin-4-yl)methanesulfonamide (48.1 mg, 105 μmol, 38.5%) as a solid.

LCMS: m/z (ES+), [M+H]+=458.40.

$^1$H-NMR (400 MHz, Methanol-d4) δ 8.46 (dt, 2H), 7.79 (td, 2H), 7.56 (d, 2H), 7.32-7.21 (m, 6H), 7.21-7.10 (m, 6H), 3.74-3.61 (m, 8H), 3.64-3.53 (m, 4H), 3.00 (s, 6H), 2.70 (s, 2H), 2.56 (s, 3H), 2.55 (d, 1H), 2.51 (dt, 4H), 2.23 (q, 2H), 2.06-2.01 (m, 1H), 2.00 (s, 3H), 1.99-1.94 (m, 1H), 1.92-1.63 (m, 9H), 1.57 (ddt, 9H).

Example 1.7

(Compound 44)

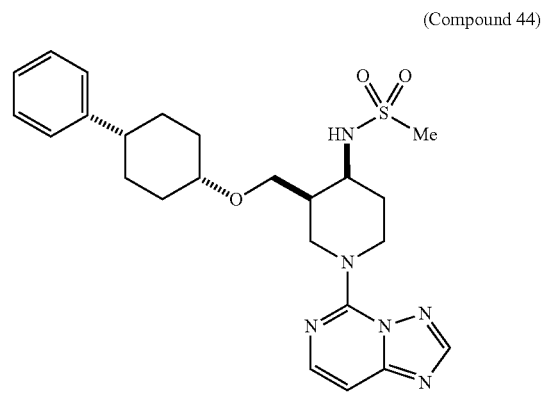 [SMILES: CS(=O)(=O)N[C@H]1CCN(c2nccc3ncnn23)C[C@H]1CO[C@H]1CC[C@@H](c2ccccc2)CC1]

To a solution of N-((3R,4S)-3-((((1s,4S)-4-phenylcyclohexyl)oxy)methyl)piperidin-4-yl)methanesulfonamide (33 mg, 90 micromol, 1.00 equiv.) and 5-chloro[1,2,4]triazolo

[1,5-c]pyrimidine (17 mg, 0.11 mmol, 1.2 equiv.) in DMSO (1.5 mL) was added K₂CO₃ (25 mg, 0.18 mmol, 2.0 equiv.). The resulting mixture was stirred for 18 hr at 120 degrees C. and then filtered. The filter cake was washed with DCM (3×2 mL), and the filtrate was concentrated under reduced pressure. The crude was purified by reverse flash chromatography with the following conditions (C18 column; mobile phase A: water (0.1% NH₄HCO₃), mobile phase B: ACN, 65% to 75% gradient in 30 min; detector, UV 254 nm) to afford N-((3R,4S)-1-([1,2,4]triazolo[1,5-c]pyrimidin-5-yl)-3-((((1s,4S)-4-phenylcyclohexyl)oxy)methyl)piperidin-4-yl)methanesulfonamide (22.3 mg, 46.0 μmol, 51%) as a solid.

LCMS: m/z (ES+), [M+H]+=485.

¹H-NMR (400 MHz, Methanol-d4) δ 8.31 (s, 1H), 7.97 (d, J=6.1 Hz, 1H), 7.26 (dd, J=8.3, 7.0 Hz, 2H), 7.20-7.12 (m, 3H), 7.09 (d, J=6.1 Hz, 1H), 4.45-4.28 (m, 2H), 4.17 (dd, J=13.5, 3.4 Hz, 1H), 4.06 (dd, J=13.5 Hz, 1H), 3.89 (m, 1H), 3.68 (dd, J=9.6, 5.6 Hz, 1H), 3.57 (dd, J=9.6, 8.0 Hz, 1H), 3.52-3.46 (m, 1H), 3.06 (s, 4H), 2.54-2.43 (m, 1H), 2.43-2.37 (m, 1H), 2.16-1.91 (m, 2H), 1.85 (d, J=13.1 Hz, 1H), 1.75 (td, J=12.8, 3.9 Hz, 1H), 1.71 (td, J=12.7 Hz, 1H), 1.65 (td, J=13.8, 3.1 Hz, 1H), 1.59-1.51 (m, 2H), 1.49-1.41 (m, 2H).

Example 1.8

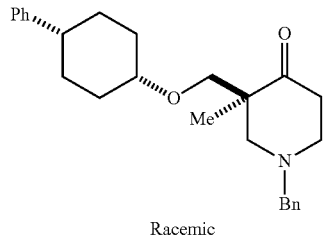 [SMILES: C[C@@]1(CO[C@H]2CC[C@@H](c3ccccc3)CC2)CN(Cc2ccccc2)CCC1=O]

Racemic

To a suspension of NaH (53.0 mg, 60% weight, 1.32 mmol, 1.00 equiv.) in THF (10 mL) was added 1-benzyl-3-((((1S,4S)-4-phenylcyclohexyl)oxy)methyl)piperidine-4-one (500 mg, 1.32 mmol, 1.00 equiv.) in THF (10 mL) at 0 degrees C. The resulting mixture was stirred for 30 minutes at 0 degrees C. To the reaction was added a solution of methyl iodide (0.166 mL, 0.376 grams, 2.65 mmol, 2.00 equiv.) in THF (10 mL) dropwise at 0 degrees C. under nitrogen atmosphere. The resulting mixture was stirred for an additional 2 hr at 25 degrees C. Then, the reaction was quenched by the addition of saturated aqueous ammonium chloride at 0 degrees C. The resulting mixture was extracted with ethyl acetate (3×50 mL EtOAc). The combined organic layers were concentrated under reduced pressure. The resulting residue was purified by prep-TLC (PE/EtOAc=8/1) to afford (S)-1-benzyl-3-methyl-3-((((1S,4R)-4-phenylcyclohexyl)oxy)methyl)piperidin-4-one (124 mg, 0.317 mmol, 20% yield) as an oil.

LCMS: m/z (ES+), [M+H]+=312.

¹H-NMR (400 MHz, Chloroform-d) δ 7.45-7.31 (m, 7H), 7.25-7.19 (m, 3H), 3.75-3.54 (m, 5H), 2.89-2.78 (m, 2H), 2.72-2.42 (m, 5H), 2.01 (dd, 2H), 1.84-1.71 (m, 2H), 1.67-1.59 (m, 2H), 1.51 (dd, 2H), 1.23 (s, 3H).

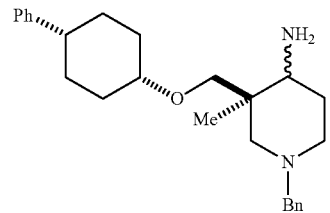 [SMILES: C[C@@]1(CO[C@H]2CC[C@@H](c3ccccc3)CC2)CN(Cc2ccccc2)CCC1N]

To a stirred solution of (S)-1-benzyl-3-methyl-3-((((1S,4R)-4-phenylcyclohexyl)oxy)methyl)piperidin-4-one (230 mg, 0.587 mmol, 1.00 equiv.) in methanol (10 mL) was added zinc chloride (117 microL, 0.7 molar, 82.2 micromol, 0.14 equiv.) at 25 degrees C. The resulting mixture was stirred for 10 minutes at 25 degrees C. To the above mixture was added ammonium formate (741 mg, 11.7 mmol, 20.0 equiv.) at 25 degrees C. under nitrogen atmosphere. The resulting mixture was stirred for additional 30 minutes at 25 degrees C. To the above mixture was added NaCNBH₃ (221 mg, 3.52 mmol, 6.00 equiv.) at 25 degrees C. under nitrogen atmosphere. The reaction was stirred for additional three hours at 25 degrees C., and then it was cooled to 0 degrees C. and quenched by the addition of saturated aqueous ammonium chloride. The resulting mixture was extracted with dichloromethane (3×50 mL). The combined organic layers were washed with brine, dried over anhydrous Na₂SO₄, and filtered. The filtrate was concentrated under reduced pressure to afford (3R)-1-benzyl-3-methyl-3-((((1S,4S)-4-phenylcyclohexyl)oxy)methyl)piperidin-4-amine (220 mg, 560 μmol, 95.4% yield) as an oil. The crude product was used in the next step directly without further purification.

LCMS: m/z (ES+), [M+H]+=393.

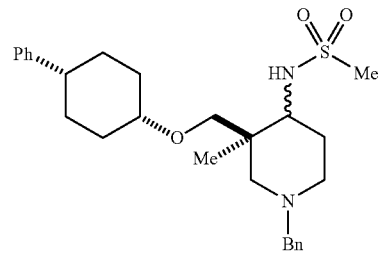 [SMILES: C[C@@]1(CO[C@H]2CC[C@@H](c3ccccc3)CC2)CN(Cc2ccccc2)CCC1NS(C)(=O)=O]

To a solution of (3R)-1-benzyl-3-methyl-3-((((1S,4S)-4-phenylcyclohexyl)oxy)methyl)piperidine-4-amine (230 mg, 0.586 mmol, 1.00 equiv.) and diisopropylethylamine (0.306 mL, 227 mg, 1.76 mmol, 3.00 equiv.) in DCM (20 mL) was added methanesulfonyl chloride (0.0685 mL, 101 mg, 0.879 mmol, 1.50 equiv.). The resulting mixture was stirred for one hour at 25 degrees C. The residue was purified by prep-TLC (PE/EtOAC=2/1) to afford N-((3R)-1-benzyl-3-methyl-3-((((1s,4S)-4-phenylcyclohexyl)oxy)methyl)piperidin-4-yl)methanesulfonamide (90 mg, 0.19 mmol, 33%) as an oil.

LCMS: m/z (ES+), [M+H]+=471.

¹H-NMR (400 MHz, DMSO-d6) δ 7.31-7.16 (m, 10H), 6.84 (d, 1H), 3.87 (s, 1H), 3.66-3.51 (m, 2H), 3.49-3.38 (m, 3H), 3.23 (s, 1H), 3.18 (s, 1H), 3.07-2.99 (m, 1H), 2.93 (s, 3H), 2.80 (d, 2H), 2.55 (d, 1H), 2.00 (d, 2H), 1.87-1.38 (m, 12H), 1.25 (dd, 6H), 0.98 (s, 3H).

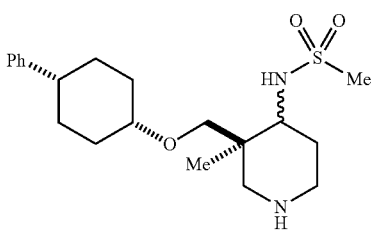 [SMILES: C[C@@]1(CO[C@H]2CC[C@@H](c3ccccc3)CC2)CNCCC1NS(C)(=O)=O]

To a solution of N-((3R)-1-benzyl-3-methyl-3-((((1s,4S)-4-phenylcyclohexyl)oxy)methyl)piperidin-4-yl)methanesulfonamide (140 mg, 297 micromol, 1.00 equiv.) in isopropanol (15 mL) was added palladium hydroxide on carbon (1.25 g, 10% weight, 892 micromol, 3.00 equiv.) at nitrogen atmosphere. To the above mixture was added HCl (744 microL, 4 molar, 2.97 mmol, 10.0 equiv.). The resulting mixture was hydrogenated at room temperature for 12 hr under hydrogen atmosphere using a hydrogen balloon, filtered through a Celite® pad, and concentrated under reduced pressure to afford the crude product. This crude product was used in the next step directly without further purification.

LCMS: m/z (ES+), [M+H]+=381.

(Compound 29)

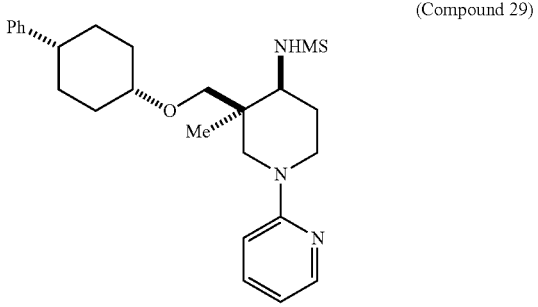

To a solution of N-((3R)-3-methyl-3-((((1s,4S)-4-phenylcyclohexyl)oxy)methyl)piperidin-4-yl)methanesulfonamide (113 mg, 297 micromol, 1.00 equiv.) and $K_2CO_3$ (82.1 mg, 594 micromol, 2.00 equiv.) in DMSO (4 mL) was added 2-fluoropyridine (86.5 mg, 891 micromol, 3.00 equiv.). The resulting mixture was stirred for 24 hr at 120 degrees C.

The crude product was purified by prep chiral HPLC with the following conditions: column, DZ-CHIRALPAK® IG-3, 4.6*50 mm 3 um; mobile phase A, hexanes with 0.2% isopropanol; mobile phase B, EtOH:DCM=1:1; isocratic 85:15; flow rate, 1 mL/min. This afforded N-((3R,4S)-3-methyl-3-((((1s,4S)-4-phenylcyclohexyl)oxy)methyl)-1-(pyridin-2-yl)piperidin-4-yl)methanesulfonamide (10 mg, 22 μmol, 33%) as a solid.

LCMS: m/z (ES+), [M+H]+=458.

$^1$H-NMR (400 MHz, Methanol-d4) δ 8.04 (dd, 1H), 7.50 (dd, 1H), 7.33-7.23 (m, 2H), 7.23-7.11 (m, 3H), 6.89 (d, 1H), 6.62 (dd, 1H), 4.43-4.29 (m, 1H), 4.20 (dd, 1H), 3.57 (d, 1H), 3.51-3.36 (m, 3H), 3.09-2.89 (m, 4H), 2.74 (d, 1H), 2.54 (dd, 1H), 2.08-1.98 (m, 3H), 1.98-1.83 (m, 1H), 1.77 (d, 2H), 1.66-1.47 (m, 2H), 1.42-1.29 (m, 1H), 1.24 (s, 3H).

Example 2: Human $OX_2R$ IP1 Assay

T-Rex CHO cells stably overexpressing the human orexin-2 receptor ($OX_2R$) were induced overnight with 1 μg/mL of doxycycline in a T225 flask. 24 hours post induction, cells were lifted with accutase and plated into a 384-well proxy plate at 30,000 cells/well. Cells were then treated with different test compounds in 1× stimulation buffer containing 10 mM Hepes, 1 mM $CaCl_2$), 0.5 mM $MgCl_2$, 4.2 mM KCl, 146 mM NaCl, 5.5 mM glucose, and 50 mM LiCl, pH 7.4, for 1 hr at 37 degrees C. Following incubation, the reaction was terminated by the addition of detection mix, which is composed of IP1-d2 and anti-IP1-cryptate diluted in lysis buffer as well as 1× stimulation buffer. The plates were allowed to incubate for 1 hour at room temperature and were then read in the EnVision® multimode plate reader, measuring inositol phosphate levels.

Cisbio IP1 is a cell-based functional assay quantifying the accumulation of inositol monophosphate (IP), a metabolite released as a result of orexin 2 receptor activation through the phospholipase C-Gq signaling pathway. This is a competitive immunoassay in which the IP1 produced by the cells upon receptor activation competes with the IP1 analog coupled to the d2 fluorophore (acceptor) for binding to an anti-IP1 monoclonal antibody labeled with Eu cryptate (donor). The measured HTRF-FRET based signal is inversely proportional to the IP1 concentration produced.

The $EC_{50}$ values reported in Table 2 were obtained according to the human $OX_2R$ IP1 assay described above. Data are the mean $EC_{50}$ values ±S.E.M. The compound methyl (2R,3S)-3-((methylsulfonyl)amino)-2-(((cis-4-phenylcyclohexyl)oxy)methyl)-piperidine-1-carboxylate (sometimes referred to herein as Reference Compound A) is a reference compound which is disclosed in Example 5 of PCT publication no. WO2017/135306.

TABLE 2

| Compound | Compound No. | $EC_{50}$ (nM) |
|---|---|---|
| (structure) | 1 | * |

TABLE 2-continued

| Compound | Compound No. | EC$_{50}$ (nM) |
|---|---|---|
| | 2 | *** |
| | 3 | *** |
| | 4 | *** |
| | 5 | *** |

TABLE 2-continued

| Compound | Compound No. | EC$_{50}$ (nM) |
|---|---|---|
| | 6 | *** |
| | 7 | *** |
| | 8 | * |
| | 9 | * |

TABLE 2-continued

| Compound | Compound No. | EC$_{50}$ (nM) |
|---|---|---|
| | 10 | *** |
| | 11 | * |
| | 12 | * |
| | 13 | * |

TABLE 2-continued

| Compound | Compound No. | EC$_{50}$ (nM) |
|---|---|---|
| | 14 | * |
| | 15 | *** |
| | 16 | *** |
| | 17 | *** |

TABLE 2-continued

| Compound | Compound No. | EC$_{50}$ (nM) |
|---|---|---|
| [structure: 3,5-dimethylphenyl-cyclohexyl-O-CH2-piperidine(N-pyridin-2-yl) with NHSO2Me] | 18 | *** |
| [structure: phenyl-cyclohexyl-O-CH2-piperidine(N-pyrimidin-2-yl) with NHSO2Me] | 19 | *** |
| [structure: phenyl-cyclohexyl-O-CH2-piperidine(N-pyrimidin-4-yl) with NHSO2Me] | 20 | *** |
| [structure: phenyl-cyclohexyl-O-CH2-piperidine(N-pyrazin-2-yl) with NHSO2Me] | 21 | *** |

TABLE 2-continued
| Compound | Compound No. | EC$_{50}$ (nM) |
|---|---|---|
| 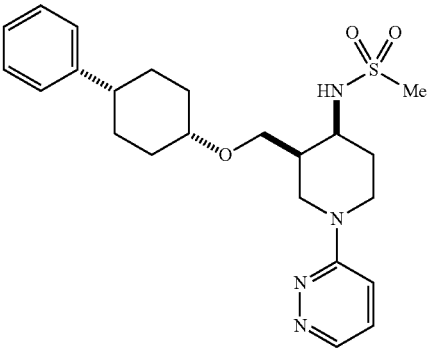 | 22 | *** |
| 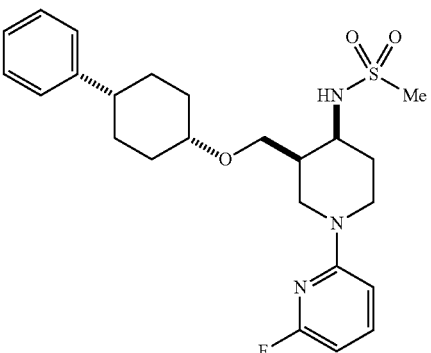 | 23 | *** |
| 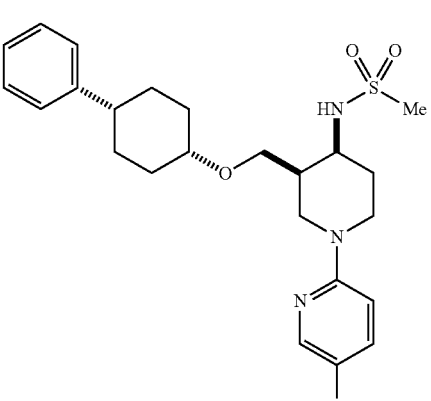 | 24 | *** |
| 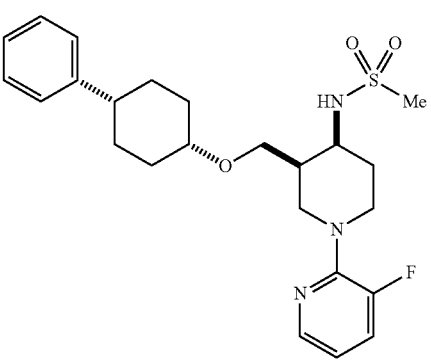 | 26 | *** |

TABLE 2-continued

| Compound | Compound No. | EC$_{50}$ (nM) |
|---|---|---|
| | 27 | *** |
| | 28 | *** |
| | 29 | *** |
| | 30 | ** |

TABLE 2-continued

| Compound | Compound No. | EC$_{50}$ (nM) |
|---|---|---|
| [structure: 3-hydroxyphenyl-cyclohexyl-OCH2-piperidine(N-pyridin-2-yl)-NHS(O)2Me] | 31 | *** |
| [structure: 4-hydroxyphenyl-cyclohexyl-OCH2-piperidine(N-pyridin-2-yl)-NHS(O)2Me] | 32 | *** |
| [structure: 3-trifluoromethylphenyl-cyclohexyl-OCH2-piperidine(N-pyridin-2-yl)-NHS(O)2Me] | 33 | ** |
| [structure: 3-cyanophenyl-cyclohexyl-OCH2-piperidine(N-pyridin-2-yl)-NHS(O)2Me] | 35 | *** |

TABLE 2-continued
| Compound | Compound No. | EC$_{50}$ (nM) |
|---|---|---|
| 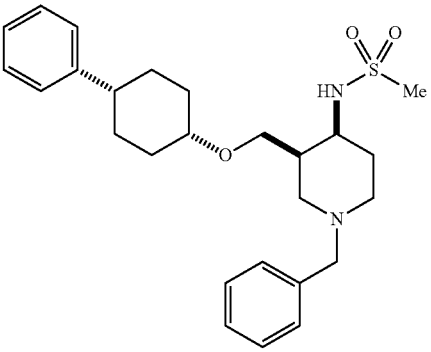 | 36 | * |
| 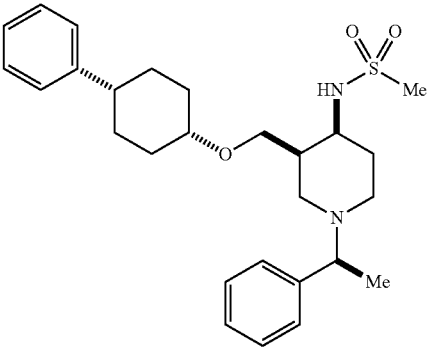 | 37 | * |
| 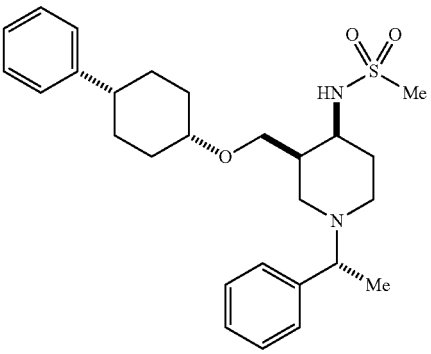 | 38 | * |
| 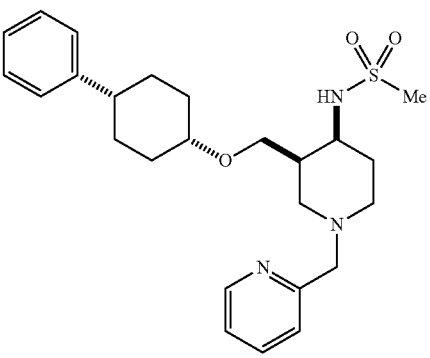 | 39 | * |

TABLE 2-continued

| Compound | Compound No. | EC$_{50}$ (nM) |
|---|---|---|
| | 40 | * |
| | 41 | * |
| | 42 | * |
| | 43 | * |

TABLE 2-continued

| Compound | Compound No. | EC$_{50}$ (nM) |
|---|---|---|
| [structure] | 44 | ** |
| [structure] | 45 | *** |
| [structure] | 53 | *** |
| methyl (2R,3S)-3-((methylsulfonyl)amino)-2-(((cis-4-phenylcyclohexyl)oxy)methyl)-piperidine-1-carboxylate | — | *** |

***EC$_{50}$ < 100 nM
**EC$_{50}$ 100-1,000 nM
*EC$_{50}$ > 1,000 nM

Example 3: MDCK-MDR1 Permeability Assay

The bidirectional permeability (Apical to Basal and Basal to Apical directions) of test compounds in MDCK-MDR1 cells were evaluated using MDCK-MDR1 cells seeded in Solvo PreadyPort™ MDCK 96-well plate. Once the plate was received from ReadyCell (Barcelona, Spain), it was treated as per PreadyPort™ user's manual.

For the Apical to Basolateral (A→B) permeability, 80 µL of test compound (3 µM) co-dosed with LY (Lucifer Yellow) (100 µM) in HBSS (Hank's Balanced Salt Solution) assay buffer was added to the donor side (A) while 250 µL of HBSS buffer was added to the receiver side (B). For the Basolateral to Apical (B→A) permeability, 255 µL of test compound (3 µM) in HBSS assay buffer was added to the donor side (B) while 75 µL of HBSS buffer containing LY (100 µM) was added to the receiver side (A).

The plate was placed in an incubator set at 37 degrees C. After 10 minutes of pre-warming, 5 µL aliquot was taken from donor compartment and set aside as the dosing solution. The MDCK-MDR1 incubation plate was placed back into the incubator for 2 hours of incubation at 37 degrees C. After 2 hours of incubation, 25 µL and 5 µL aliquots were removed from the receiver and donor sides, respectively. To the 5 µL aliquots taken from the donor sides (before and after a 2-hour incubation) were diluted with 20 µL of the HBSS buffer. All samples were mixed with 150 μL with acetonitrile containing internal standard (IS) and 200 μL water, and analyzed by LC-MS/MS.

The apparent permeability ($P_{app}$) was calculated using the following formula:

$$P_{app} = dQ/dt \times 1/A \times C_0$$

where:
dQ/dt: amount of translocated material over incubation time (nmol/s)
A: area of insert (0.14 cm² for PreadyPort™ MDR1-96)
$C_0$: initial concentration of product applied in apical (A→B) or basal (B→A) compartment (nmol/mL).

The efflux ratio (ER) was measured by dividing the $P_{app}$ (basolateral to apical direction) by $P_{app}$ (apical to basolateral direction). It is a general measure of the involvement of active processes. An ER>2 is considered positive for active transport.

Percent recovery was measured using the following equation:

$$\text{Percent Recovery} = 100 \times \frac{C_R^{final} \times V_R + C_D^{final} \times V_D}{V_D \times C_N}$$

where:
$V_R$: Volume of the receiver compartment (mL)
$V_D$: Volume of the donor compartment (mL)
$C_N$: Concentration of dosing solution (μM) collected after 10 minutes of incubation
$C_R^{final}$: Receiver concentration at the end of the incubation (μM)
$C_D^{final}$: Donor concentration at the end of the incubation (μM)

The data reported in Table 3 were obtained according to the MDCK-MDR1 permeability assay described above.

TABLE 3

| Compound No. | $P_{app}$ A → B ($10^{-6}$ cm/s) | Efflux ratio (ER) |
|---|---|---|
| 1 | 2.7 | 12 |
| 3 | 1.7 | 24 |
| 4 | 1.2 | 14 |
| 5 | <0.9 | >7.2 |
| 6 | 1.3 | 2.8 |
| 7 | <1.2 | >4.3 |
| 8 | 1.8 | 15 |
| 9 | 0.97 | 25 |
| 10 | 5.6 | 1.4 |
| 11 | 1.6 | 11 |
| 12 | 1.0 | 33 |
| 13 | 0.67 | 18 |
| 14 | <0.12 | >56 |
| 15 | <0.33 | >6.9 |
| 16 | <0.90 | >7.9 |
| 17 | <0.28 | >6.9 |
| 18 | <1.8 | >2.6 |
| 19 | 1.2 | 14 |
| 20 | 1.1 | 17 |
| 21 | 0.69 | 35 |
| 22 | 1.3 | 23 |
| 23 | <2.0 | >5.4 |
| 24 | 0.28 | 30 |
| 25 | <0.41 | >58 |
| 26 | 0.31 | 37 |
| 27 | 2.7 | 3.0 |
| 28 | <1.2 | >3.4 |
| 29 | <0.42 | >17 |
| 30 | 0.70 | 28 |

TABLE 3-continued

| Compound No. | $P_{app}$ A → B ($10^{-6}$ cm/s) | Efflux ratio (ER) |
|---|---|---|
| 31 | 1.0 | 18 |
| 32 | 0.41 | 34 |
| 33 | 0.07 | 15 |
| 35 | 1.3 | 12 |
| 36 | <0.21 | >12 |
| 37 | 0.38 | 12 |
| 38 | 0.74 | 3.2 |
| 39 | 1.4 | 15 |
| 40 | 1.3 | 8.2 |
| 41 | 1.7 | 16 |
| 42 | 0.86 | 2.9 |
| 43 | 2.4 | 8.8 |
| 44 | 3.0 | 6.4 |
| 45 | 1.9 | 2.2 |
| Reference Compound A | 5.0 | 5.9 |

Example 4: Hepatocytes Stability Assay

In vitro metabolic stability was assessed using cryopreserved hepatocytes from male Sprague Dawley rats and a pool of 50 mixed gender humans (BioIVT, Baltimore, MD). The incubation mixtures were prepared by mixing 250 μL of pre-warmed KHB (Krebs-Henseleit buffer) containing 2×10⁶ cell/mL of hepatocytes with 250 μL of pre-warmed KHB buffer containing 2 μM of test compounds in a 48-well plate, giving a final concentration of 1 μM test compound (0.1% DMSO) and 1×10⁶ cell/mL of hepatocytes. The reaction mixture was incubated at 37 degrees C. A 50 μL aliquot of incubation mixture was taken at time points (0, 15, 30, 60, 120 and 240 minutes) and transferred into a 96-well plate containing 300 μL ice-cold acetonitrile (containing 30 ng/mL of labetalol and 10 ng/mL of Naltrexone-d3 as internal standards) and immediately placed in ice to terminate the reaction. Samples were centrifuged, and supernatants were transferred into 96-well plates for liquid chromatography with tandem mass spectrometry (LC-MS/MS) analysis to monitor the depletion of the test compound.

Data was calculated as percent remaining by assuming zero-minute time point peak area ratio (analyte/IS) as 100% and dividing remaining time point peak area ratios by zero-minute time point peak area ratio. Data were fitted to a first-order decay model to determine half-life. From a plot of log (ln) peak area against time, the slope of the line was determined.

Subsequently, half-life ($T_{1/2}$) and intrinsic clearance ($CL_{int}$) were calculated using the equations below:

Elimination rate constant$(k) = (-\text{slope})$

Half-life$(T_{1/2})\text{min} = 0.693/k$

Intrinsic Clearance$(CL_{int})(\text{mL/min/million cells}) = (V \times 0.693)/T_{1/2}$ $V$=incubation volume mL/number of cells The in vitro $T_{1/2}$ was converted to in vitro intrinsic clearance ($CL_{int,hep}$) in units of mL/min/kg using the formula shown below:

$$CLint, hep = \frac{0.693}{T1/2} \times \frac{\text{mL incubation}}{\text{million cells}} \times \frac{120 \text{ million cells}}{\text{g Liver}} \times \frac{\text{g liver}}{\text{kg body}}$$

The in vitro intrinsic clearance ($CL_{int,hep}$) was scaled to in vivo hepatic clearance ($CL_{,hep}$) using the following equation which was adapted from a well-stirred model.

$$CL, hep = \frac{Q \times fu \times CLint, hep}{Q + fu \times CLint, hep}$$

where Q is the liver blood flow and fu is the fraction unbound (assumed to be unity in this case). All parameters used in the calculation are shown below (Table 4).

TABLE 4

Physiological Parameters Used in the In Vitro To In Vivo Scaling

|  | Mouse | Rat | Dog | Monkey | Human |
|---|---|---|---|---|---|
| Body Weight (kg) | 0.02 | 0.25 | 10 | 5 | 70 |
| Liver weight (g/kg) | 87.5 | 40 | 32 | 30 | 25.7 |
| Liver Blood Flow (mL/min/kg) | 90 | 55.2 | 30.9 | 43.6 | 20.7 |

Davies B. and Morris T. (1993) Physiological Parameters in Laboratory Animals and Humans. Pharma Res. 10 (7):1093-1095.

The extraction ratio (ER) was calculated by dividing the hepatic clearance of a compound to the liver blood flow. The data reported in Table 5 were obtained according to the human hepatocytes stability assay described above.

TABLE 5

| Compound No. | $CL_{int}$ (µL/min/ million cells) | Extraction Ratio (ER) |
|---|---|---|
| 1 | 31 | 0.82 |
| 2 | 53 | 0.89 |
| 3 | 50 | 0.88 |
| 4 | 57 | 0.89 |
| 5 | 49 | 0.88 |
| 6 | 44 | 0.87 |
| 7 | 39 | 0.85 |
| 8 | 30 | 0.82 |
| 9 | 45 | 0.87 |
| 10 | 73 | 0.92 |
| 11 | 21 | 0.76 |
| 12 | 35 | 0.84 |
| 13 | 16 | 0.71 |
| 14 | 22 | 0.77 |
| 15 | 64 | 0.91 |
| 16 | 43 | 0.87 |
| 17 | 32 | 0.83 |
| 18 | 36 | 0.84 |
| 19 | 93 | 0.93 |
| 20 | 60 | 0.90 |
| 21 | 101 | 0.94 |
| 22 | 56 | 0.89 |
| 23 | 25 | 0.79 |
| 24 | 42 | 0.86 |
| 25 | 73 | 0.92 |
| 26 | 55 | 0.89 |
| 27 | 75 | 0.92 |
| 28 | 154 | 0.96 |
| 29 | 30 | 0.82 |
| 30 | 45 | 0.87 |
| 31 | 81 | 0.92 |
| 32 | 110 | 0.94 |
| 33 | 79 | 0.92 |
| 35 | 102 | 0.94 |
| 36 | 58 | 0.90 |
| 37 | 99 | 0.94 |
| 38 | 91 | 0.93 |
| 39 | 59 | 0.90 |
| 40 | 86 | 0.93 |
| 41 | 107 | 0.94 |

TABLE 5-continued

| Compound No. | $CL_{int}$ (µL/min/ million cells) | Extraction Ratio (ER) |
|---|---|---|
| 42 | 100 | 0.94 |
| 43 | 102 | 0.94 |
| 44 | 133 | 0.95 |
| 45 | 103 | 0.94 |
| Reference Compound A | 76 | 0.92 |

Example 5: Assessment of Wake Promotion in Sprague-Dawley Rats

Wake promotion was assessed using electroencephalography (EEG) and electromyography (EMG) in adult male Sprague-Dawley rats. All rats (Charles River Laboratories, Raleigh, N.C., USA) were intraperitoneally implanted with telemetry devices (F50-EEE, Data Sciences International Inc., MN, USA) under isoflurane anesthesia. For EEG, stainless steel screws were implanted over frontal cortex and parietal cortex, and reference screws were placed over cerebellum. Additionally, an electrode was placed in neck muscle for EMG. Rats were given carprofen post-surgery and underwent a 7 to 10-day recovery period. Rats habituated to the experimental room for 7 days and were maintained on a 12-hour light-dark cycle.

EEG and EMG data were recorded using the DSI telemetry system and Ponemah software (Data Sciences International Inc., MN, USA). Sleep-wake stages were scored both manually and with Somnivore, a supervised machine learning software platform, in 10 second epochs. Records were visually inspected as needed post-processing.

All test compounds were dissolved in 5% DMSO and suspended in 95% saline with 0.5% methylcellulose and 0.5% tween. In a cross-over design, rats were dosed during the inactive light phase at zeitgeber time 5 (ZT5) at a dose volume of 3.33 ml/kg body weight. Unless otherwise indicated, all compounds were dosed orally. Recordings for each rat were initiated immediately after dosing and lasted for 6 hours post-dose.

Two key endpoints include wakefulness time and cortical activation time. Wakefulness time is derived from the sleep-wake stage analysis. Cortical activation time is based on the duration in which frontal gamma oscillatory activity (30-100 Hz), a key feature of wakefulness, was elevated relative to a pre-treatment baseline. Mean cortical activation time was computed relative to vehicle treatment for the 6-hour post-dose period. Results are shown in Table 6 below.

TABLE 6

| Compound | Route | Dose (mpk) | Mean cortical activation time (% vehicle treatment) |
|---|---|---|---|
| 53 | PO | 3 | 105.00 |
| Reference Compound A | SC | 3 | 118.75 |

PO (oral); SC (subcutaneous); mpk (milligram per kilogram)

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound of Formula I or a pharmaceutically acceptable salt thereof:

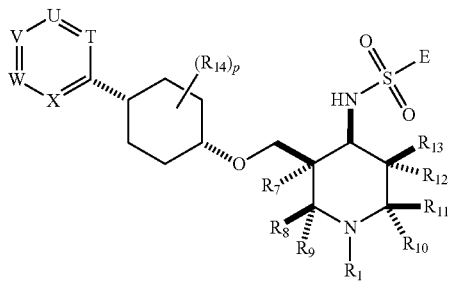

(I)

wherein:
T is CR$_6$ or N;
U is CR$_5$ or N;
V is CR$_4$ or N;
W is CR$_3$ or N;
X is CR$_2$ or N;
and provided that

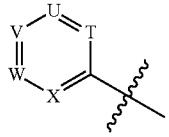

includes no more than 3 nitrogen atoms in the ring;
E is selected from the group consisting of NR$_a$R$_b$, C$_1$-C$_3$ alkylene-NR$_a$R$_b$, C$_1$-C$_3$ alkyl, C$_2$-C$_4$ alkenyl, C$_2$-C$_4$ alkynyl, C$_3$-C$_8$ cycloalkyl, C$_1$-C$_3$ alkylene-(C$_3$-C$_8$ cycloalkyl), 4- to 10-membered heterocyclyl, and C$_1$-C$_3$ alkylene-(4- to 10-membered heterocyclyl) wherein the C$_1$-C$_3$ alkylene-NR$_a$R$_b$, C$_1$-C$_3$ alkyl, C$_2$-C$_4$ alkenyl, C$_2$-C$_4$ alkynyl, C$_3$-C$_8$ cycloalkyl, C$_1$-C$_3$ alkylene-(C$_3$-C$_8$ cycloalkyl), 4- to 10-membered heterocyclyl, or C$_1$-C$_3$ alkylene-(4- to 10-membered heterocyclyl) is unsubstituted or substituted with one or more halogen, hydroxyl, C$_1$-C$_3$ alkyl, or C$_1$-C$_3$ alkoxyl;
R$_a$ and R$_b$ are each, independently, H or unsubstituted C$_1$-C$_3$ alkyl;
R$_1$ is (CR$_c$R$_d$)$_n$—(C$_6$-C$_{10}$ aryl) or (CR$_c$R$_d$)$_n$-(5- to 10-membered heteroaryl) wherein the aryl or heteroaryl is unsubstituted or substituted with one or more halogen, hydroxyl, unsubstituted C$_1$-C$_3$ alkyl, or C$_1$-C$_3$ alkyl substituted with one or more halogen or deuterium;
R$_c$ and R$_d$ are each, independently, H, unsubstituted C$_1$-C$_3$ alkyl, or C$_1$-C$_3$ alkyl substituted with one or more halogen or deuterium;
n is 0 or 1;
each of R$_2$, R$_3$, R$_4$, R$_5$, and R$_6$, when present, is, independently, selected from the group consisting of H, halogen, deuterium, hydroxyl, cyano, unsubstituted C$_1$-C$_3$alkyl, and C$_1$-C$_3$alkyl substituted with one or more halogen or deuterium;

each of R$_7$, R$_8$, R$_9$, R$_{10}$, R$_{11}$, R$_{12}$, and R$_{13}$ is, independently, H, halogen, unsubstituted C$_1$-C$_3$ alkyl, or C$_1$-C$_3$ alkyl substituted with one or more halogen or deuterium;
or, alternatively, R$_8$ and R$_{11}$, together form an unsubstituted C$_1$-C$_3$ alkylene or a C$_1$-C$_3$ alkylene substituted with one or more halogen;
or, alternatively, R$_9$ and R$_{10}$, together form an unsubstituted C$_1$-C$_3$ alkylene or a C$_1$-C$_3$ alkylene substituted with one or more halogen;
p is 0, 1, 2, 3, or 4; and
each R$_{14}$ is, independently, selected from the group consisting of deuterium, halogen, hydroxyl, and cyano.

2. The compound of claim 1, wherein

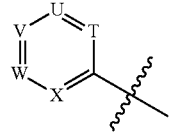

is selected from the group consisting of:

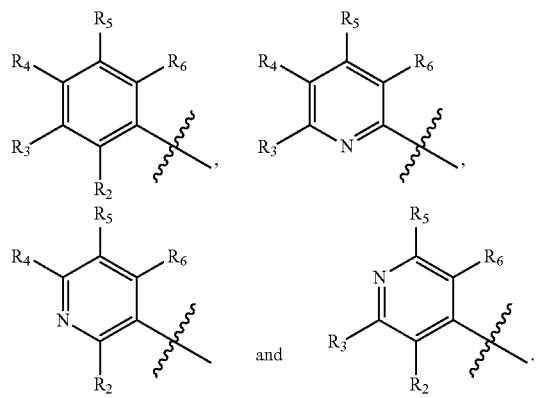

3. The compound of claim 1, wherein

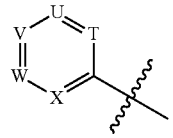

is selected from the group consisting of:

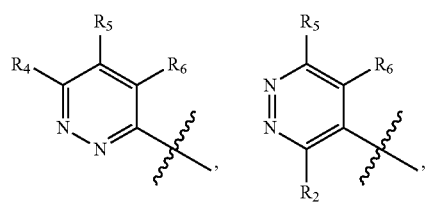

-continued

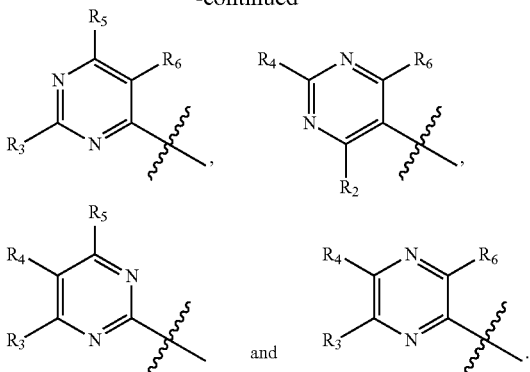

4. The compound of claim 1, wherein

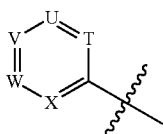

is selected from the group consisting of:

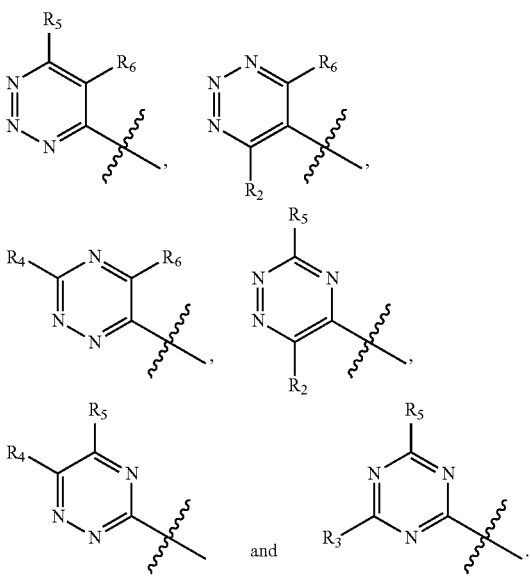

5. The compound of claim 1, wherein

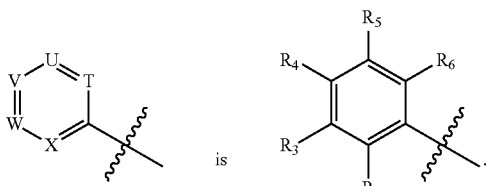

6. The compound of claim 1, wherein p is 0.
7. The compound of claim 1, wherein p is 1 or 2.
8. The compound of claim 1, wherein E is $NR_aR_b$.

9. The compound of claim 1, wherein E is $C_1$-$C_3$ alkylene-$NR_aR_b$.
10. The compound of claim 1, wherein E is unsubstituted $C_1$-$C_3$ alkyl, unsubstituted $C_2$-$C_4$ alkenyl, or unsubstituted $C_2$-$C_4$ alkynyl.
11. The compound of claim 1, wherein E is $C_1$-$C_3$ alkyl, $C_2$-$C_4$ alkenyl or $C_2$-$C_4$ alkynyl substituted with one or more halogen, hydroxyl, $C_1$-$C_3$ alkyl, or $C_1$-$C_3$ alkoxyl.
12. The compound of claim 1, wherein E is unsubstituted $C_1$-$C_3$ alkyl.
13. The compound of claim 1, wherein E is $C_1$-$C_3$ alkyl substituted with one or more halogen, hydroxyl, $C_1$-$C_3$ alkyl, or $C_1$-$C_3$ alkoxyl.
14. The compound of claim 1, wherein E is unsubstituted $C_3$-$C_8$ cycloalkyl, substituted $C_3$-$C_8$ cycloalkyl, unsubstituted $C_1$-$C_3$ alkylene-($C_3$-$C_8$ cycloalkyl), substituted $C_1$-$C_3$ alkylene-($C_3$-$C_8$ cycloalkyl), unsubstituted 4- to 10-membered heterocyclyl, substituted 4- to 10-membered heterocyclyl, unsubstituted $C_1$-$C_3$ alkylene-(4- to 10-membered heterocyclyl), or substituted $C_1$-$C_3$ alkylene-(4- to 10-membered heterocyclyl).
15. The compound of claim 1, wherein $R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted.
16. The compound of claim 1, wherein $R_1$ is $(CR_cR_d)_n$—($C_6$-$C_{10}$ aryl) or $(CR_cR_d)_n$-(5- to 10-membered heteroaryl) wherein the aryl or heteroaryl is substituted with one or more halogen, hydroxyl, unsubstituted $C_1$-$C_3$ alkyl, or $C_1$-$C_3$ alkyl substituted with one or more halogen or deuterium.
17. The compound of claim 1, wherein $R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted and further wherein n is 0.
18. The compound of claim 1, wherein $R_1$ is $(CR_cR_d)_n$—($C_6$-$C_{10}$ aryl) or $(CR_cR_d)_n$-(5- to 10-membered heteroaryl) wherein the aryl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 0.
19. The compound of claim 1, wherein $R_1$ is $(CR_cR_d)_n$—($C_6$-$C_{10}$ aryl) or $(CR_cR_d)_n$-(5- to 10-membered heteroaryl) wherein the aryl or heteroaryl is unsubstituted and further wherein n is 1.
20. The compound of claim 1, wherein $R_1$ is $(CR_cR_d)_n$—($C_6$-$C_{10}$ aryl) or $(CR_cR_d)_n$-(5- to 10-membered heteroaryl) wherein the aryl or heteroaryl is substituted with one or more halogen, hydroxyl, unsubstituted $C_1$-$C_3$ alkyl, or $C_1$-$C_3$ alkyl substituted with one or more halogen or deuterium and further wherein n is 1.
21. The compound of claim 1, wherein $R_1$ is $(CR_cR_d)_n$—($C_6$-$C_{10}$ aryl) wherein the aryl is unsubstituted.
22. The compound of claim 1, wherein $R_1$ is $(CR_cR_d)_n$—($C_6$-$C_{10}$ aryl) wherein the aryl is substituted with one or more halogen, hydroxyl, unsubstituted $C_1$-$C_3$ alkyl, or $C_1$-$C_3$ alkyl substituted with one or more halogen or deuterium.
23. The compound of claim 1, wherein $R_1$ is $(CR_cR_d)_n$—($C_6$-$C_{10}$ aryl) wherein the aryl is unsubstituted and further wherein n is 0.
24. The compound of claim 1, wherein $R_1$ is $(CR_cR_d)_n$—($C_6$-$C_{10}$ aryl) wherein the aryl is substituted with one or more halogen, hydroxyl, unsubstituted $C_1$-$C_3$ alkyl, or $C_1$-$C_3$ alkyl substituted with one or more halogen or deuterium and further wherein n is 0.
25. The compound of claim 1, wherein $R_1$ is $(CR_cR_d)_n$-(5- to 10-membered heteroaryl) wherein the heteroaryl is unsubstituted, $(CR_cR_d)_n$-(5- to 10-membered heteroaryl) wherein the heteroaryl is substituted with one or more halogen, hydroxyl, unsubstituted C₁-C₃ alkyl, or C₁-C₃ alkyl substituted with one or more halogen or deuterium, (CR$_c$R$_d$)$_n$-(5- to 10-membered heteroaryl) wherein the heteroaryl is unsubstituted and further wherein n is 0, or (CR$_c$R$_d$)$_n$-(5- to 10-membered heteroaryl) wherein the heteroaryl is substituted with one or more halogen, hydroxyl, unsubstituted C₁-C₃ alkyl, or C₁-C₃ alkyl substituted with one or more halogen or deuterium and further wherein n is 0.

26. The compound of claim 1, wherein R₁ is (CR$_c$R$_d$)$_n$-(phenyl) or (CR$_c$R$_d$)$_n$-(5- to 7-membered heteroaryl) wherein the phenyl or heteroaryl is unsubstituted.

27. The compound of claim 1, wherein R₁ is (CR$_c$R$_d$)$_n$-(phenyl) or (CR$_c$R$_d$)$_n$-(5- to 7-membered heteroaryl) wherein the phenyl or heteroaryl is substituted with one or more halogen, hydroxyl, unsubstituted C₁-C₃ alkyl, or C₁-C₃ alkyl substituted with one or more halogen or deuterium.

28. The compound of claim 1, wherein R₁ is (CR$_c$R$_d$)$_n$-(phenyl) or (CR$_c$R$_d$)$_n$-(5- to 7-membered heteroaryl) wherein the phenyl or heteroaryl is unsubstituted and further wherein n is 0.

29. The compound of claim 1, wherein R₁ is (CR$_c$R$_d$)$_n$-(phenyl) or (CR$_c$R$_d$)$_n$-(5- to 7-membered heteroaryl) wherein the phenyl or heteroaryl is substituted with one or more halogen, hydroxyl, unsubstituted C₁-C₃ alkyl, or C₁-C₃ alkyl substituted with one or more halogen or deuterium and further wherein n is 0.

30. The compound of claim 1, wherein R₁ is (CR$_c$R$_d$)$_n$-(phenyl) or (CR$_c$R$_d$)$_n$-(6-membered heteroaryl) wherein the phenyl or heteroaryl is unsubstituted.

31. The compound of claim 1, wherein R₁ is (CR$_c$R$_d$)$_n$-(phenyl) or (CR$_c$R$_d$)$_n$-(6-membered heteroaryl) wherein the phenyl or heteroaryl is substituted with one or more halogen, hydroxyl, unsubstituted C₁-C₃ alkyl, or C₁-C₃ alkyl substituted with one or more halogen or deuterium.

32. The compound of claim 1, wherein R₁ is (CR$_c$R$_d$)$_n$-(phenyl) or (CR$_c$R$_d$)$_n$-(6-membered heteroaryl) wherein the phenyl or heteroaryl is unsubstituted and further wherein n is 0.

33. The compound of claim 1, wherein R₁ is (CR$_c$R$_d$)$_n$-(phenyl) or (CR$_c$R$_d$)$_n$-(6-membered heteroaryl) wherein the phenyl or heteroaryl is substituted with one or more halogen, hydroxyl, unsubstituted C₁-C₃ alkyl, or C₁-C₃ alkyl substituted with one or more halogen or deuterium and further wherein n is 0.

34. The compound of claim 1, wherein each of R₂, R₃, R₄, R₅, and R₆, when present, is H and each of R₇, R₈, R₉, R₁₀, R₁₁, R₁₂, and R₁₃ is H.

35. The compound of claim 1, wherein each of R₂, R₃, R₄, R₅, and R₆, when present, is H and each of R₇, R₈, R₉, R₁₀, R₁₁, R₁₂, and R₁₃ is H or unsubstituted C₁-C₃ alkyl.

36. The compound of claim 1, wherein each of R₂, R₃, R₄, R₅, and R₆, when present, is H and each of R₇, R₈, R₉, R₁₀, R₁₁, R₁₂, and R₁₃ is H or fluorine.

37. The compound of claim 1, wherein R₁ is (CR$_c$R$_d$)$_n$-(5- to 10-membered heteroaryl), each of R₂, R₃, R₄, R₅, and R₆, when present, is H, and each of R₇, R₈, R₉, R₁₀, R₁₁, R₁₂, and R₁₃ is H.

38. The compound of claim 1, wherein R₁ is (CR$_c$R$_d$)$_n$-(5- to 10-membered heteroaryl), each of R₂, R₃, R₄, R₅, and R₆, when present, is H, and each of R₇, R₈, R₉, R₁₀, R₁₁, R₁₂, and R₁₃ is H or unsubstituted C₁-C₃ alkyl.

39. The compound of claim 1, wherein R₁ is (CR$_c$R$_d$)$_n$-(5- to 10-membered heteroaryl), each of R₂, R₃, R₄, R₅, and R₆, when present, is H and each of R₇, R₈, R₉, R₁₀, R₁₁, R₁₂, and R₁₃ is H or fluorine.

40. The compound of claim 1, wherein R₁ is (CR$_c$R$_d$)$_n$-(5- to 7-membered heteroaryl), each of R₂, R₃, R₄, R₅, and R₆, when present, is H, and each of R₇, R₈, R₉, R₁₀, R₁₁, R₁₂, and R₁₃ is independently H, unsubstituted C₁-C₃ alkyl, or fluorine.

41. The compound of claim 1, wherein R₁ is (CR$_c$R$_d$)$_n$—(C₆-C₁₀ aryl), each of R₂, R₃, R₄, R₅, and R₆, when present, is H, and each of R₇, R₈, R₉, R₁₀, R₁₁, R₁₂, and R₁₃ is H.

42. The compound of claim 1, wherein R₁ is (CR$_c$R$_d$)$_n$—(C₆-C₁₀ aryl), each of R₂, R₃, R₄, R₅, and R₆, when present, is H, and each of R₇, R₈, R₉, R₁₀, R₁₁, R₁₂, and R₁₃ is H or unsubstituted C₁-C₃ alkyl.

43. The compound of claim 1, wherein R₁ is (CR$_c$R$_d$)$_n$—(C₆-C₁₀ aryl), each of R₂, R₃, R₄, R₅, and R₆, when present, is H and each of R₇, R₈, R₉, R₁₀, R₁₁, R₁₂, and R₁₃ is H or fluorine.

44. The compound of claim 1, wherein R₁ is (CR$_c$R$_d$)$_n$—(C₆ aryl), each of R₂, R₃, R₄, R₅, and R₆, when present, is H, and each of R₇, R₈, R₉, R₁₀, R$_u$, R$_{ia}$, and R₁₃ is independently H, unsubstituted C₁-C₃ alkyl, or fluorine.

45. The compound of claim 1, wherein the compound or a pharmaceutically acceptable salt thereof is selected from the group consisting of:

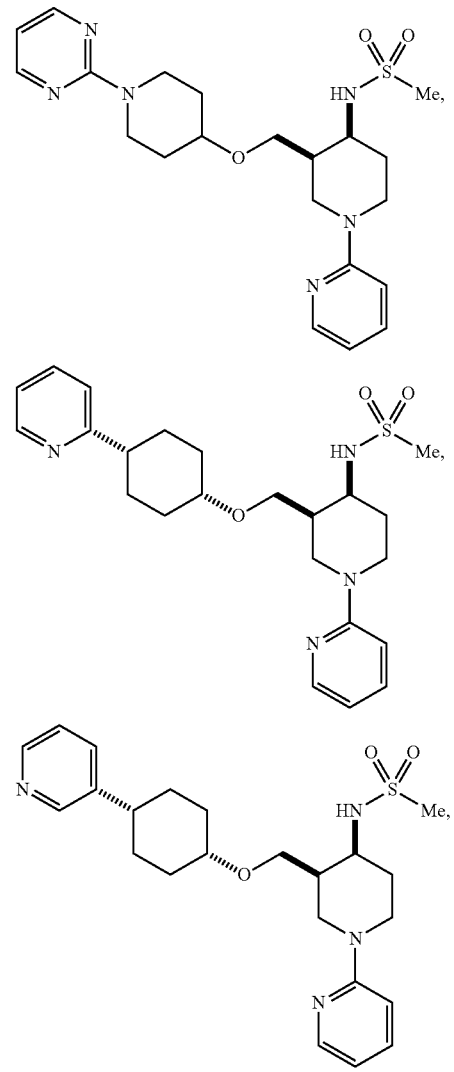

105
-continued
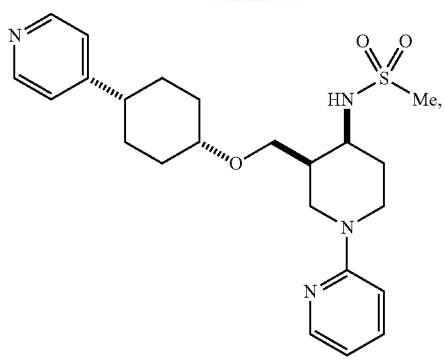
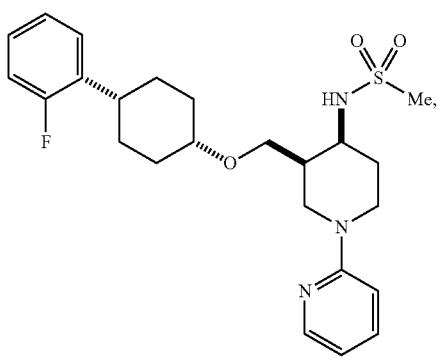
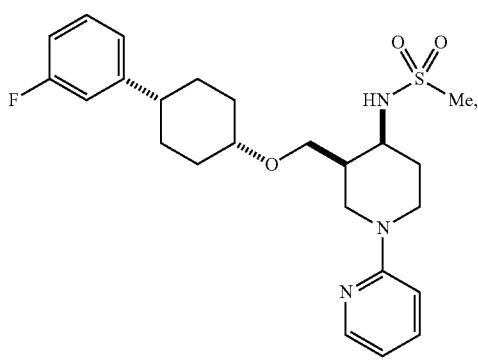
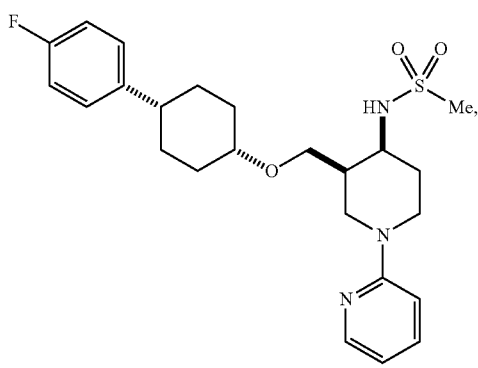
106
-continued
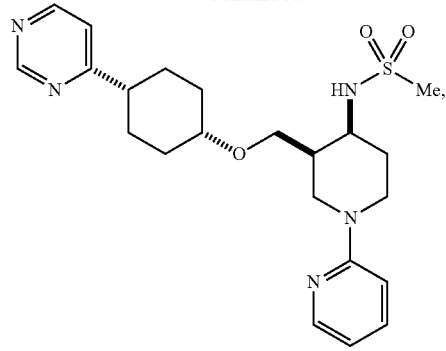
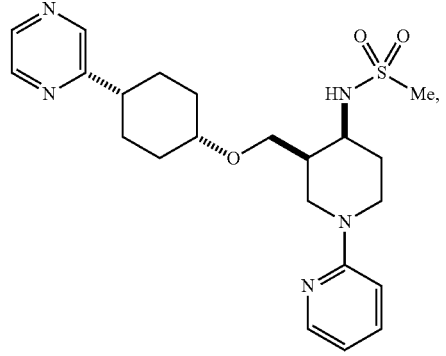
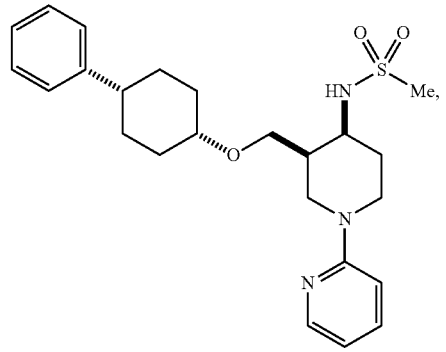
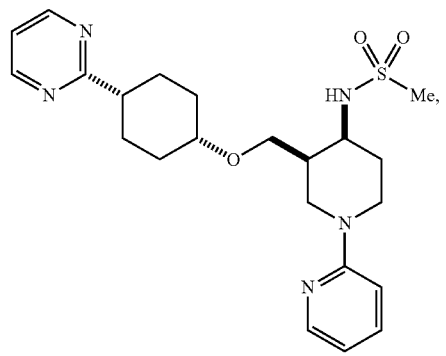

107
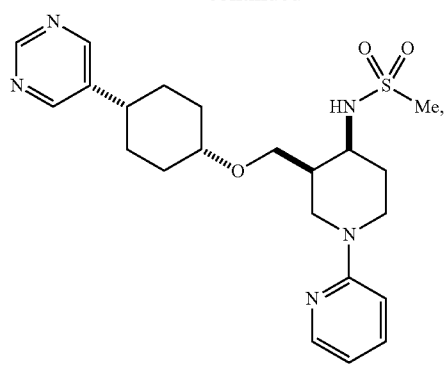
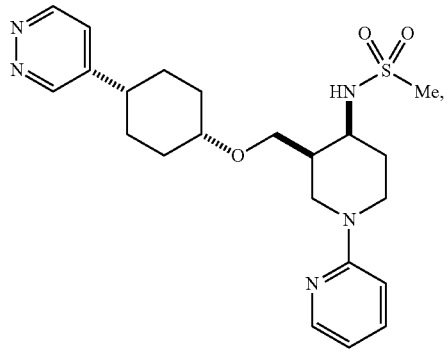
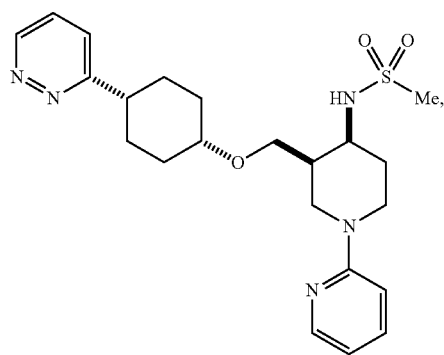
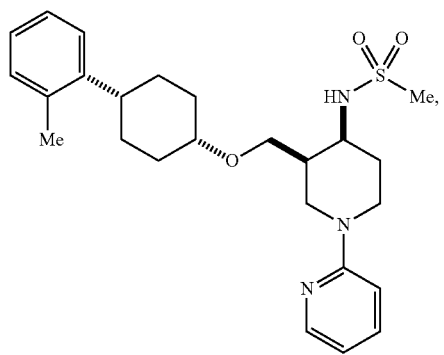
108
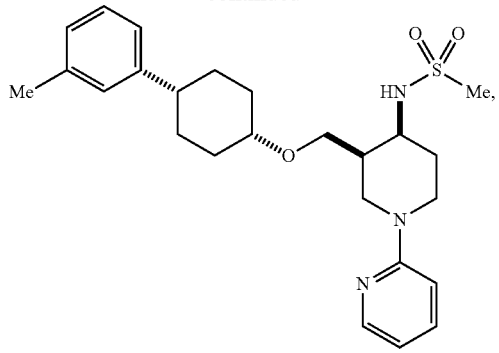
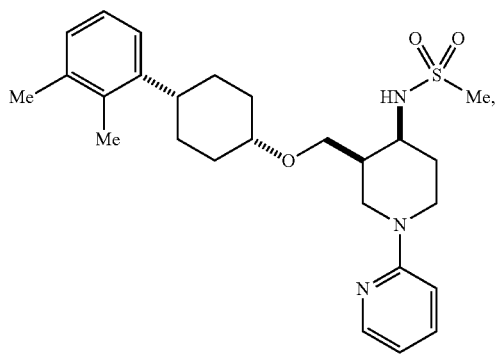
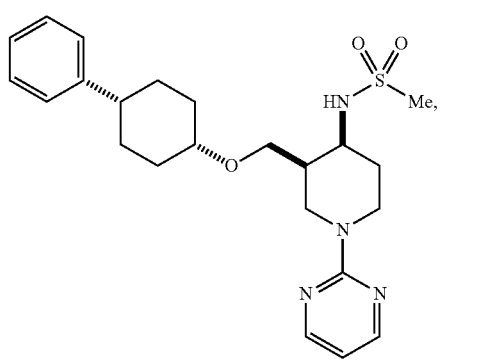

109
-continued
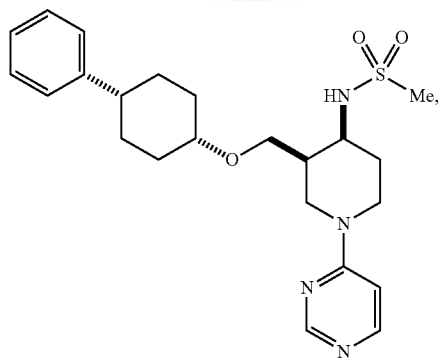
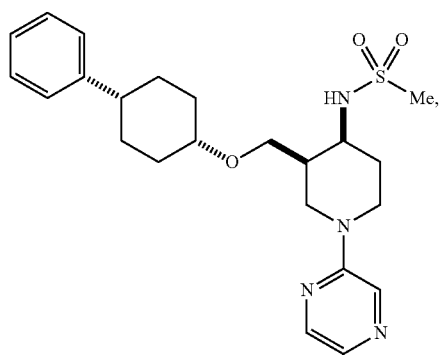
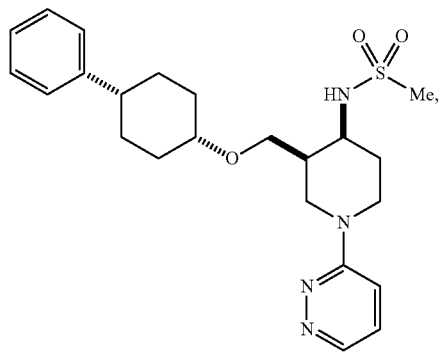
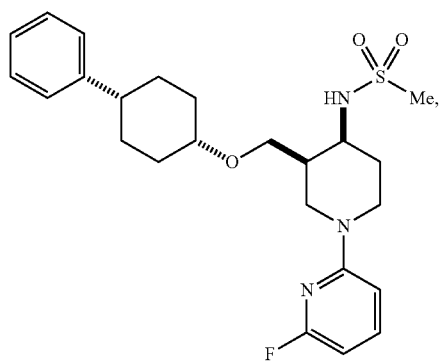
110
-continued
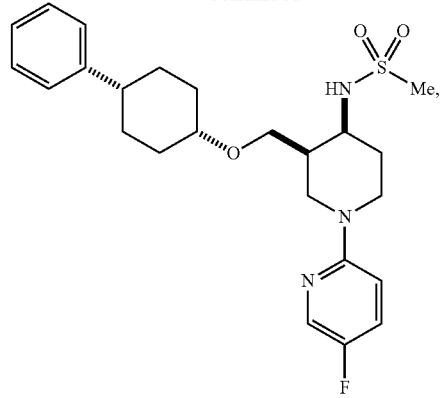
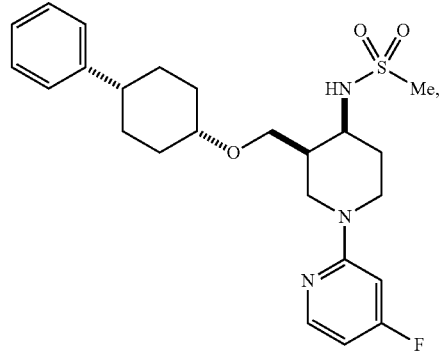
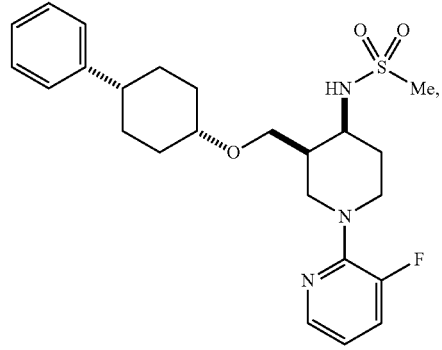
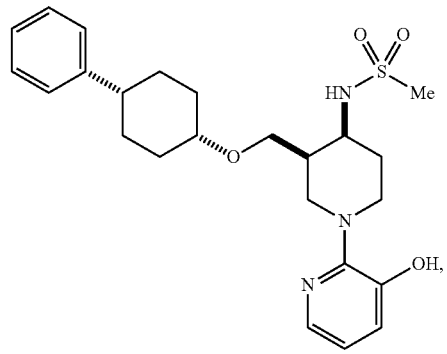

111
-continued
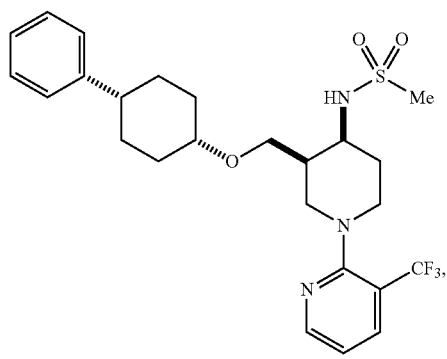
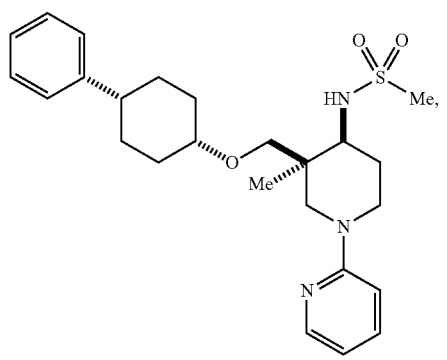
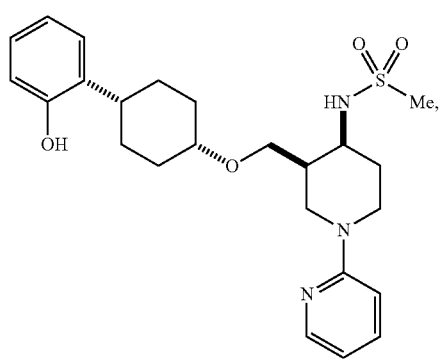
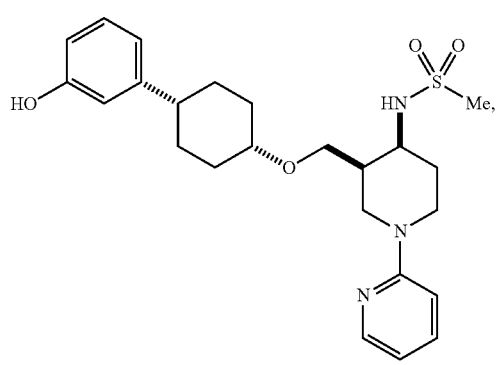
112
-continued
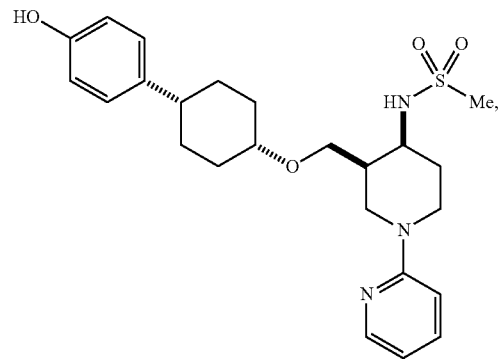
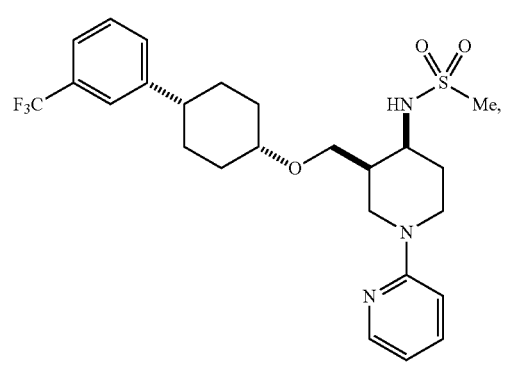
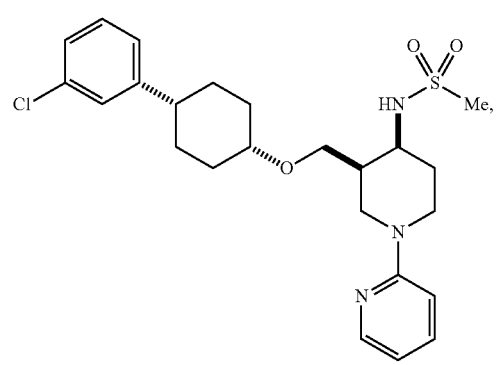
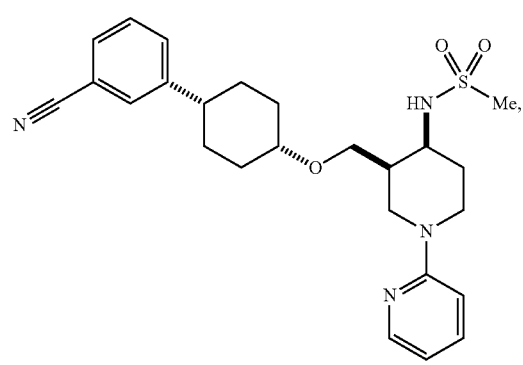

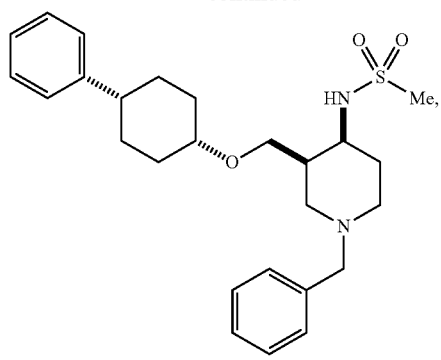
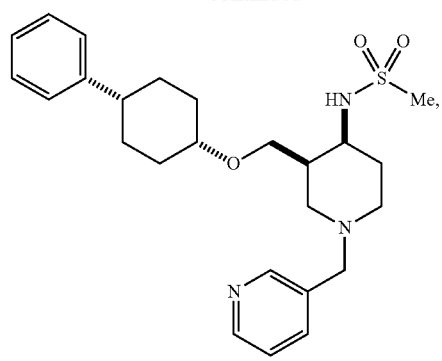
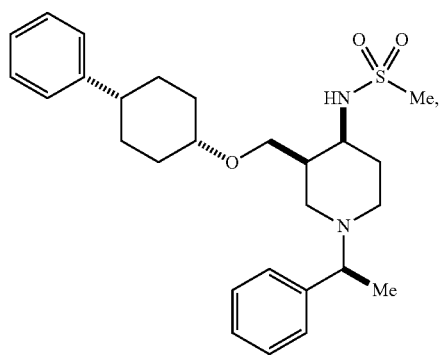
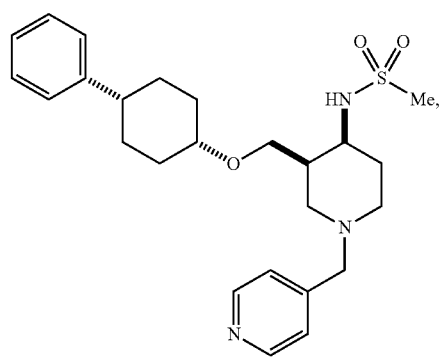
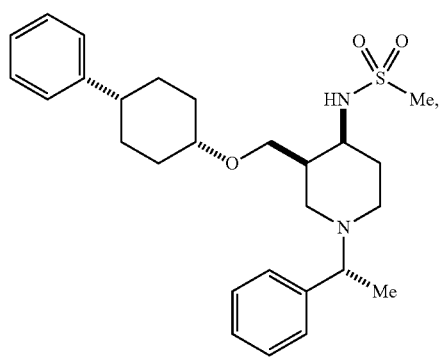
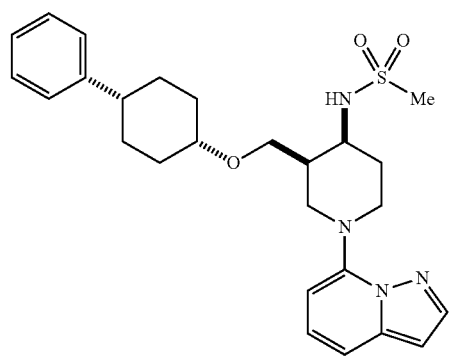
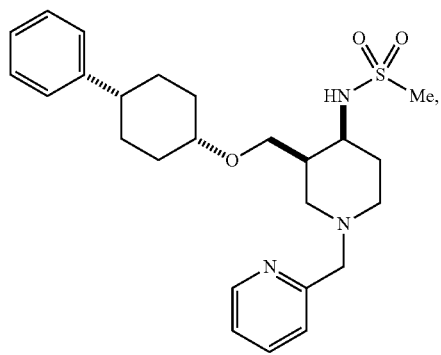
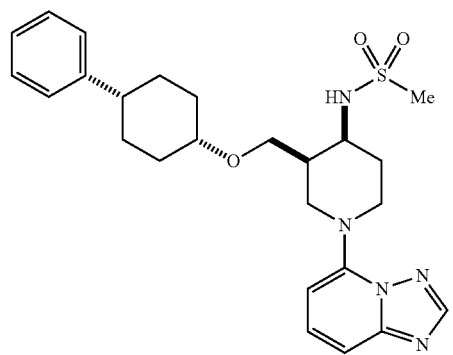

115
-continued
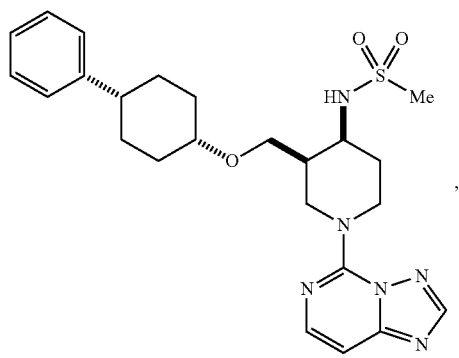
,
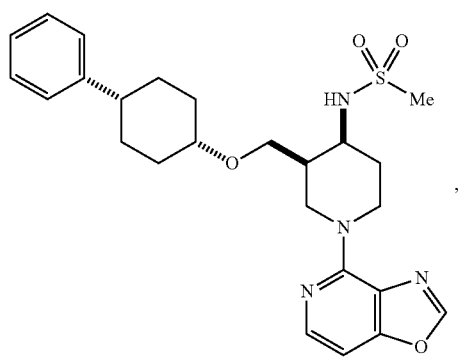
,
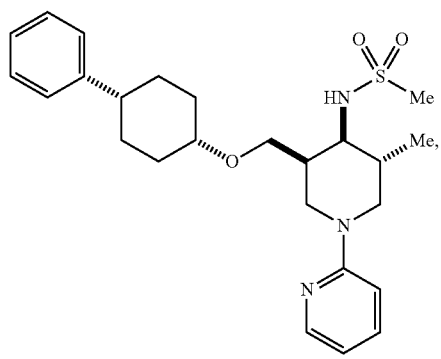
,
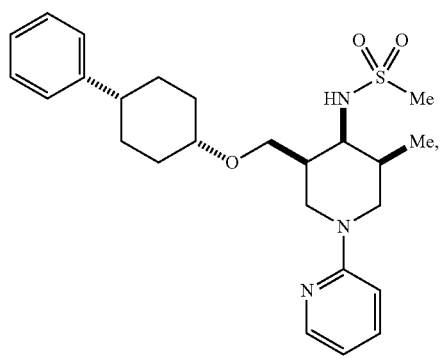
,
116
-continued
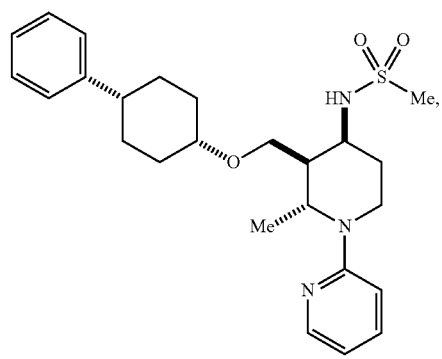
,
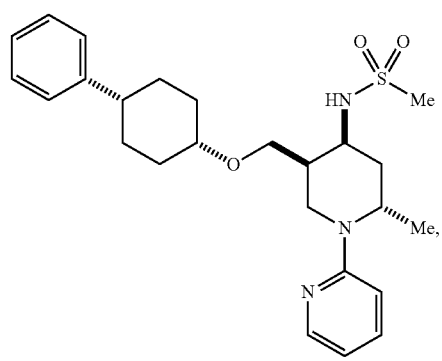
,
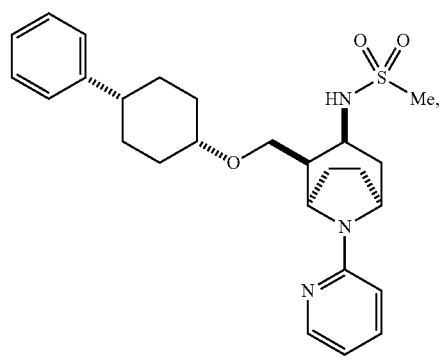
,
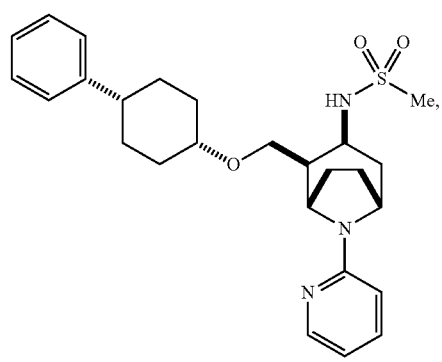
, 117
-continued 118
-continued 119
-continued
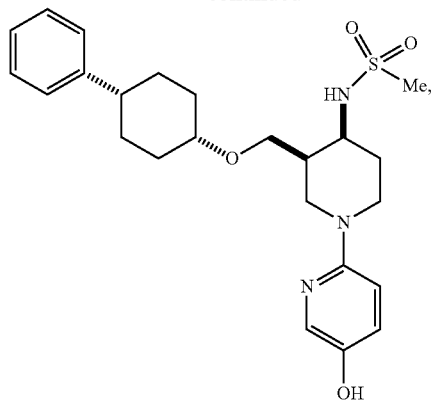
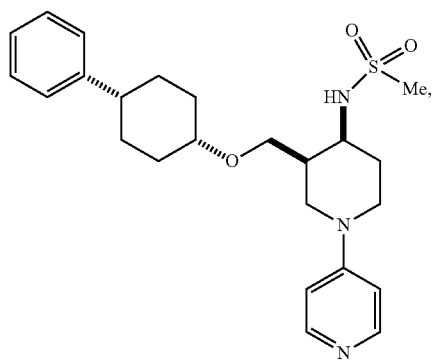
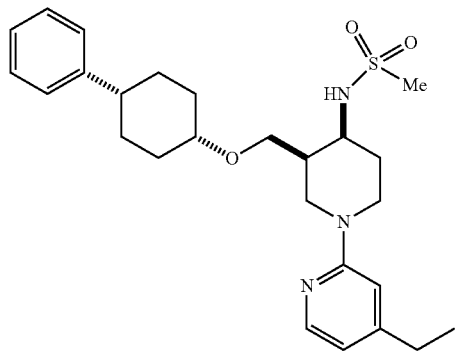
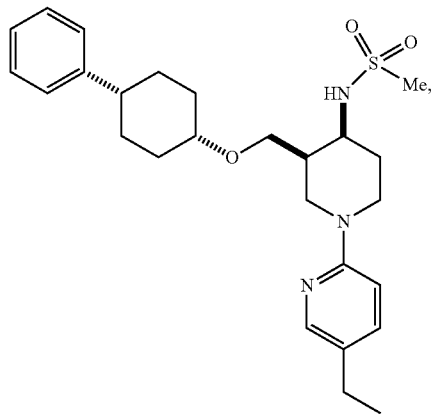
120
-continued
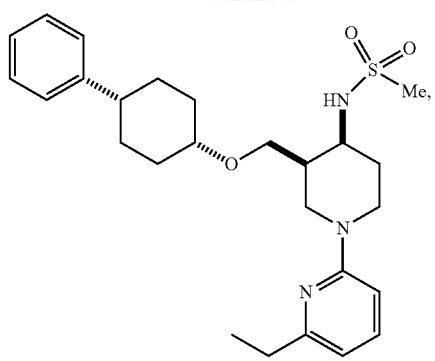
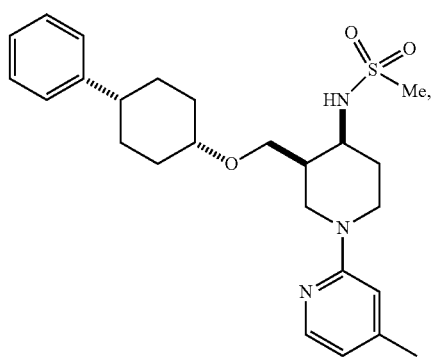
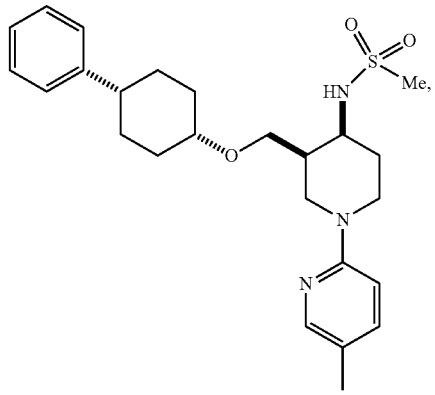
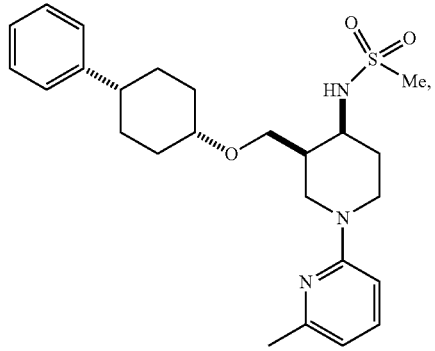

-continued

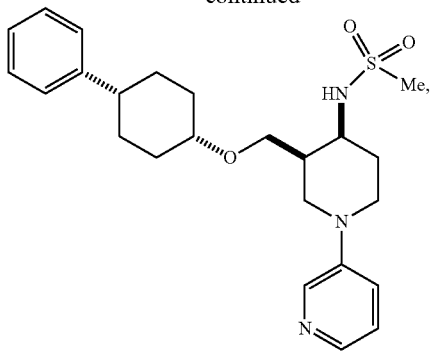

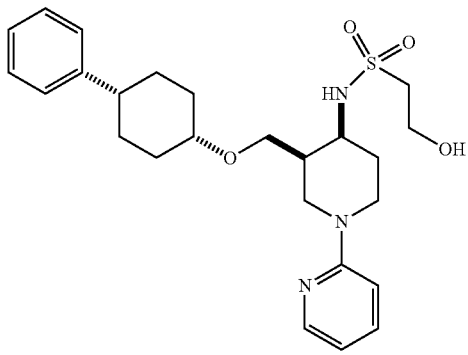

and

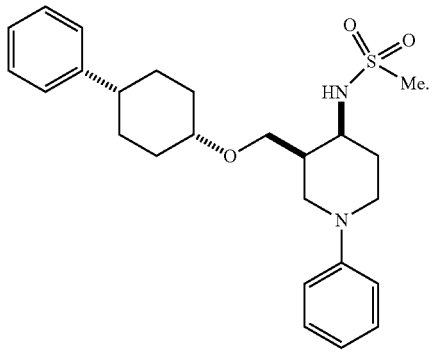

46. A pharmaceutical composition comprising a compound of claim 1 or a pharmaceutically acceptable salt thereof, and a pharmaceutically acceptable carrier.

47. A method of treating narcolepsy in a subject in need thereof comprising administering to the subject a compound of claim 1 or a pharmaceutically acceptable salt thereof, or a composition according to claim 46.

48. A method of treating cataplexy in a subject in need thereof comprising administering to the subject a compound of claim 1 or a pharmaceutically acceptable salt thereof, or a composition according to claim 46.

49. A pharmaceutical composition comprising a compound of claim 45 or a pharmaceutically acceptable salt thereof, and a pharmaceutically acceptable carrier.

50. A method of treating narcolepsy in a subject in need thereof comprising administering to the subject a compound of claim 45 or a pharmaceutically acceptable salt thereof, or a composition according to claim 49.

51. A method of treating cataplexy in a subject in need thereof comprising administering to the subject a compound of claim 1 or a pharmaceutically acceptable salt thereof, or a composition according to claim 49.

52. The compound of claim 1, wherein the compound is:

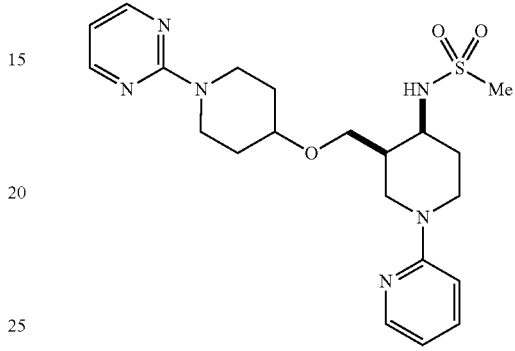

or a pharmaceutically acceptable salt thereof.

53. The compound of claim 1, wherein the compound is:

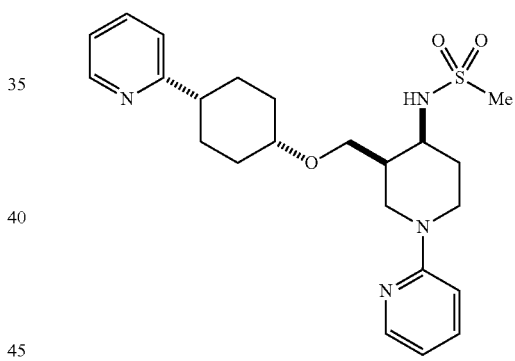

or a pharmaceutically acceptable salt thereof.

54. The compound of claim 1, wherein the compound is:

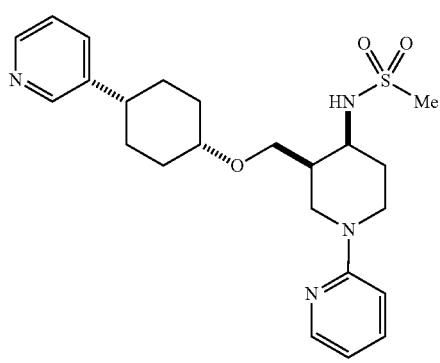

or a pharmaceutically acceptable salt thereof.

55. The compound of claim 1, wherein the compound is:

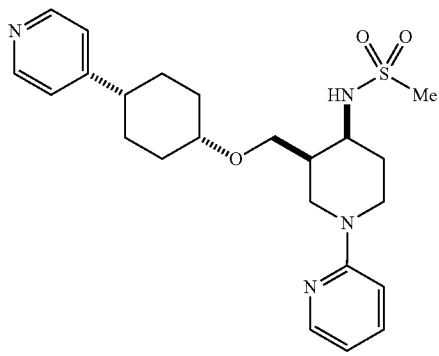

or a pharmaceutically acceptable salt thereof.

56. The compound of claim 1, wherein the compound is:

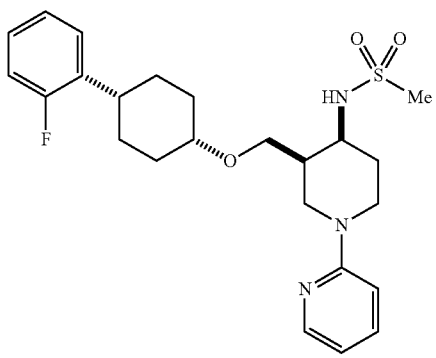

or a pharmaceutically acceptable salt thereof.

57. The compound of claim 1, wherein the compound is:

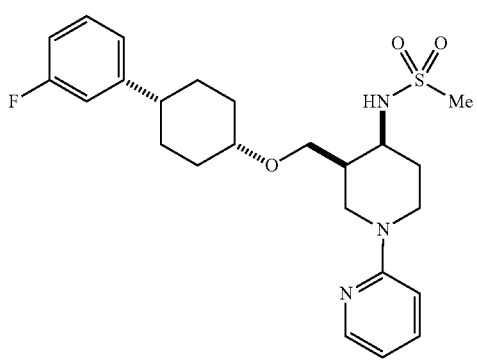

or a pharmaceutically acceptable salt thereof.

58. The compound of claim 1, wherein the compound is:

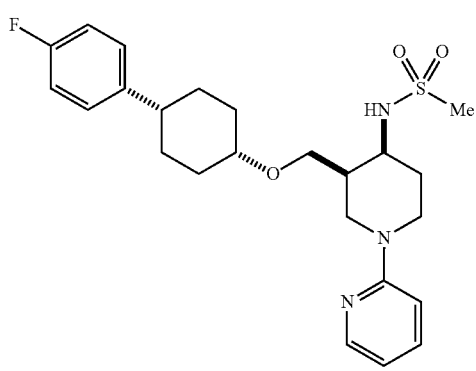

or a pharmaceutically acceptable salt thereof.

59. The compound of claim 1, wherein the compound is:

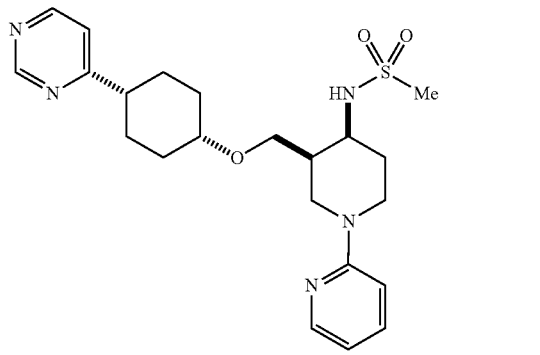

or a pharmaceutically acceptable salt thereof.

60. The compound of claim 1, wherein the compound is:

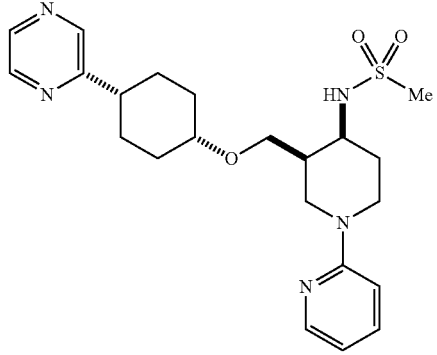

or a pharmaceutically acceptable salt thereof.

61. The compound of claim 1, wherein the compound is:

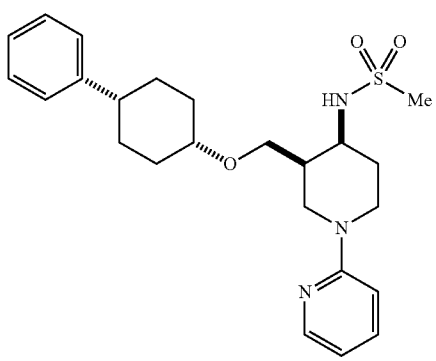

or a pharmaceutically acceptable salt thereof.

62. The compound of claim 1, wherein the compound is:

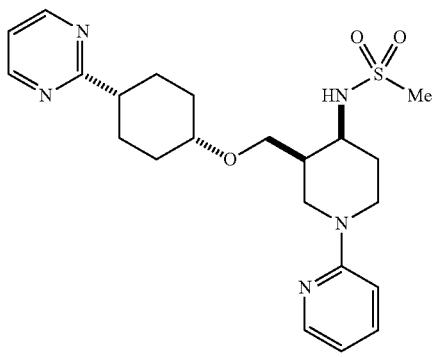

or a pharmaceutically acceptable salt thereof.

63. The compound of claim 1, wherein the compound is:

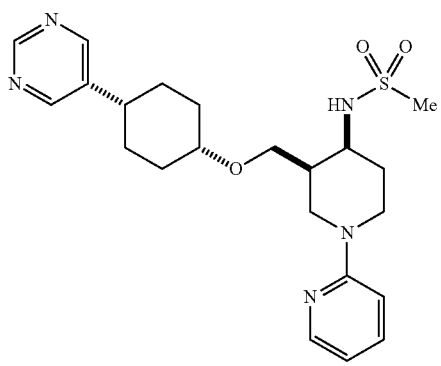

or a pharmaceutically acceptable salt thereof.

64. The compound of claim 1, wherein the compound is:

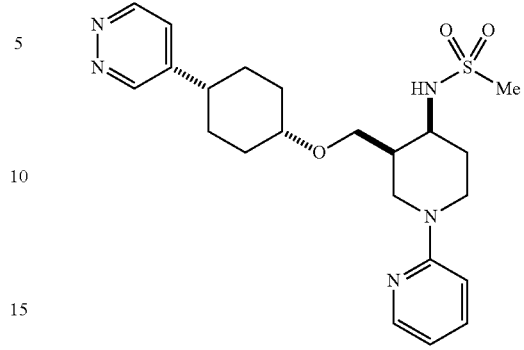

or a pharmaceutically acceptable salt thereof.

65. The compound of claim 1, wherein the compound is:

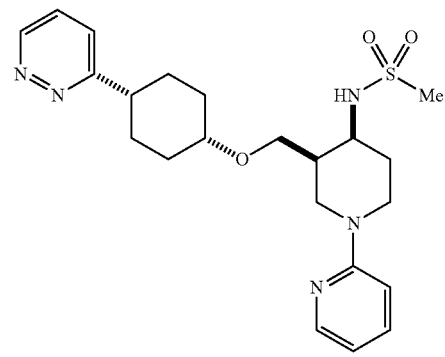

or a pharmaceutically acceptable salt thereof.

66. The compound of claim 1, wherein the compound is:

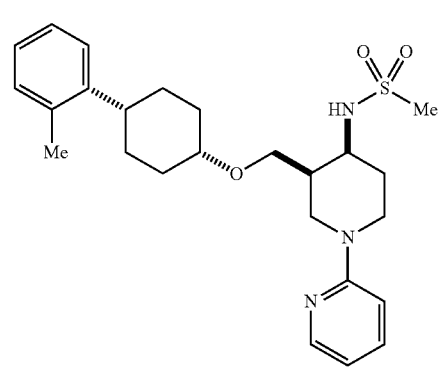

or a pharmaceutically acceptable salt thereof.

67. The compound of claim 1, wherein the compound is:

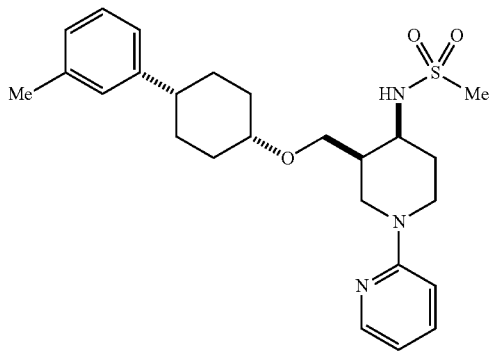

or a pharmaceutically acceptable salt thereof.

68. The compound of claim 1, wherein the compound is:

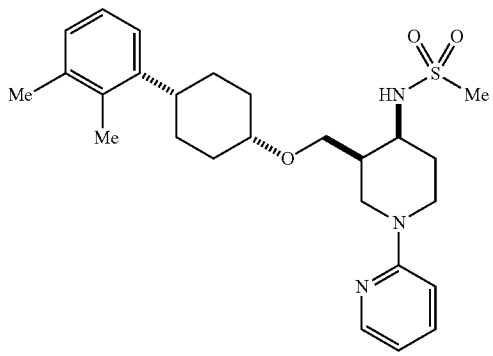

or a pharmaceutically acceptable salt thereof.

69. The compound of claim 1, wherein the compound is:

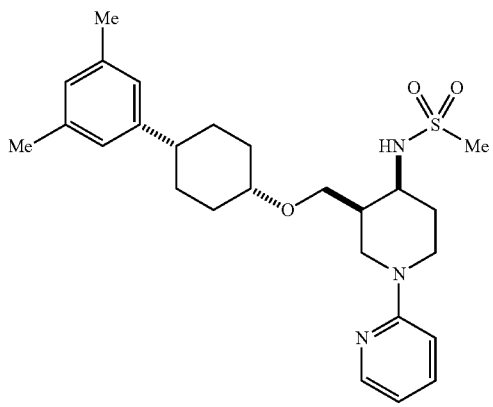

or a pharmaceutically acceptable salt thereof.

70. The compound of claim 1, wherein the compound is:

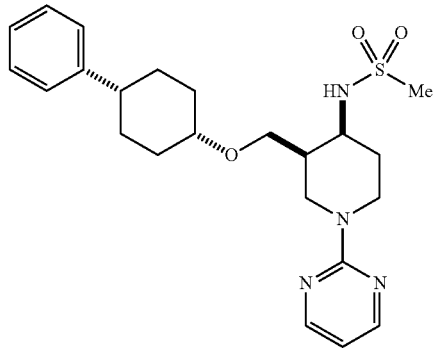

or a pharmaceutically acceptable salt thereof.

71. The compound of claim 1, wherein the compound is:

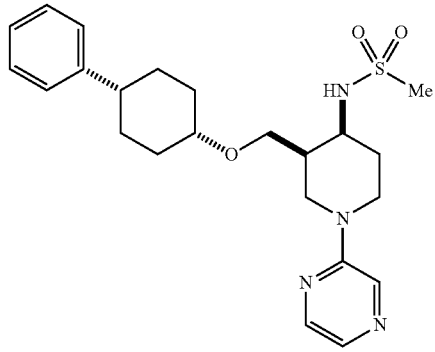

or a pharmaceutically acceptable salt thereof.

72. The compound of claim 1, wherein the compound is:

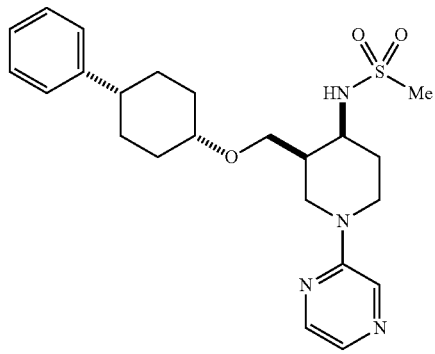

or a pharmaceutically acceptable salt thereof.

73. The compound of claim 1, wherein the compound is:

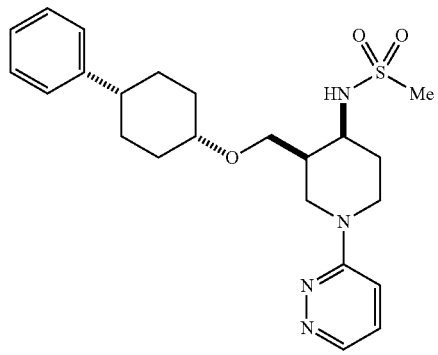

or a pharmaceutically acceptable salt thereof.

74. The compound of claim 1, wherein the compound is:

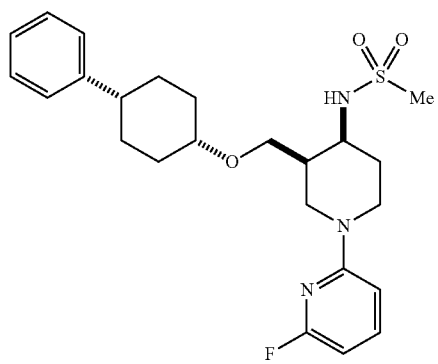

or a pharmaceutically acceptable salt thereof.

75. The compound of claim 1, wherein the compound is:

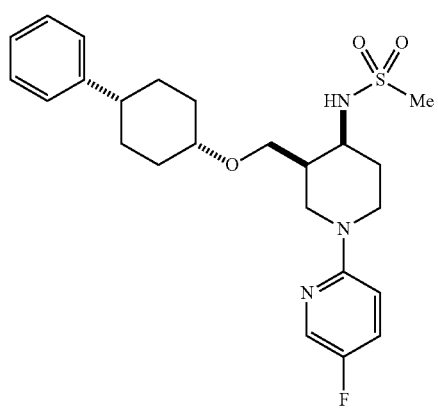

or a pharmaceutically acceptable salt thereof.

76. The compound of claim 1, wherein the compound is:

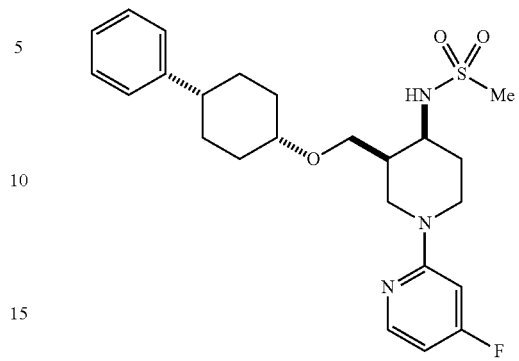

or a pharmaceutically acceptable salt thereof.

77. The compound of claim 1, wherein the compound is:

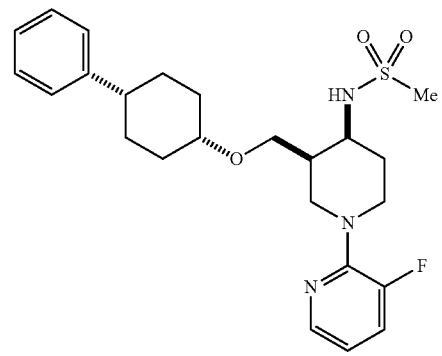

or a pharmaceutically acceptable salt thereof.

78. The compound of claim 1, wherein the compound is:

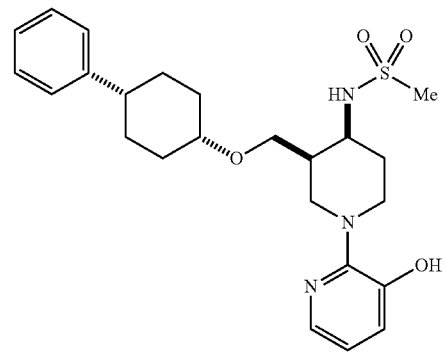

or a pharmaceutically acceptable salt thereof.

79. The compound of claim 1, wherein the compound is:

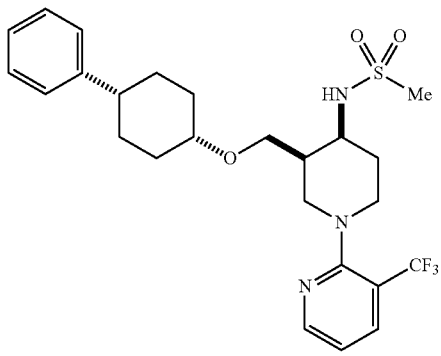

or a pharmaceutically acceptable salt thereof.

80. The compound of claim 1, wherein the compound is:

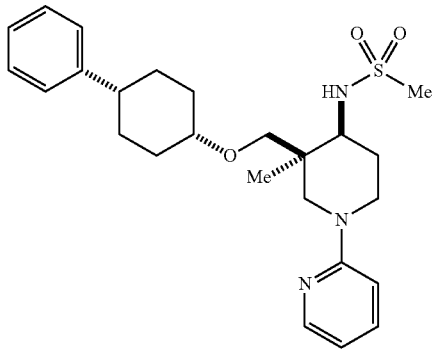

or a pharmaceutically acceptable salt thereof.

81. The compound of claim 1, wherein the compound is:

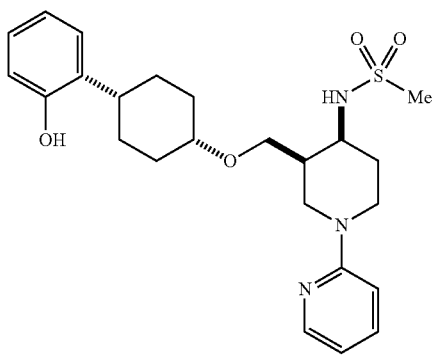

or a pharmaceutically acceptable salt thereof.

82. The compound of claim 1, wherein the compound is:

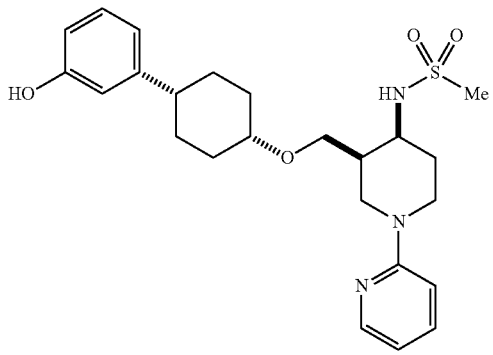

or a pharmaceutically acceptable salt thereof.

83. The compound of claim 1, wherein the compound is:

or a pharmaceutically acceptable salt thereof.

84. The compound of claim 1, wherein the compound is:

or a pharmaceutically acceptable salt thereof.

85. The compound of claim 1, wherein the compound is:

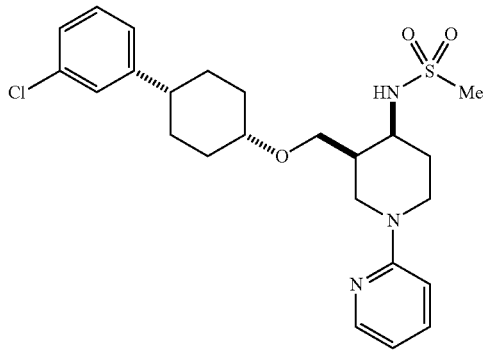

or a pharmaceutically acceptable salt thereof.

86. The compound of claim 1, wherein the compound is:

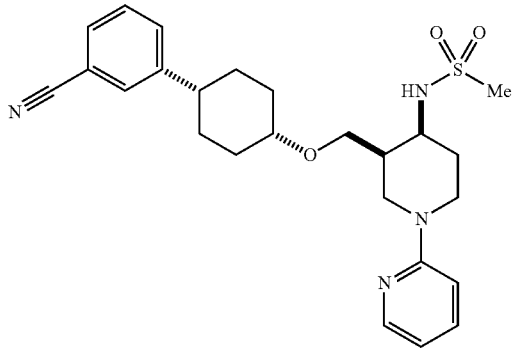

or a pharmaceutically acceptable salt thereof.

87. The compound of claim 1, wherein the compound is:

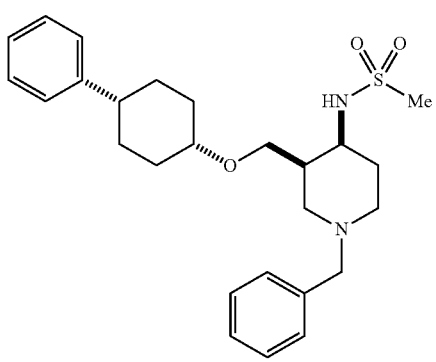

or a pharmaceutically acceptable salt thereof.

88. The compound of claim 1, wherein the compound is:

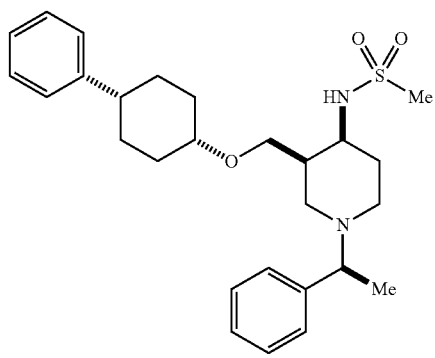

or a pharmaceutically acceptable salt thereof.

89. The compound of claim 1, wherein the compound is:

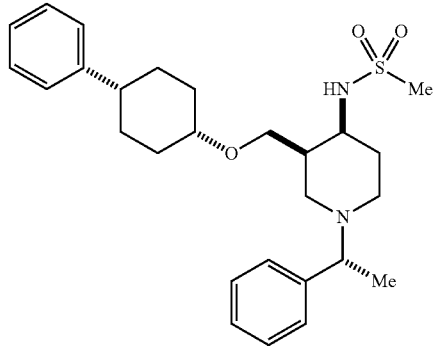

or a pharmaceutically acceptable salt thereof.

90. The compound of claim 1, wherein the compound is:

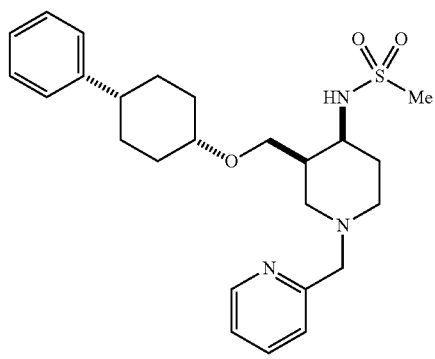

or a pharmaceutically acceptable salt thereof.

91. The compound of claim 1, wherein the compound is:

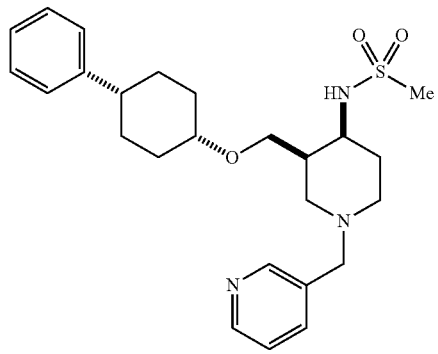

or a pharmaceutically acceptable salt thereof.

92. The compound of claim 1, wherein the compound is:

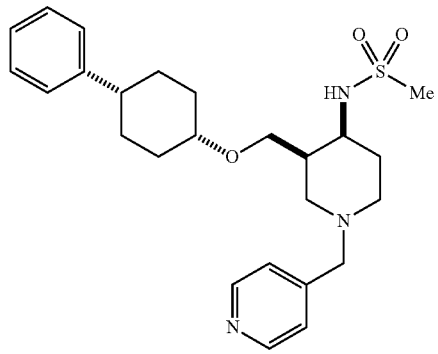

or a pharmaceutically acceptable salt thereof.

93. The compound of claim 1, wherein the compound is:

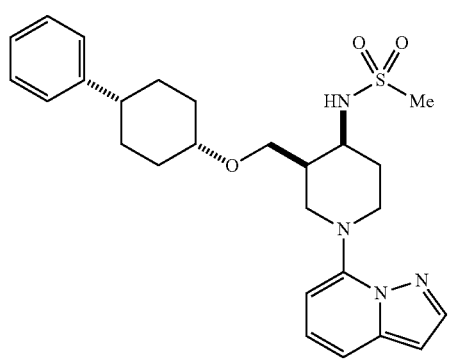

or a pharmaceutically acceptable salt thereof.

94. The compound of claim 1, wherein the compound is:

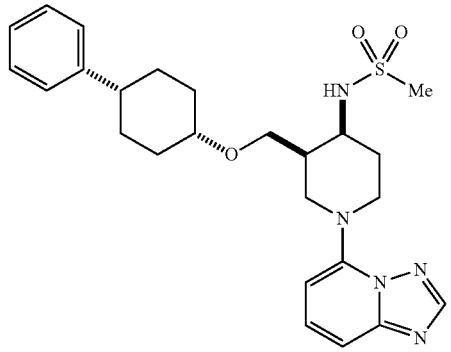

or a pharmaceutically acceptable salt thereof.

95. The compound of claim 1, wherein the compound is:

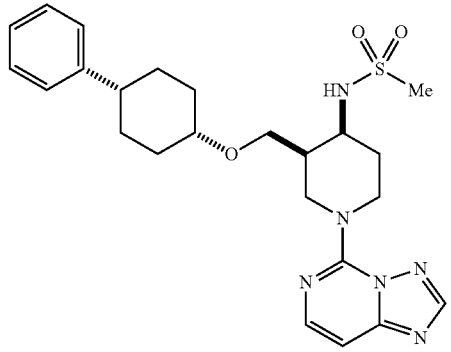

or a pharmaceutically acceptable salt thereof.

96. The compound of claim 1, wherein the compound is:

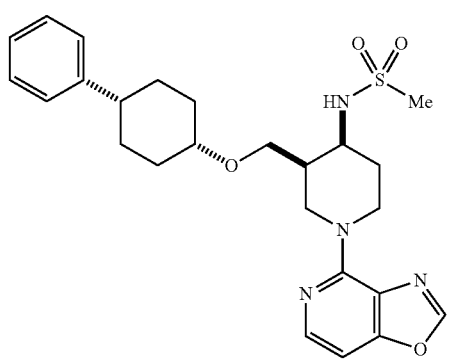

or a pharmaceutically acceptable salt thereof.

97. The compound of claim 1, wherein the compound is:

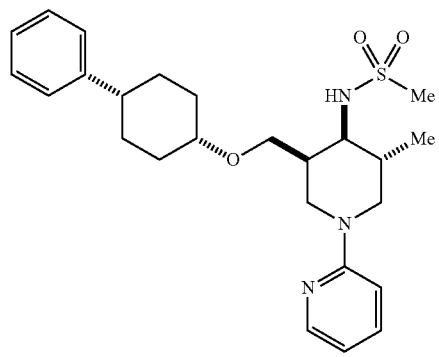

or a pharmaceutically acceptable salt thereof.

98. The compound of claim 1, wherein the compound is:

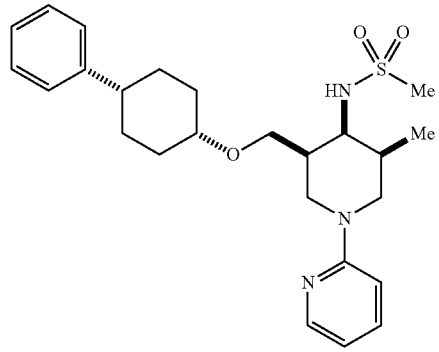

or a pharmaceutically acceptable salt thereof.

99. The compound of claim 1, wherein the compound is:

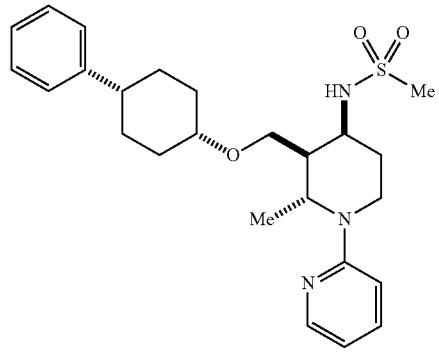

or a pharmaceutically acceptable salt thereof.

100. The compound of claim 1, wherein the compound is:

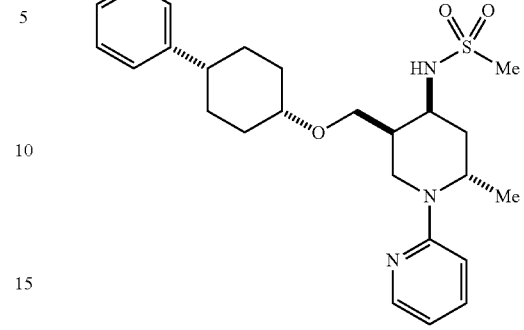

or a pharmaceutically acceptable salt thereof.

101. The compound of claim 1, wherein the compound is:

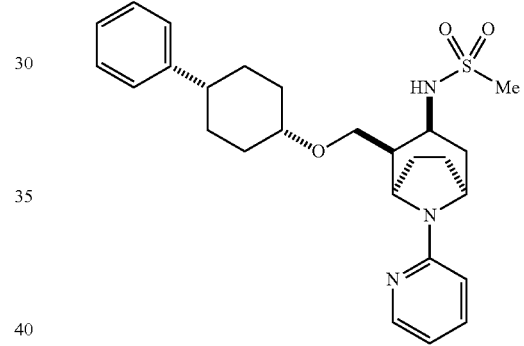

or a pharmaceutically acceptable salt thereof.

102. The compound of claim 1, wherein the compound is:

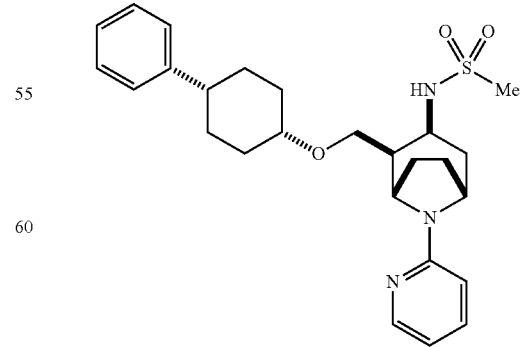

or a pharmaceutically acceptable salt thereof.

103. The compound of claim 1, wherein the compound is:

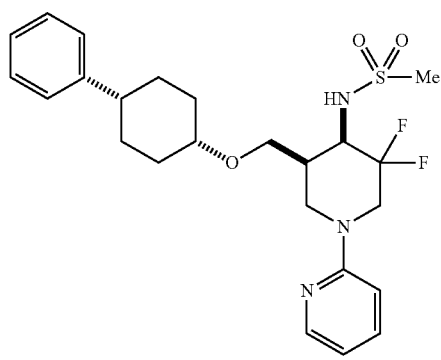

or a pharmaceutically acceptable salt thereof.

104. The compound of claim 1, wherein the compound is:

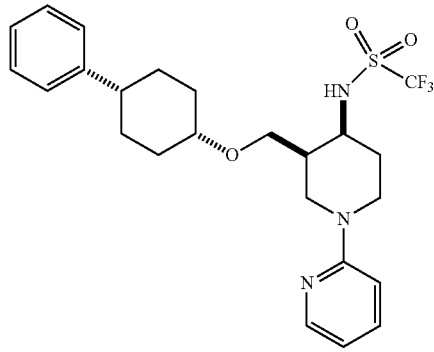

or a pharmaceutically acceptable salt thereof.

105. The compound of claim 1, wherein the compound is:

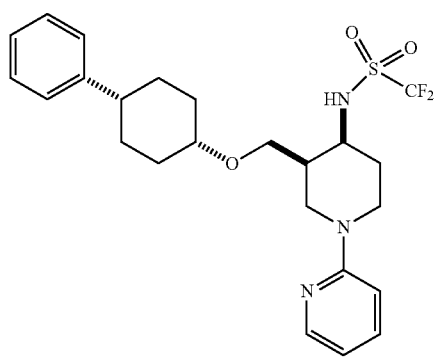

or a pharmaceutically acceptable salt thereof.

106. The compound of claim 1, wherein the compound is:

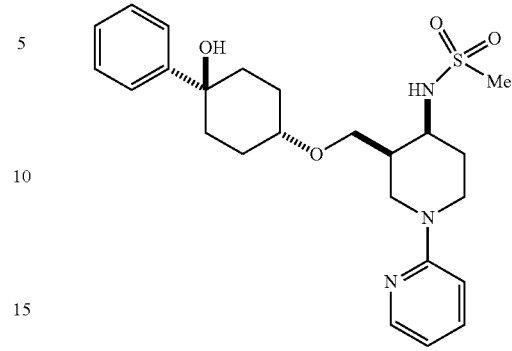

or a pharmaceutically acceptable salt thereof.

107. The compound of claim 1, wherein the compound is:

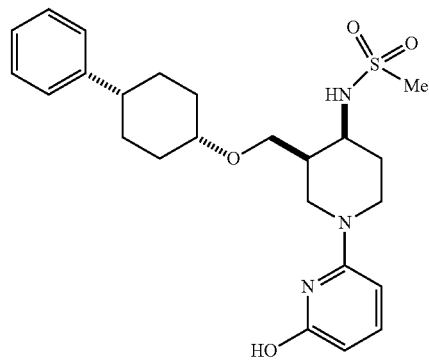

or a pharmaceutically acceptable salt thereof.

108. The compound of claim 1, wherein the compound is:

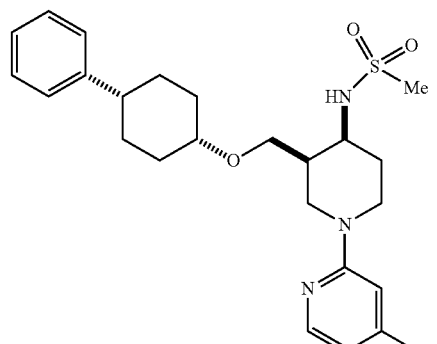

or a pharmaceutically acceptable salt thereof.

109. The compound of claim 1, wherein the compound is:

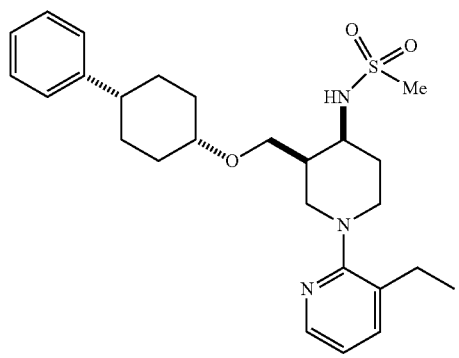

or a pharmaceutically acceptable salt thereof.

110. The compound of claim 1, wherein the compound is:

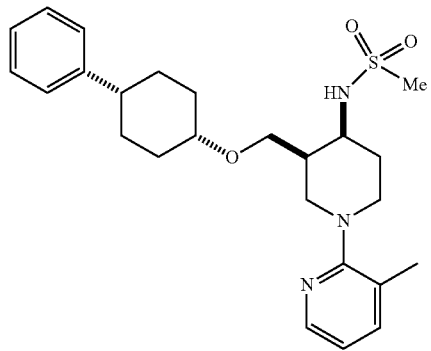

or a pharmaceutically acceptable salt thereof.

111. The compound of claim 1, wherein the compound is:

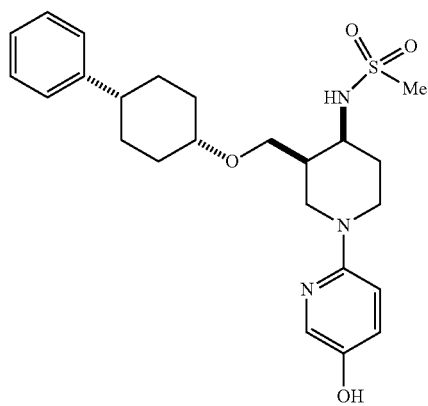

or a pharmaceutically acceptable salt thereof.

112. The compound of claim 1, wherein the compound is:

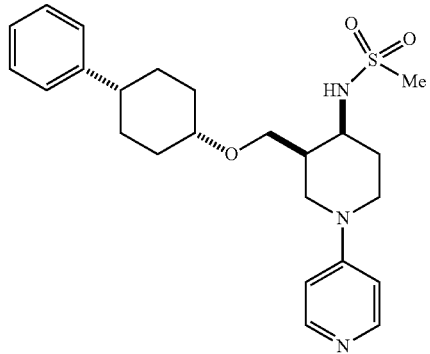

or a pharmaceutically acceptable salt thereof.

113. The compound of claim 1, wherein the compound is:

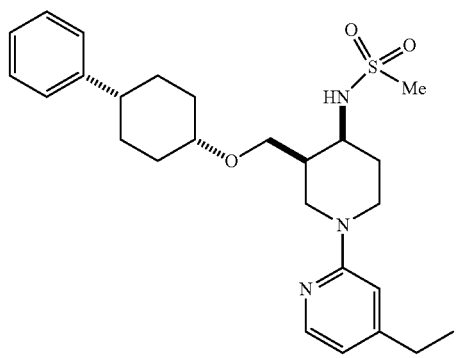

or a pharmaceutically acceptable salt thereof.

114. The compound of claim 1, wherein the compound is:

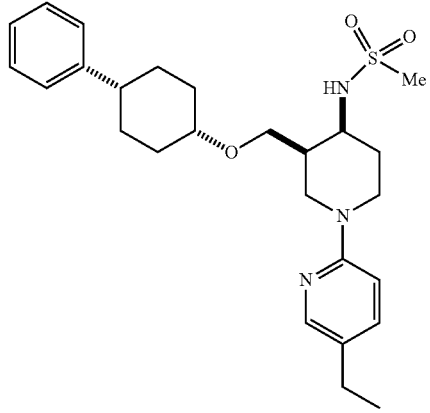

or a pharmaceutically acceptable salt thereof.

115. The compound of claim 1, wherein the compound is:

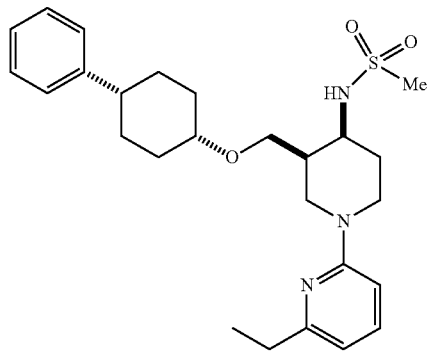

or a pharmaceutically acceptable salt thereof.

116. The compound of claim 1, wherein the compound is:

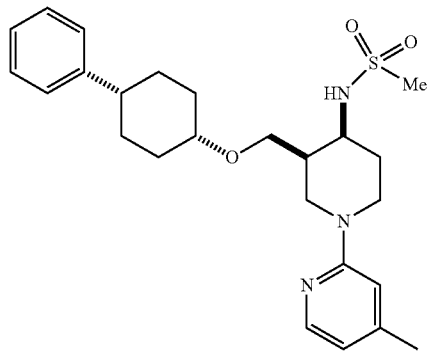

or a pharmaceutically acceptable salt thereof.

117. The compound of claim 1, wherein the compound is:

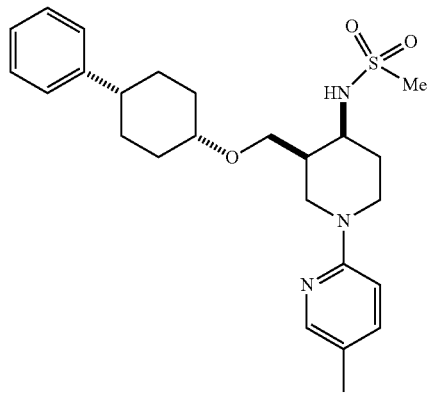

or a pharmaceutically acceptable salt thereof.

118. The compound of claim 1, wherein the compound is:

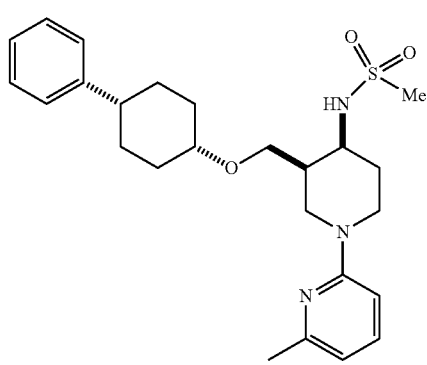

or a pharmaceutically acceptable salt thereof.

119. The compound of claim 1, wherein the compound is:

or a pharmaceutically acceptable salt thereof.

120. The compound of claim 1, wherein the compound is:

or a pharmaceutically acceptable salt thereof.

121. The compound of claim 1, wherein the compound is:
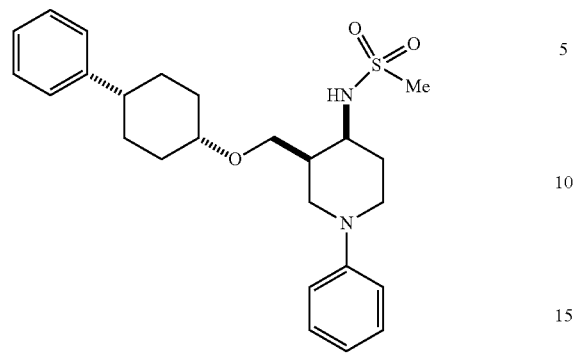
or a pharmaceutically acceptable salt thereof.
* * * * *

UNITED STATES PATENT AND TRADEMARK OFFICE
CERTIFICATE OF CORRECTION

PATENT NO. : 11,760,747 B2
APPLICATION NO. : 17/556295
DATED : September 19, 2023
INVENTOR(S) : Lewis D. Pennington et al.

Page 1 of 1

It is certified that error appears in the above-identified patent and that said Letters Patent is hereby corrected as shown below:

In the Claims

<u>Column 104</u>
In Claim 44, Line 19, please delete "Ru, Ria" and replace with -- $R_{11}$, $R_{12}$ --.

Signed and Sealed this
Twenty-first Day of January, 2025

Coke Morgan Stewart
*Acting Director of the United States Patent and Trademark Office*